(12) United States Patent
Zhang et al.

(10) Patent No.: US 7,666,585 B2
(45) Date of Patent: Feb. 23, 2010

(54) CONSTRUCTION OF CHIMERA PRRSV, COMPOSITIONS AND VACCINE PREPARATIONS

(75) Inventors: Xuexian Zhang, Maplewood, MN (US); Shi-jun Ma, Shoreview, MN (US)

(73) Assignee: ProtaTek International, Inc., St. Paul, MN (US)

( * ) Notice: Subject to any disclaimer, the term of this patent is extended or adjusted under 35 U.S.C. 154(b) by 0 days.

(21) Appl. No.: 11/763,822

(22) Filed: Jun. 15, 2007

(65) Prior Publication Data

US 2008/0311143 A1 Dec. 18, 2008

(51) Int. Cl.
*C12Q 1/70* (2006.01)
(52) U.S. Cl. ......................................................... 435/5
(58) Field of Classification Search ................ 435/69.1, 435/6
See application file for complete search history.

(56) References Cited

U.S. PATENT DOCUMENTS

| | | |
|---|---|---|
| 5,476,778 A | 12/1995 | Chladek et al. |
| 5,510,258 A | 4/1996 | Sanderson et al. |
| 5,587,164 A | 12/1996 | Sanderson et al. |
| 5,677,429 A | 10/1997 | Benfield |
| 5,683,865 A | 11/1997 | Collins et al. |
| 5,840,563 A | 11/1998 | Chladek et al. |
| 5,846,805 A | 12/1998 | Collins et al. |
| 5,989,563 A | 11/1999 | Chladek et al. |
| 5,998,601 A | 12/1999 | Murtaugh et al. |
| 6,015,663 A | 1/2000 | Wesley et al. |
| 6,033,844 A | 3/2000 | Visser et al. |
| 6,042,830 A | 3/2000 | Chladek et al. |
| 6,080,570 A | 6/2000 | Chladek et al. |
| 6,110,468 A | 8/2000 | Collins et al. |
| 6,241,990 B1 | 6/2001 | Collins et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,498,008 B2 | 12/2002 | Collins et al. |
| 6,500,662 B1 | 12/2002 | Calvert et al. |
| 6,841,364 B2 | 1/2005 | Yuan et al. |
| 6,855,315 B2 | 2/2005 | Collins et al. |
| 7,122,347 B2 | 10/2006 | Verheije et al. |
| 7,132,106 B2 | 11/2006 | Calvert et al. |
| 7,223,854 B2 | 5/2007 | Paul et al. |
| 7,273,617 B2 | 9/2007 | Yuan et al. |
| 7,279,166 B2 | 10/2007 | Meng et al. |
| 2002/0012670 A1 | 1/2002 | Elbers et al. |
| 2003/0049274 A1 | 3/2003 | Meulenberg et al. |
| 2003/0186225 A1 | 10/2003 | Paul et al. |
| 2004/0009190 A1 | 1/2004 | Elbers et al. |
| 2004/0208899 A1 | 10/2004 | Collins et al. |
| 2005/0053621 A1 | 3/2005 | Welch et al. |
| 2006/0205033 A1 | 9/2006 | Meulenberg et al. |
| 2006/0240041 A1 | 10/2006 | Meulenberg et al. |

FOREIGN PATENT DOCUMENTS

| | | |
|---|---|---|
| DE | 10003372 | 8/2001 |
| EP | 839912 | 5/1998 |
| EP | 1018557 | 7/2002 |
| WO | WO 01/55353 | 8/2001 |
| WO | 02/072802 | 9/2002 |
| WO | WO 2003/062407 | 7/2003 |

OTHER PUBLICATIONS

Barfoed, A.M. et al., "DNA vaccination of pigs with open reading frame 1-7 of PRRS virus," Vaccine (2004) 22:3628-3641.
De Lima, M. et al., "Serologic marker candidates identified among B-cell linear epitopes of Nsp2 and structural proteins of a North American strain of porcine reproductive and respiratory syndrome virus," Virology (2006) 353:410-421.
Grebennikova, T.V. et al., "Genomic characterization of virulent, attenuated, and revertant passages of a North American porcine reproductive and respiratory syndrome virus strain," Virology (2004) 321:383-390.
Jiang, Y. et al., "Immunogenicity and protective efficacy of recombinant pseudorabies virus expressing the two major membrane-associated proteins of porcine reproductive and respiratory syndrome virus," Vaccine (2007) 25:547-560.
Meng, X-J. et al., "Sequence comparison of open reading frames 2 to 5 of low and high virulence United States isolates of porcine reproductive and respiratory syndrome virus," J. Gen. Virol. (1995) 76:3181-3188.
Oleksiewicz, M.B. et al., "Epitope mapping porcine reproductive and respiratory syndrome virus by phage display: the nsp2 fragment of the replicase polyprotein contains a cluster of B-cell epitopes," J. Virol. (2001) 75(7):3277-3290.
Oleksiewicz, M.B. et al., "Porcine B-cells recognize epitopes that are conserved between the structural proteins of American- and European-type porcine reproductive and respiratory syndrome virus," J. Gen. Virol. (2002) 83:1407-1418.
Ostrowski, M. et al., "Identification of neutralizing and nonneutralizing epitopes in the porcine reproductive and respiratory syndrome virus GP5 ectodomain," J. Virol. (2002) 76(9):4241-4250.
Rodriguez, M.J. et al., "Epitope mapping of the nucleocapsid protein of European and North American isolates of porcine reproductive and respiratory syndrome virus," J. Gen. Virol. (1997) 78:2269-2278.
United States Office Action for U.S. Appl. No. 10/346,004 dated Mar. 23, 2004 (12 pages).
United States Office Action for U.S. Appl. No. 10/977,375 dated Jan. 31, 2007 (8 pages).

(Continued)

*Primary Examiner*—Ali R. Salimi
(74) *Attorney, Agent, or Firm*—Merchant & Gould P.C.

(57) ABSTRACT

Chimeric replicons of North American Porcine Reproductive and Respiratory Syndrome Virus (PRRSV) containing the 5' sequence of an avirulent strain of PRRSV and a 3' sequence of a virulent strain of PRRSV are provided. Further provided is a method of producing attenuated PRRSV from the chimeric replicon. Also provided are compositions containing the replicon or attenuated virus. Vaccines and a method of vaccinating pigs against PRRSV are also provided.

5 Claims, 5 Drawing Sheets

OTHER PUBLICATIONS

International Search Report of the International Searching Authority for PCT/US2003/001810 dated Mar. 2, 2004 (3 pages).

International Search Report and Written Opinion of the International Searching Authority for PCT/US2007/071341 dated Mar. 4, 2008 (15 pages).

Allende, R. et al., "Mutations in the genome 7 of porcine reproductive and respiratory syndrome virus responsible for the attenuation phenotype," Archives of Virology (2000) 145(6):1149-1161.

Boyer, J-C. et al., "Infectious transcripts and cDNA clones of RNA viruses," Virology (1994) 198:415-426.

Collins et al., "Isolation of swine infertility and respiratory syndrome virus (Isolate ATCC-VR2332) in North America and experimental reproduction of the disease in gnotobiotic pigs," J. Vet Diagn Invest (1992) 4:117-126.

Conzelmann, K-K. et al., "Genetic engineering of animal RNA viruses," Elsevier Science (1996) 386-393.

GenBank Accession # AF184212 (2000) (Shen).

GenBank Accession # U87932 (1998) (Mirel).

Meulenberg et al., "Infectious transcripts from cloned genome-length cDNA of porcine reproductive and respiratory syndrome virus," J. Virol. (1998) 72(1):380-387.

Nielsen, H.S. et al., "Generation of an infectious clone of VR-2332, a highly virulent North American-type isolate of porcine reproductive and respiratory syndrome virus," J. Virol. (2003) 77(6):3702-3711.

Palese, P., "Genetic engineering of infectious negative-strand RNA viruses," Elsevier Science Ltd. (1995) 3(4):123-125.

Shen, S. et al., "Determination of the complete nucleotide sequence of a vaccine strain of porcine reproductive and respiratory syndrome virus and identification of the Nsp2 gene with a unique insertion," Archives of Virology (2000) 145(5):871-883.

Snijder, E.J. et al., "The molecular biology of arteriviruses," J.Gen Virol (1988) 79:961-979.

Wensvoot, et al., "Mystery swine disease in the Netherlands: the isolation of Lelystad virus," Vet. Q (1991) 13:121-130.

Yuan et al., "Heteroclite subgenomic RNAs are produced in porcine reproductive and respiratory syndrome virus infection" Virology (2000) 275:158-169.

Osorio, "Rational Design of New Generation of PRRSV Differential (Marker) Vaccines." *Research Report, Swine Health*, 2005, pp. 1-6.

CONSTRUCTION OF CHIMERA PRRSV, COMPOSITIONS AND VACCINE PREPARATIONS

CROSS REFERENCE TO RELATED APPLICATIONS

N/A

STATEMENT REGARDING FEDERALLY SPONSORED RESEARCH OR DEVELOPMENT

N/A

INTRODUCTION

The present invention relates to molecular virology. More particularly, the invention encompasses methods of attenuating Porcine Reproductive and Respiratory Syndrome Virus (PRRSV) and viral compositions that include attenuated PRRSV.

Porcine Reproductive and Respiratory Syndrome (PRRS) is the most economically significant disease affecting the swine industry, with an estimated annual loss of up to $560 million in the United States. Primary symptoms of the disease are reproductive problems in sows and gilts, including late-term abortions, stillbirths and mummies, as well as litters of small weak pigs that are born viremic and often fail to survive. In addition, the syndrome may be manifested as a respiratory disease in young pigs which causes fever, lethargy, labored breathing, loss of appetite, slow growth and occasionally death, often in association with other respiratory pathogens. The disease can also be transmitted to sows and gilts via the semen of infected boars, either naturally or by artificial insemination.

PRRSV, the causative agent of the syndrome, has also been implicated as the etiological agent in other porcine diseases such as Postweaning Multisystem Wasting Syndrome (PMWS), and Porcine Respiratory Complex Disease (PRCD). The latter syndromes may be due to the immune suppression caused by PRRSV, which targets macrophages of the host immune system.

PRRSV is a member of the Arteriviridae, which belongs to the order of Nidovirales along with the Coronaviridae. It is a positive-stranded RNA virus which encodes 7 to 10 open reading frames (ORFs), flanked with the 5' and 3' terminal untranslated regions (UTRs). It is believed that the UTRs contain the cis-acting regulatory elements for genomic and subgenomic RNA replication and transcription. The PRRSV virion is composed of six structural proteins (encoded by ORFs 2 to 7). The product of ORF5 plays a critical role in virus entry of cells and stimulates neutralizing immunity. The ORF5 sequence represents the most variable region in the genome, which contributes to diverse genetic and antigenic variations of the virus. The genetic diversity of PRRSV has complicated efforts to develop an effective vaccine against PRRSV disease and its related syndromes.

There are commercial PRRSV vaccines available, including live-attenuated and killed virus vaccines. Unfortunately, the available vaccines have not exhibited sufficient immunoprotection in vaccinated herds. Safety of the live-attenuated vaccines has also been called into question. Moreover, current vaccines offer little protection against heterologous challenge by genetically diversified PRRSV strains. In addition, current vaccines provide no features for differentiating the natural infection from vaccine strains. Vaccines exhibiting significant improvements in safety, efficacy and identification are needed.

Virus attenuation through cell culture passage adversely affects the efficacy of vaccine derived from attenuated viruses in several respects. On one hand, the replication ability of the vaccine virus is affected under the fitness selection. On the other hand, high-level attenuation through cell culture creates antigenic variation due to the high mutation rate of an RNA virus. Therefore, a conventional attenuated vaccine would not offer the cross-protection against other forms of genetically diversified PRRSV isolates. There is a need for an attenuated virus that has growth characteristics and antigenic abilities to protect against homologous and heterologous strains of PRRSV.

BRIEF SUMMARY OF INVENTION

The inventors have discovered a region of the PRRSV genome which encodes for the virulence factors of PRRSV. This discovery provided the basis for development by the inventors of a novel approach for attenuation of field isolated virulent stains of PRRSV. In this approach, the virulent region of the virus is substituted with the corresponding region from an avirulent strain to produce a chimeric virus. The chimeric virus is non-pathogenic in host animals, yet provokes a protective immune response to homologous and heterologous PRRSV challenge. This approach provides an alternative to serially-passaged attenuated virus vaccines. In contrast to traditional vaccines, the vaccine compositions described herein provide cross-protection against diversified PRRSV isolates.

In one aspect, the invention provides a chimeric PRRSV replicon. The replicon includes a 5' sequence derived from an avirulent strain of PRRSV and a 3' sequence derived from a virulent stain of PRRSV. The 5' sequence includes ORF 1, ORF2, a portion of ORF3, or a combination thereof and the 3' sequence sufficiently completes the genome such that the replicon is capable of producing an infectious virus particle that is attenuated relative to the virulent strain.

In another aspect, the invention provides a method of producing an infectious attenuated chimeric PRRSV. The method includes transfecting a cell with a replicon comprising a 5' sequence derived from an avirulent strain of PRRSV and the 3' sequence derived from a virulent strain of PRRSV. The 5' sequence includes ORF1, ORF2, part of ORF3, or a combination thereof, and a 3' sequence that sufficiently completes the genome such that the replicon is capable of producing an infectious viral particle. The method further includes steps of incubating the cell under conditions suitable for production of infectious virus particles and recovering the virus particles, wherein the recovered virus is attenuated relative to the virulent strain of PRRSV.

In other aspects, the invention includes the attenuated virus produced from the method described above, compositions comprising the attenuated virus or replicon, and vaccines comprising the composition.

Other aspects of the invention will become apparent by consideration of the detailed description and accompanying drawings.

DETAILED DESCRIPTION

Figure 1:
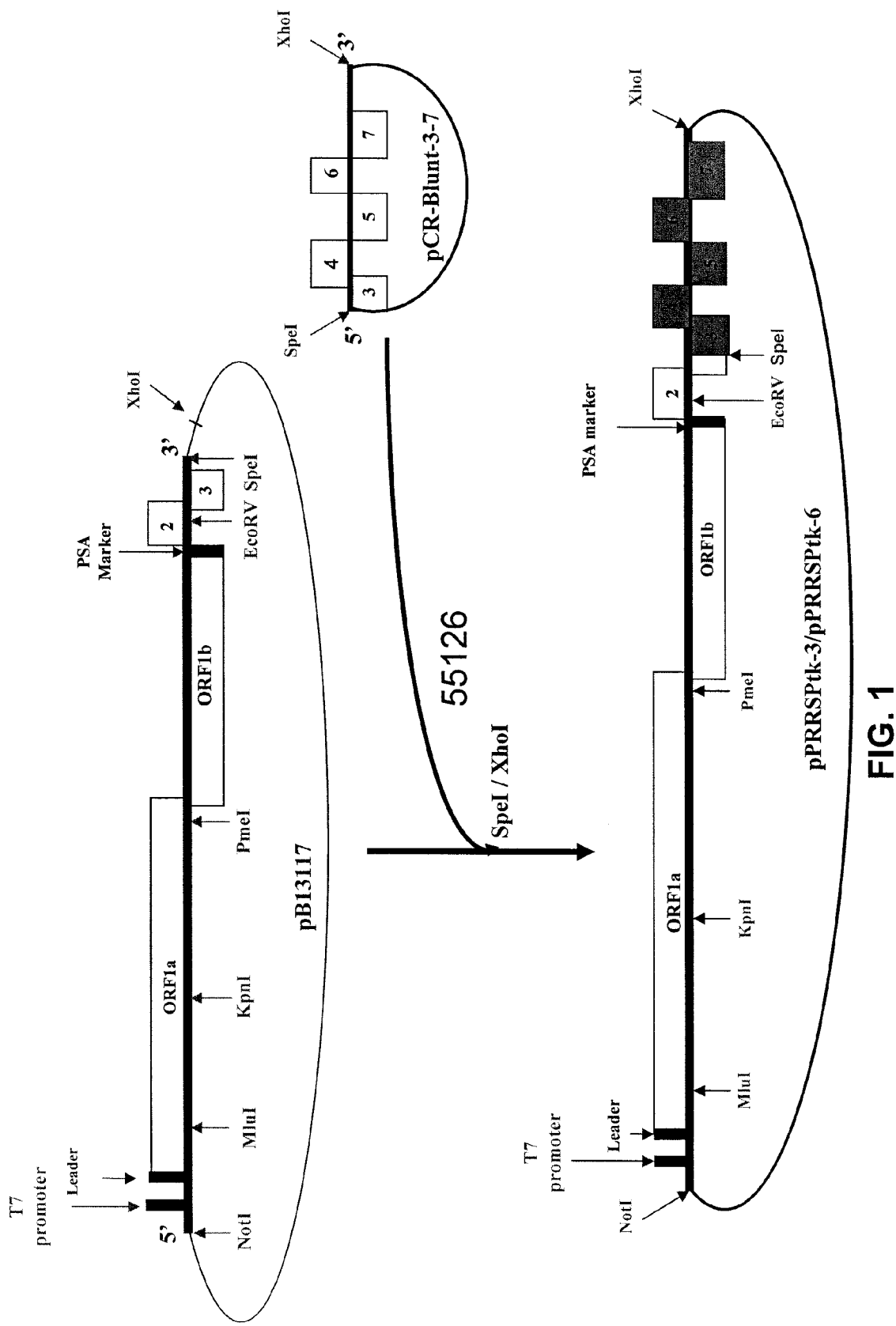
FIG. 1 is a schematic drawing depicting the construction of a chimeric PRRSV replicon including a genetic marker (PSA), a 5' sequence from clone pB13117, and a 3' sequence derived from a virulent field isolate of PRRSV.

The present invention relates to chimeric PRRSV replicons for producing an attenuated infectious PRRSV chimera. Furthermore, the invention relates to methods of producing such strains and use of such strains in vaccines. A "PRRSV replicon" as described herein is a DNA molecule or RNA molecule, or a region of DNA or RNA that replicates from a single origin of replication, i.e., a plasmid, cDNA clone, or vector. The term replicon encompasses cDNA generated from PRRSV viral genomic RNA via in vitro techniques, cDNA resulting from the reverse transcription of genomic RNA, vectors incorporating such cDNA, cDNA fragments produced by RT-PCR or restriction endonuclease digestion and recombinant nucleotide sequences that contain synthetic coding or non-coding sequences. The replicon is capable of in vivo RNA replication and production of an infectious PRRSV viral particle. The replicon transcribed in vitro or in vivo by host cell RNA polymerase is capable of completing the viral infectious cycle in host cells.

The replicon includes a 5' sequence from an avirulent strain of PRRSV and a 3' sequence from a virulent strain of PRRSV. A "5' sequence of an avirulent strain of PRRSV" refers to any portion of a sequence identical or corresponding to the first 13117 base pairs of SEQ ID NO: 1. For example, in reference to SEQ ID NO: 1, ORF1a spans nucleotides 192-7798, ORF1b spans nucleotides 7797-12181, ORF2 spans nucleotides 12183-12953, and the partial sequence of ORF3 spans nucleotides 12806-13117. It is contemplated that if another avirulent strain of PRRSV is used, the sequence of ORF 1-3 may differ. The 5' sequence is suitably derived from any attenuated PRRSV strains, such as ptkPRRS (SEQ ID NO: 1), ptk-PRRS-1 (SEQ ID NO 2), avirulent strains described in U.S. Pat. No, 6,841,364, serially-passaged strains that exhibit reduced virulence, or other avirulent strains known in the art. The 3' sequence is derived from a virulent strain, e.g., a field isolated PRRSV, and supplies all necessary sequences for the chimera to produce an infectious viral particle, i.e., it completes the genome. Suitable virulent strains are strains isolated from serum of infected pigs by means known in the art. Examples include strains termed "MN-184," "NADC-20," and VR-2332.

Virulence of a virus refers to the ability of a virus, when compared with other closely related viruses, to produce pathogenicity in a host. For PRRSV, a "virulent" strain causes disease, i.e., abortions, early furrowing, increased stillbirths, mummies and pre-weaning mortality and infertility in infected sows and gross lung lesions and pneumonia and increased mortality in suckling and fattening pigs and increased susceptibility to secondary infections. "Avirulent" strains are strains where the virulence of a strain has been attenuated, e.g., reduce the symptoms of PRRSV infection in a pig relative to the virulent strain. Suitably, the attenuation of virulence of an avirulent strain may be evaluated by a reduction in the gross histopathological changes (e.g., lung lesions) and/or reduction in the symptoms of the disease, as compared to a control. Symptoms of PRRSV include, but are not limited to, e.g., fever, respiratory distress, lethargy, forced expiration, sneezing, coughing, eye edema, or roughened haircoats. Methods of evaluating symptoms are known in the art. Attenuation of a virulent strain of PRRSV may be measured by reduction of lung lesions, e.g., as described in the examples below. Suitably, the number of lung lesions is reduced at least 10%, at least 20%, at least 30%, at least 50%, at least 60%, at least 70%, at least 80%, at least 100%, at least 200% relative to a non-vaccinated control.

Virulence of a chimera is suitably compared to the virulent "parental" strain of PRRSV and reduced virulence clones may be selected as suitable vaccine candidates. For example, virulence of chimeric PRRSV in comparison to a field isolate may be tested by the methods described in Example 8, i.e., by examination of lung lesions, growth performance, sero-conversion and body temperature of pigs infected with the chimeric PRRSV strain. Any other suitable method of testing virulence may be used.

The chimera of PRRSV contains 5' and 3' sequences that, in combination, complete a full-length infectious replicon, e.g., ORF 1-7. It is to be understood that the full-length infectious replicon may contain insertions or deletions that do not affect the ability of the replicon to produce infectious particles, and these insertions and deletions may alter the number or sequence of nucleotides in the full-length replicon without affecting function. For example if the 5' sequence from the avirulent strain contains the 5' untranslated region (UTR), ORF1a and ORF1b, then the 3' sequence from the field isolate will contain the sequence for ORF2-7 and 3' UTR to produce a full-length replicon. As a further example, if the 5' sequence encodes for nucleotides 1-8000 corresponding to SEQ ID NO: 1 of the full-length sequence, then the 3' sequence will include nucleotides 8001-15521. Any combination of 5' and 3' sequences may be constructed and the resulting chimeras may be tested for virulence according to standard protocols. A sequence "derived from" a reference sequence refers to a synthetic peptide or polynucleotide or a sequence prepared by molecular biology methods, using an isolated strain of virulent or avirulent PRRSV as a template.

Methods of preparing an avirulent infectious clone of PRRSV are described in U.S. Pat. No. 6,841,364, which is incorporated by reference herein in its entirety. This patent describes, among other clones, ptkPRRS (SEQ ID NO: 1). The examples below describe the construction of replicons that can produce attenuated PRRSV which are based, in part, on this sequence. However, it is to be understood that the methods can be practiced using any combination of virulent and avirulent strains of PRRSV such that desired characteristics are achieved in the resulting chimera of PRRSV. The resultant chimeric replicon contains all the necessary nucleotides and amino acids to produce an infectious viral particle, for example ORF 1-7. It is understood that replicons of the invention may be of any length, and include additions or deletions that do not affect the ability of the replicon to produce infectious viral particles. An "infectious" viral particle is a virus with all the necessary components to enter and replicate within a cell.

PRRSV replicons suitably further comprise a genetic marker sequence. A "genetic marker sequence" is a sequence that is inserted into the PRRSV genome without altering viral gene expression, which can be used to identify replicons or viral progeny. Identification of the marker sequence is suitably accomplished by isolation of the sequence followed by sequencing or restriction enzyme digestion and fragment visualization techniques that are well-known in the art. As will be appreciated, genetic modifications of PRRSV DNA of the invention will be useful as a means of differentiating engineered PRRSV from that of field isolates or commercial vaccine strains. Genetic marker sequences are added by suitable means to the engineered replicon for later identification. Specific embodiments contemplated include genetically marked PRRSV replicons comprising an MluI site introduced by substitution in ORF5, an NdeI site introduced by insertion in the 3' UTR, PacI, SwaI, AscI or VspI sites introduced by insertion at the junction of ORF1 and ORF2, or by deletion of sequences in the 3' end of the ORF7 and 5' part of ORF2 or in the middle of ORF4, as described in U.S. Pat. No. 6,841,364. It is contemplated that any suitable restriction digestion site or polylinkers may be used to "mark" chimeric PRRSV DNA in the practice of this invention.

In another embodiment, the invention provides a cell comprising the replicon described above. The cell is not limited to any particular cell type, but must be capable of expressing the replicon to provide infectious RNAs or viral particles under suitable conditions. The cell may be permissive and/or susceptible. "Permissive" cells are cells which can be used by the virus to replicate and produce viral particles upon introduction of viral RNA or infectious cDNA. Permissive cells may or may not have a cell surface receptor for the virus. "Susceptible" cells, on the other hand, are cells bearing surface receptors for the virus, and which can be used by the virus to complete multiple cycles of proliferation and infection. Examples of suitable cells include, but are not limited to, simian cell lines and porcine cells. Simian kidney cell lines are suitable for in vitro applications. Once such line, African Green Monkey continuous cell line MA-104, as well as its progeny line Marc 145, are commercially available. PRRSV exhibits tropism for lung alveolar macrophages in vivo and these cells are also suitable in vitro multiplicity of PRRSV.

In another embodiment, the invention provides a method of producing an attenuated infectious PRRSV virus. The method includes steps of transfecting a cell with a replicon described above, incubating the cell under conditions suitable for production of an infectious virus particle, and recovering the virus particle. In vitro delivery methods of the replicon into a cell are known in the art and include, but are not limited to, transfection (including microinjection, electroporation, calcium phosphate precipitation, using DEAE-dextran followed by polyethylene glycol, direct sonic loading, liposome-mediated transfection and receptor-mediated transfection), transduction by viral vector, and/or any combination of such methods. Methods that can be used to recover virus particles from cells are well known in the art, e.g., the method of Example 5. The cells are cultured under conditions that allow expression of the replicon. Typically, standard culture conditions are sufficient.

In further embodiments, an attenuated virus produced from a chimeric replicon has similar growth kinetics to a virulent stain of PRRSV. "Substantially identical growth kinetics" of a virus can be monitored in vitro by measuring the viral titer over time where the titer is within about 10% of a reference strain. The growth kinetics of the chimeric virus are suitably compared to the virulent strains from which the chimera is derived.

Compositions including the chimeric replicon or attenuated virus are also within the scope of the invention. Such compositions typically include the replicon or chimeric virus and a physiologically acceptable vehicle. A "physiologically acceptable" vehicle is any vehicle that is suitable for in vivo administration (e.g., oral, transdermal or parenteral administration) or in vitro use, i.e., cell culture. Suitable physiologically acceptable vehicles for in vivo administration include water, buffered solutions and glucose solutions, among others. A suitable vehicle for cell culture is commercially available cell media. Additional components of the compositions may suitably include excipients such as stabilizers, preservatives, diluents, emulsifiers or lubricants, in addition to the physiologically acceptable vehicle and the replicon or attenuated virus. In particular, suitable excipients include, but are not limited to, Tween 20, DMSO, sucrose, L-histadine, polysorbate 20 and serum.

Some embodiments of the invention provide a method of stimulating an immune response in a mammal. Suitably the mammal is a porcine species. "Stimulating an immune response" includes, but is not limited to, inducing a therapeutic or prophylactic effect that is mediated by the immune system of the mammal. More specifically, stimulating an immune response in the context of the invention refers to eliciting cellular or humoral immune responses, thereby inducing downstream effects such as production of antibodies, antibody heavy chain class switching, maturation of APCs, and stimulation of cytolytic T cells, T helper cells and both T and B memory cells. The immune response stimulated according to the invention by a chimeric virus may suitably promote a reduction in symptoms in the mammal as compared to the virulent strain.

As appreciated by skilled artisans, compositions are suitably formulated to be compatible with the intended route of administration. Examples of suitable routes of administration include parenteral, e.g., intravenous, intradermal, subcutaneous, oral (e.g., inhalation), transdermal (topical), transmucosal, and rectal administration. A suitable route of administration to swine is intramuscularly. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the composition is also suitably accomplished by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

Compositions of the invention are suitably formulated as a vaccine. As used herein, "vaccine" refers to a composition which, when administered to a subject, induces cellular or humoral immune responses as described herein. The effectiveness of the present vaccine may be evaluated by a reduction in the gross histopathological changes (e.g., lung lesions, mycocarditis, lymphadenitis, encephalitis and rhinitis) and/ or reduction in the symptoms of the disease, as compared to similar pigs that are not vaccinated or are administered a negative control before challenge by a field strain, e.g., as described in the examples below. Symptoms of PRRSV include, but are not limited to, e.g., fever, respiratory distress, lethargy, forced expiration, sneezing, coughing, eye edema, or roughened haircoats. Effectiveness of a vaccine may be measured by reduction of lung lesions. Suitably, the number of lung lesions is reduced at least 10%, at least 20%, at least 30%, at least 50%, at least 60%, at least 70%, at least 80%, at least 100%, at least 200% relative to a non-vaccinated control.

Suitable vaccine compositions include an infectious PRRSV replicon produced according to the invention or RNA or antigenic peptides produced in vitro from infectious PRRSV replicons. Additional suitable vaccine compositions include whole live attenuated virus produced using the replicon of the invention. Suitable vaccines also include the combination of two or more whole live attenuated chimeric viruses produced using replicons of the invention. Vaccine compositions may include an aqueous medium, pharmaceutically acceptable inert excipient such as lactose, starch, calcium carbonate, and sodium citrate. Vaccine compositions may also include an adjuvant, for example Freud's adjuvant. Vaccines may be administered alone or in combination with a physiologically acceptable vehicle that is suitable for administration to swine. Vaccines may be delivered orally, parenterally, intramuscularly, intranasally or intravenously. Oral delivery may encompass, for example, adding the compositions to the feed or drink of the mammals. Factors bearing on the vaccine dosage include, for example, the weight and age of the mammal. Compositions for parenteral or intravenous delivery may also include emulsifying or suspending agents or diluents to control the delivery and dose amount of the vaccine. Vaccines are suitably delivered in one intramuscular injection of about $1\times10^4$ to $1\times10^6$ virions per administration.

The following examples are provided to assist in a further understanding of the invention. The particular materials and conditions employed are intended to be further illustrative of the invention and are not limiting upon the reasonable scope thereof.

EXAMPLES

Example 1

Addition of a Genetic Marker Sequence to an Infectious Avirulent PRRSV Clone

A genetic maker, PacI/SwaI/AscI (PSA) polylinker (SEQ ID NO: 3), was inserted into the viral genome between ORF 1b and 2 without altering viral gene expression to identify vaccine virus from field isolates of PRRSV. The ptkPRRS clone (SEQ ID NO: 1, from U.S. Pat. No. 6,841,364) was used to construct the modified viral genome. PCR amplification was performed using two primer pairs, SF7682/PSA1R (SEQ. ID NO: 4/SEQ ID NO: 5) and PSA2F/Sp2R (SEQ ID NO: 6/SEQ ID NO: 7). Obtained PCR products were digested with restricted endonuclease PmeI/PacI and PacI/XhoI, respectively, and purified by an agarose gel. The ptkPRRS plasmid DNA was digested with PmeI and XhoI and purified by agarose gel. A ligation reaction was performed with digested plasmid DNA ptkPRRS, SF7628/PSA1R fragment, and PSA2F/Sp2R fragment. The new recombinant infectious clone was called as ptkPRRS-1 (SEQ ID NO: 2), in which PSA polylinker is located between ORF1 and ORF2. To validate exist of the genetic marker, PCR was performed with a primer pair: PSA polylinker/SR12709(SEQ ID NO: 8/SEQ ID NO: 9). Furthermore, restriction endonuclease PacI, AscI, and SwaI were used to digest the recombinant plasmid DNA and verified the modified PRRSV, ptkPRRS-1, includes a genetic marker PSA in viral genome.

Example 2

Subcloning of the 5' Sequence of an Avirulent Strain of PRRSV (13117bp) into pBluescript SK(+)

A subclone from clone ptkPRRS-1 was constructed to remove the 3' end of viral genome by using a unique restriction endouclease site SpeI in ptkPRRS-1. Plasmid DNA of the clone ptkPRRS-1 was digested with NotI and SpeI and the 5' end fragment containing ORF 1, ORF2 and partial sequence of ORF3 (13117 bp, SEQ ID NO: 10) was purified on an agarose gel. The purified fragment was cloned into plasmid vector pBluescript SK(+) (Stratagene, La Jolla, Calif.). This recombinant clone, designated as pB 13117, was used as a backbone to construct a chimeric infectious clone of PRRSV.

Example 3

Subcloning of the 3' Sequence of a Field Isolate Strain of PRRSV into Vector pCR-Blunt QIAamp Viral RNA Kit (Qiagen, Valencia, Calif.) was used to extract viral RNAs from porcine serum or cell culture supernatants. Porcine serum or cell culture supernatants from viral infection and buffer AVL with carrier RNA were added into a microcentrifuge tube (560 µl of AVL buffer with 140 µl of sample; both are proportionally). After mixing by pulse-vortexing for 15 seconds, the lysis was incubated at room temperature for 10 min, and then 560 µl of ethanol was added into the sample. After briefly mixing, sample was loaded into column and centrifuged at 8000 rpm for 1 min (Repeat it until all lysis solution is loaded). The column with sample was washed orderly with AW1 and AW2 buffer. Finally, RNAs were eluted with the elution buffer and stored at −80° C. The First-strand cDNA was synthesized using the SuperScript II Reverse Transcription Kit (Invitrogen, Carlsbad, Calif.) with the anchor primer SP2R (SEQ ID NO: 7). PCR amplification of target genomic region was conducted by the use of Pfu Turbo Hotstart DNA polymerase (Stratagene, La Jolla, Calif.) according to the protocol described by the manufacturer with the 1$^{st}$ stranded cDNA and primers. Specifically, synthesized forward primer SpeF (SEQ ID NO: 11) and anchor primer Sp2R (SEQ ID NO: 7) were used for amplification of the structural protein-coding region covering partial ORF3 through ORF7 from two field isolated strains, a portion of MN-184, SEQ ID NO: 12, or a portion of a new field isolate, SEQ ID NO:17. Gel-purified PCR product was cloned directly into pCR-Blunt vector according to the procedure described by the manufacturer (Invitrogen, Carlsbad, Calif.). This clone is designated as pCR-Blunt-3-7.

Example 4

Construction of Chimeric Full-length Replicon of PRRSV

Restriction endonucleases SpeI and XhoI (New England Biolabs, MA) were used to digest clone pB13117 and clone pCR-Blunt-3-7, respectively. The digested recombinant plasmid DNAs were separated on an argarose gel, and the target DNA bands were cut out and purified via QIEX II gel-purification kit (Qiagen). The purified DNAs, digested pB 13117 DNAs and DNA fragment of the 3' end of viral genome released from pCR-Blunt-3-7, were used to perform a ligation reaction as depicted in FIG. 1. Two full-length cDNA clones, designated as pPRRSPTK-3 (SEQ ID NO: 13) and pPRRSPTK-6 (SEQ ID NO: 14), have been constructed following this procedure. pPRRSPTK-3 included the 3' sequence of field strain MN-184 (SEQ ID NO:12) and pPRRSPTK-6 included the 3' sequence of a new field strain isolated (SEQ ID NO:17). The two clones were further characterized by restriction endonuclease digestion of recombinant plasmid DNAs and DNA sequencing.

Example 5

Formation of Chimeric PRRSV in Marc 145 Cells

DNAs of chimeric infectious PRRSV clone were transcribed in vitro. Marc145 cells were transfected with the synthesized RNAs. The two full-length clones, pPRRSPTK-3 and pPRRSPTK-6, were linearized with a restriction endonuclease XhoI at the downstream of the clones. The linearized template DNA was examined on an agarose gel to confirm that the cleavage is complete. Purified DNAs were used to perform in vitro transcription with mMESSAGE mMACHINE kit (Ambion, Austin, Tex.). Transcription reaction was assembled in a microcentrifuge tube with 2×NTP/CAP, 10× reaction buffer, enzyme mix, GTP, and linearized template DNA. After mixing well, the reaction was incubated in 37° C. for 2 h. The unincorporated nucleotides and most proteins were removed by lithium chloride (LiCl) precipitation and RNA was resuspended in nuclease-free water. Synthesized RNA by in vitro transcription was quantitated by UV absorbance and the quality checked on an agarose gel. Finally, RNAs were stored at −80° C. for RNA transfection in vitro. Marc-145 cells were prepared in a 6-well-plate (Corning Corp.) before a day of transfection. Transfection was conducted by using DMRIE-C reagent (Invitrogen, Carlsbad, Calif.) at the second day. Briefly, OPTI-MEM (1 ml) serum-free medium was mixed with 3 µl of DMRIE-C reagent by shortly vortexing. The RNAs (5 µl) from in vitro transcription were added into it and incubated at room temperature for a short time. The transfection mixture was transferred onto the cell monolayer pre-washed by 1×PBS. After incubation for 3 h at 37° C., 5% $CO_2$, the transfection mixture was aspirated off and the cells were replenished with EMEM medium (Invitrogen) containing 2% FBS. Cells were allowed to proceed for up to 6 days for typical cytopathic effect (CPE) appearance. To generate passage 1 of the infectious PRRSV, 500 µl of cell supernatants was used to infect fresh Marc 145 cells in $T_{75}$ flask under the same culture condition. Cell culture supernatants were harvested at showing 80% CPE and stored at −80° C. Two chimeric PRRSVs have been constructed and are known as PRRSPTK-3 and PRRSPTK-6.

Example 6

Genetic Marker Stability in Chimeric PRRSV

Viral RNA was extracted from cell culture supernatants with Qiagen Viral RNA Isolation Kit (QIAgen, Valencia, Calif.). The first-stranded cDNA was synthesized using the SuperScript II Reverse Transcription Kit, with the anchor primer Sp2R. PCR amplification of target genomic region was conducted by the use of Pfu Turbo Hotstart DNA polymerase (Stratagene, La Jolla, Calif.). Specifically, synthesized forward primer SpeF and anchor primer Sp2R were used for amplification of the structural protein-coding region covering ORF3 through 7. After chimeric virus was passed ten times in Marc145 cells, cell supernatants were collected for isolating viral RNA genome. Specific primer pairs (PSAF, SEQ ID NO: 15 (CCTTAATTAATTTAA ATGGCGCGCC), and SR12709, SEQ ID NO: 16 (CCCCGTCATGCGCAG-GTT GTGTAG) were used to perform PCR. The PCR product was about 550 bp on an agarose gel. A field isolate of PRRSV was used as a negative control without PCR amplification. Further, RT-PCR products of cell supernatants were sequenced for confirmation of chimeric virus. Chimeric PRRSV passed in pigs can be isolated from serum collected at day 10 to 14 post inoculation. The stability of genetic marker PSA in PRRSV genome was confirmed after passing in the host animals. Chimeric PRRSV is the similar to the parental PRRSV in viral viability and specificities. The viral titer can reach to 5.686 ($logTCID_{50}$/ml) for PRRSPTK-3 and 5.435 ($logTCID_{50}$/ml) for PRRSPTK-6.

Example 7

Virulence of Chimeric PRRSV in Host Animals

The virulence of chimeric PRRSV was tested in the host animals. In the first test, 5 pigs were vaccinated intramuscularly with a combination of PRRSPTK-3 and ptkPRRS (dose is $5 \times 10^4$ for each) and 5 pigs used as control. In the second test, 5 pigs were vaccinated intramuscularly with a combination of PRRSPTK-3 and PRRSPTK-6 of PRRSV (dose is $5 \times 10^5$ for each) and 5 pigs used as a control. At 14 days post-vaccination, all pigs were autopsied and the lung lesion scores were determined according to the established standard by clinical pathologist. As a positive control, 5 pigs were challenged with a parental PRRSV. The lung lesion scores were determined at 14 days post-challenge. The results shown in Table 1 demonstrate the genetically modified chimeric PRRSV is avirulent in pigs.

TABLE 1

Lung Lesion Scores of Vaccinated Pigs.

| Groups of pigs according to vaccination strains | # of Animals | Lung Lesion Scores (%) |
|---|---|---|
| PRRSPTK-3/ PtkPRRS | 5 | 0.30 |
| PRRSPTK-3/ PRRSPTK-6 | 5 | 0.04 |
| MN-184 | 5 | 61.00 |
| NADC-20 | 5 | 75.25 |
| Negative control | 5 | 0.02 |

Example 8

Immunogenecity of Chimeric PRRSV in Host Animals

A combination of PRRSPTK-3 and ptkPRRS was used to vaccinate pigs to test the immunogenicity of chimeric PRRSV. Twenty pigs were divided into 4 groups, 5 pigs per group. Pigs in group 1 and 2 were vaccinated with PRRSptk-3 and ptkPRRS (dosage is $5\times10^4$ for each) and group 3 and group 4 were non-vaccinated controls. At day 35 post vaccination, pigs in group 1 and group 3 were challenged with virulent heterologous PRRSV NADC-20 and pigs in group 2 and group 3 with PRRSV MN-184, respectively. After 14 days post challenge, the response to the virulent virus challenge were characterized for all pigs.

Figure 2:
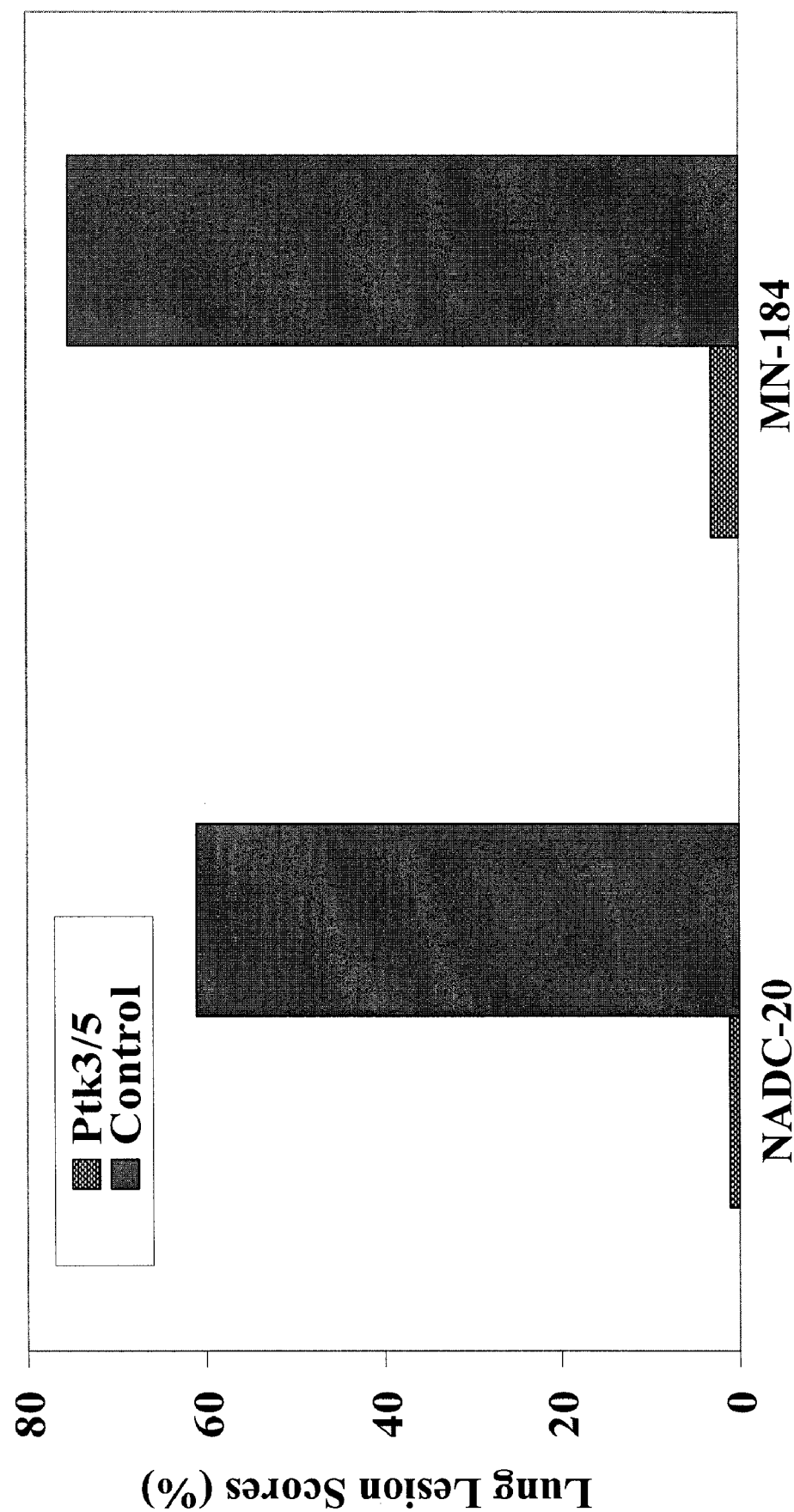
FIG. 2 is a bar graph showing a reduction in gross lung lesions caused by PRRSV infection at day 49 post-vaccination of pigs vaccinated with a chimeric virus of the invention, termed "PRRSPTK-3", and an avirulent strain ptkPRRS as compared with control pigs after challenge with virulent strains of PRRSV (NADC-20 or MN184).

A. Lung lesion scores. The lung lesion scores were determined at necropsy based on gross lung lesions, microscopic and immunohistological examinations at day 49 post vaccination. The average scores of each group were shown in FIG. 2. Vaccinated pigs showed the significant lower lung lesion scores in both homologous and heterologous challenge compared with non-vaccinated control: 1.07% vs. 61% for heterologous challenge and 3.15% vs. 75.25% for homologous challenge. The results indicated that chimeric PRRSV protected pigs from virulent PRRSV infection without causing PRRS clinical signs by itself.

Figure 4:
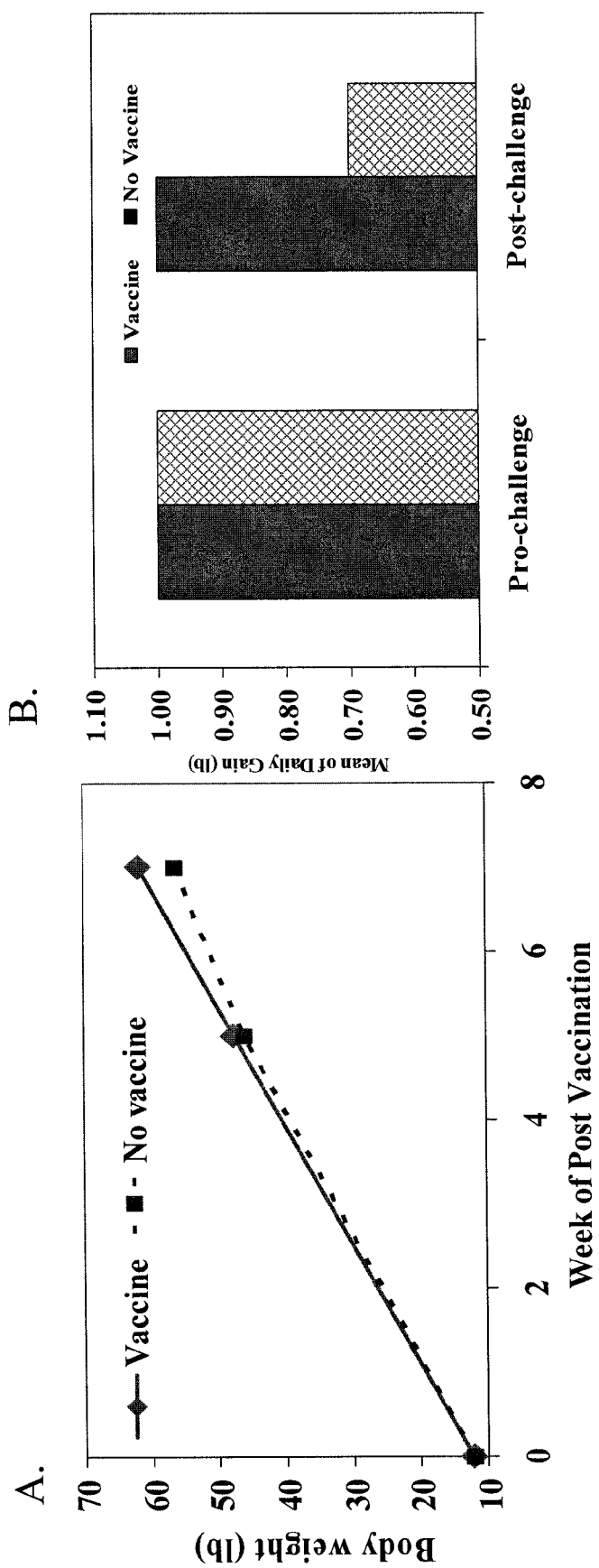
FIG. 4A is a graph showing pigs vaccinated with a combination of chimeric virus of the invention, termed "PRRSPTK-3", and an avirulent strain ptkPRRS had comparable body weight gain to the non-vaccinated control pigs over time.
FIG. 4B is a bar graph depicting weight gain results from pigs vaccinated with a combination of chimeric virus of the invention, termed "PRRSPTK-3", and an avirulent strain ptkPRRS followed by challenge with a virulent strain of PRRSV.

B. Growth Performance. Animals were weighed on day 0, 35, and 49 post vaccination. Average daily gains were calculated as pre- and post-challenge, respectively. As shown in FIG. 4, the vaccinated group significantly protected pigs from weight loss upon challenge, 1.01 pound per day compared to just 0.73 pound per day for the non-vaccinated controls. Before challenge with virulent PRRSV, there was no difference of daily gain between vaccinated and control pigs.

Figure 3:
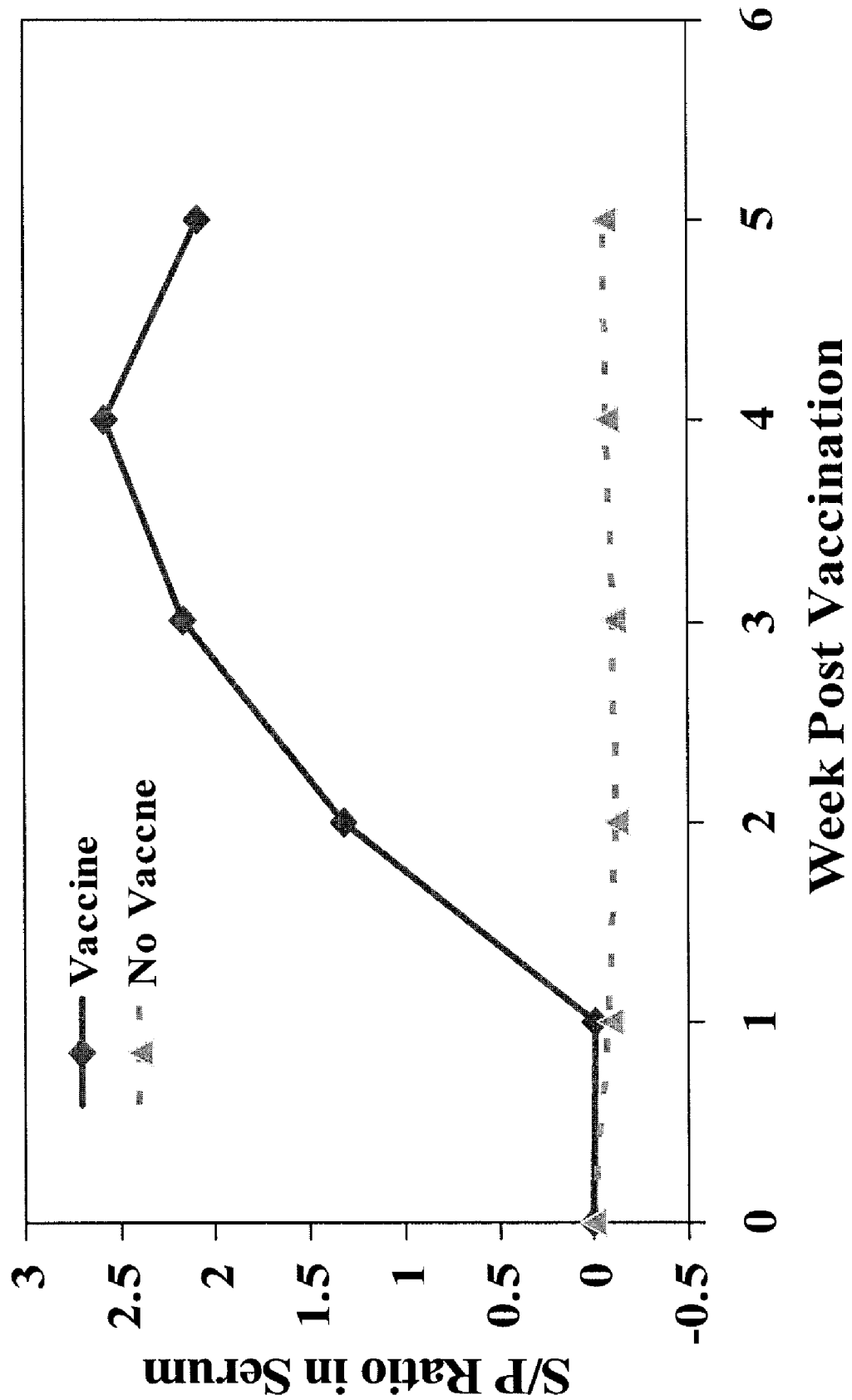
FIG. 3 is a graph depicting the increased in PRRSV-specific antibodies in serum of pigs vaccinated with a chimeric virus of the invention, termed "PRRSPTK-3", and an avirulent strain ptkPRRS as seen by increased S/P values over time.

C. Sero-conversion in the host animals by vaccination. Serum samples were collected every week for 5 weeks post vaccination, and subjected to ELISA test according to the instruction by the suppliers (IDEXX Inc. Maine). The S/P values of each group at each time-point were plotted against days post-vaccination as seen in FIG. 3. All of the vaccinated pigs converted to PRRSV-specific antibody positive after 14 days post vaccination by using the S/P cut-off value of 0.4. These results showed that the tested vaccines are immunogenic and stimulate a humoral immune response in the host animals.

Figure 5:
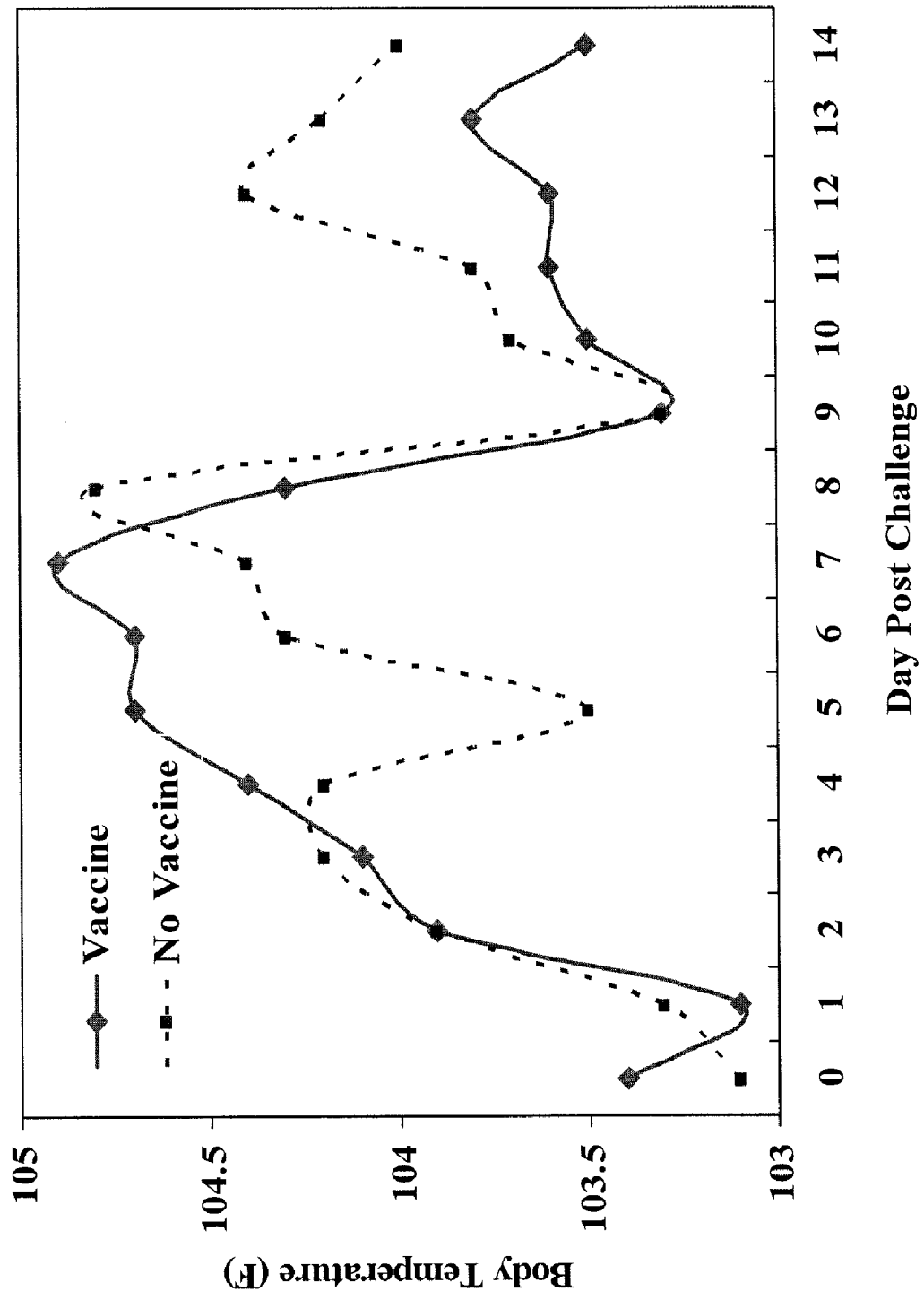
FIG. 5 is a graph showing the body temperature of pigs vaccinated with a combination of a chimeric virus of the invention, termed "PRRSPTK-3", and an avirulent strain ptkPRRS and non-vaccinated pigs over time.

D. Body Temperature Curve. Rectal temperature of each animal was daily recorded for 14 days post-challenge, starting one day before challenge. As seen in FIG. 5, vaccinated pigs 5 day post challenge showed higher body temperature compared to control pigs, but the body temperature of vaccinated pigs decreased to lower than in control pigs by 12 days post-challenge.

E. Isolation of Chimeric PRRS Viruses. Viremia was evaluated from serum samples by a quantitative real-time PCR amplification. Two combinations of chimeric PRRS virues, PRRSPTK-3/ptkPRRS and PRRSPTK-3/PRRSPTK-6, were used to inoculate 8 pigs, respectively. As shown in Table 2, all pigs were sero-negative at day 0 and all sero-positive at day 14 post-vaccination, indicating that chimeric PRRSV strains remain the replicative feature of modified-live attenuated PRRSV. At day 42 post-vaccination, all pig became sero-negative. These results showed that the tested chimeric PRRS viruses were able to remain the replication ability and a limited viremic duration.

TABLE 2

Virimia in host animals by chimeric strains.

| Group of pigs by vaccination strains | # of Animals | Viremia | | | |
|---|---|---|---|---|---|
| | | Week 0 | Week 2 | Week 4 | Week 6 |
| PRRSPTK-3/ptkPRRS | 5 | 0/8 | 8/8 | 7/8 | 0/8 |
| PRRSPTK-3/PRRSPTK-6 | 8 | 0/8 | 8/8 | 3/8 | 0/8 |
| Negative Control | 5 | 0/5 | 0/5 | 0/5 | 0/5 |

While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application.

Thus, the invention provides, among other things, an avirulent chimera of PRRSV and a method of its production. Various features and advantages of the invention are set forth in the following claims.

What is claimed is:

1. A method of producing a chimeric PRRSV virus comprising:
   a) transfecting a cell with a replicon comprising a 5' sequence derived from ptkPRRS (SEQ ID NO: 1) or a degenerate variant of ptkPRRS, the 5' sequence comprising ORF1, ORF2, part of ORF3 or a combination thereof, and a 3' sequence derived from a virulent strain of PRRSV;
   b) incubating the cell under conditions suitable for production of an infectious virus particle; and
   c) recovering the virus particle, wherein the recovered virus is attenuated relative to the virulent strain of PRRSV.

2. A method of producing a chimeric PRRSV virus comprising:
   a) transfecting a cell with a replicon comprising a 5' sequence derived from ptkPRRS-1 (SEQ ID NO: 2) or degenerate variant of ptkPRRS-1, the 5' sequence comprising ORF1, ORF2, part of ORF3 or a combination thereof, and a 3' sequence derived from a virulent strain of PRRSV;
   b) incubating the cell under conditions suitable for production of an infectious virus particle; and
   c) recovering the virus particle, wherein the recovered virus is attenuated relative to the virulent strain of PRRSV.

3. A method of producing a chimeric PRRSV virus comprising:
   a) transfecting a cell with a chimeric sequence comprising SEQ ID NO: 13 (pPRRSPTK-3) or a degenerate variant of SEQ ID NO: 13;
   b) incubating the cell under conditions suitable for production of an infectious, chimeric virus particle; and
   c) recovering the chimeric virus particle.

4. A method of producing a chimeric PRRSV virus comprising:
   a) transfecting a cell with a chimeric sequence comprising SEQ ID NO: 14 (pPRRSPTK-6) or a degenerate variant of SEQ ID NO: 14;
   b) incubating the cell under conditions suitable for production of an infectious, chimeric virus particle; and
   c) recovering the virus particle.

5. The method of claim 3 or 4, wherein the chimeric PRRSV virus demonstrates reduced virulence when compared to PRRSV strain NADC-20 or PRRSV strain MN-84.

* * * * *

SEQUENCE LISTING

<160> NUMBER OF SEQ ID NOS: 17

<210> SEQ ID NO 1
<211> LENGTH: 15543
<212> TYPE: DNA
<213> ORGANISM: Porcine reproductive and respiratory syndrome virus
      clone ptkPRRS

<400> SEQUENCE: 1

```
tatgacgtat aggtgttggc tctatgcctt gacatttgta ttgtcaggag ctgtgatcat      60
tgacacagcc caaagcttgc tgcacagaaa caccttctg tgacagcctc cttcaggga     120 gtttagggg ctgtccctag caccttgctt ccggagttgc actgctttac ggtctctcca    180
ccccttaaac catgtctggg atacttgatc ggtgcacgtg tacccccaat gccagggtgt    240
tcatggcgga gggccaagtc tactgcacac gatgcctcag tgcacggtct ctccttcctc    300
tgaatctcca agttcctgaa ctcggggtgc tgggcctatt ctataggccc gaagagccac    360
tccggtggac gttgccacgt gcattcccca ctgttgagtg ctccccccgcc ggagcctgct    420 ggctttctgc catcttcca attgcacgaa tgaccagtgg aaatctgaac tttcaacaaa    480
gaatggtgcg gtcgcagct gagctttaca gagccggcca gctcacccct gcagtcttga    540
agactctaca agtttatgaa cggggttgcc actggtaccc cattgttgga cctgttcctg    600
gagtggccgt ttatgccaac tccctacatg tgagtgataa accttcccg ggagcaactc    660 acgtgttaac caacctgccg ctcccgcaga gacccaagcc tgatgatttt tgcccctttg    720
agtgtgctat ggctactgtc tatgacattg gtcatgacgc cgtcatgtat gtggccgaag    780
agaaagtctc ctgggcccct cgtggcgggg atgaagtgaa attcgaacct gtccccgggg    840
agttgaagtt gattgcgaac cgactccgca cctccttccc gccccaccac gcagtggaca    900
tgtctaagtt caccttcaca gcccctgggc gtggtgtttc tatgcgggtc gaacgccaac    960
acggctgcct ccccgctgac acagttcctg aaggcaactg ctggtggagc ttgttcaact   1020
tgctcccact ggaagttcag aacaaagaaa ttcgtcatgc cggccaattt ggctaccaga   1080
ctaagcatgg tgtctctggc aagtacctac agcggaggct gcaagttaat ggtcttcgag   1140
cagtaactga cctaaatgga cctatcgtcg tacagtgctt ctccgttaag gagagttgga   1200
tccgccactt gaaactggcg gaagaaccca gctaccctgg gtttgaggac ctcctcagaa   1260
taagggttga gccaacacg tcgccattgg ctgacaagga tgaaaaaatt ttccggtttg   1320
gcaatcacaa gtggtatggc gctggaaaga gagcaaggaa agcacgctct agtgcgactg   1380
ctacagtcgc tggccgcgct ttgcccgttc gtgaaacccg gcaggtcgag gagcacgagg   1440
ttgccggcgc caacaaggct gagcacctca acactactc cccgcctgcc gaagggaatt   1500
gtggttggca ctgcatttcc gccatcggca accggatgtt gaattccaaa tttgaaacca   1560
cccttcccga aagagtgaga cctccagatg actgggctac tgatgaggat cttgtgaatg   1620
ccatccaaat cctcagactc cctgcggcct tggacaggaa cggtgcttgt gctagcgcca   1680
agtacgtact taagctggaa ggtgagcatt ggactgtcac tgtgacccct gggatgtccc   1740
cttctttgct ccctcttgaa tgtgttcagg gctgttgcga gcataagggc ggtcttggtt   1800
ccccagatgc agtcgaggtt tcggatttg accctgcctg ccttgactgg ctggctgagg   1860
tgatgcactt gccctagcaat gccatcccag ccgctctggc cgaaatgtcc ggcgattcca   1920
atcgtccggc ttccccggtc accaccgtgt ggactgtttt gcagttctta gcccgccaca   1980
```

-continued

```
acggagggaa tcaccctgac caaatacgct tagggaaaat tatcagcctt tgtcaggtga    2040
ttgaggactg ctgctgttcc cagaacaaaa ccaaccgggt caccccggag gaggtcgcag    2100
caaagattga cctgtacctc cgtggtgcaa caaatcttga agaatgcttg gccaggcttg    2160
agaaagcgcg cccgccacgc gtaatggaca cctcctttga ttgggatgtt gtgctccctg    2220
gggttgaggc ggcaactcaa acgaccgaac tgccccaagt caaccagtgt cgcgctctgg    2280
tccctgttgt gactcaaaag tccttggaca caactcggt ccctctgacc gccttttcac     2340
tggctaacta ctactaccgc gcgcaaggtg acgaagttcg tcaccgtgaa agactaacca    2400
ccgtgctctc taagttggaa ggggttgttc gagaagaata cgggctcatg ccaaccgggc    2460
ctggtccacg gcccacactg ccacgcgggc tcgacgaact caaggaccag atggaggtgg    2520
acttgctgaa actggctaac gcccagatga cttcggacat gatggcctgg gcagtcgagc    2580
aggttgacct aaagacttgg gtcaagaact atccgcggtg gacaccacca cctcctccgc    2640
caatagttca gcctcgaaaa acgaagcttg tcaagagctt accagagagc aagcctgttc    2700
ctgcaccgcg taggaaggtc aggtccgatt gtgactgccc cacccatcg ggcaacaatc     2760 ttcctgacag ttgggaagat ttggctgttg gttgccctc tgatctccct acctcacctg     2820
agccggtaac acctttgagt gagccggcat ctgtgtccgc accgcgacgc tcttttaggc    2880
cggtgaagcc tttgagtgaa ccagttccag tccctgcacc gcgcaagact gtgtcccgac    2940
cggcaacacc tctgagtgag ccgatccctg tgcccgcacc gcgacgcaag tttcagcagg    3000 tagaaaagt gaatccggcg gcggcaaccc tggcgtgcca agacgagttt ccagatttgt      3060
ctgcatcctc gcatactgaa tatgaggcgt ctccccttgt actaccgcag aacggggacg    3120
ttcttgaagt ggaggagcgg gaagctgagg aaatcctgag tggaatctca gacatactgg    3180
atgccatcaa accggcatct gcatcatcaa gcagctccct gtcaagtgtg gcgatcacac    3240
gcccgaaata ctcagctcaa gccatcattg actcgggtgg gccctacagc gggcatctcc    3300
aagaggtgaa ggaaacatgc ctaagcatca tgagtgaggc atgtgatgtg accaagcttg    3360
atgaccctgc cacgcaggaa tggctttctc gcatgtggga tagggtggac atgctgactt    3420
ggcgcaatac gtctgttcac caggcgtctc gcaccttgga cgacagattt aagtttctcc    3480
cgaagatgat acttgaaaca ccgccgcccct accgtgtgg gttcgtgatg atgcctcgca    3540
cacctgcacc ctccgtgggt gcggagagcg acctcactat tggctcagtc gctactgagg    3600
acgttccacg catcttcggg aaagtaaatg atgtctgcaa gatgatcgac cagagaccct    3660
tggtactctt tgaaaatgag ctggcagatg accaacctgc cagagatcct cggacatcat    3720
cgcagaggtt tgacgggagc acaccagctc cgcccgcagg cacggatggc accggtttgg    3780
cttcgggccc tggagtgaga gaagtggatt catgtgaggc gagctcaacc gagaaaaatg    3840
aacagccctt cgtgttgaac ggcggcgcca gcacacaggc gtcaacgttt accaatttgc    3900
cgcctccagg cggtatagat gcgggcggga gtgggccgtt acaaacggtg cgaaagaagg    3960
ctgaacggtt ctttgaccta ctaagccgtc aggttttaa tctcgtctcc catctccctg     4020
ttttcttctc acgccttttc aaacctggcg gtgactattc tccgggtgat tgggggttttg   4080 cagcttttac tttattgtgc ctcttttgt gttacagtta cccggccttt ggtgctgttc     4140
ccctcttggg tgtattttct gggtcttctc ggcgtgttcg aatgggggtt tttggctgct    4200
ggttggcttt tgctgttagt ctgttcaaac ctgtgtccga cccagtcggc gctgcttgtg    4260
aatttgattc gccagagtgt agaaacatcc ttcattcttt tgagcttctc aaaccttggg    4320
accctgttcg cggccttgtt gtgggccccg tcggtctcag tcttgccatt tttggcaggt    4380
```

```
tattgggcgg ggcacgccac atctggcact ttttgcttag gtttggcatt gttgcagatt   4440
gtatcttggc tggagcttat gtgctttctc aaggcaggtg taaaaagtgc tggggatctt   4500
gtataagaac tgctcctaat gaggtcgcct ttaacgtgtt tccttttaca cgtgcgacca   4560
ggtcgtcact tatcgacctg tgcaatcggt tttgcgcgcc aaaaggtatg gaccccattt   4620
tcctcgccac tgggtggcgc gggtgctgga ccggccgaag ccccattgag caaccctctg   4680
aaaaacccat cgcgtttgcc cagttggatg aaaaaaagat tacggctagg actgtggtcg   4740
cccagcccta tgaccccaac caagctgtaa agtgcttgcg ggtattgcag gcgggcgggg   4800
tgatggtggc tgaggcagtc ccaaaagtgg tcaaagtttc tgctgttcca ttccgagccc   4860
ccttctttcc caccggagtg aaagttgatc ctgaatgcag gattgtggtt gaccccgaca   4920 cttttcactgc agccctccga tctggctact ccaccacaaa cctcgtcctt ggtgtggggg   4980
actttgccca gctgaatgga ttaaaaatca ggcaaatttc caagccttca gggggaggtc   5040
cacacctcat ggctgccctg catgttgctt gctctatggc tctgcacatg cttgttggga   5100
tttatgtgac tgctgtgggt tcttgcggca ccggcactaa cgatccgtgg tgcgccaacc   5160
cgtttgccgt ccctggctac ggacctggct ctctctgcac gtccagattg tgcatctccc   5220
aacatggcct tacccctaccc ttgacagcac ttgtggcggg attcggcttt caggaaattg   5280
ccttggttat tttgattttt gtttctatcg gaggcatggc tcatagattg agttgcaagg   5340
ctgatatgct gtgtattttg tttgcaatcg ccagctatgt ttgggtacct cttacctggt   5400
tgctttgtgt gtttccttgc tggttgcgct gttttttcgtt gcaccccctc accatcctat   5460
ggttggtgtt tttcctgatt tctgtaaata tgccttcagg aatcttggcc ttggtgttgt   5520
tgatttctct ctggcttctt ggtcgttata ccaacgttgc cggtcttgtc actcccctatg   5580 acattcatca ttacaccagt ggccccccgcg tgttgccgc cttggctacc gcaccagatg   5640
ggacctactt ggccgctgtc cgccgcgccg cgttgactgg tcgcaccatg ctgtttaccc   5700
cgtctcagct cgggtccctt cttgagggcg cttttcagaac tcgaaagccc tcactgaaca   5760
ccgttaatgt ggtcgggtcc tccatgggct ctggcgggt gttcaccatc gacgggaaaa   5820
ttaagtgcgt aactgctgca catgtcctta cgggtaattc agctagggtt tccggggttg   5880
gcttcaatca aatgcttgac ttcgatgtga aaggagactt cgccatagcc gattgcccag   5940
actggcaagg ggctgctccc aagacccaat tctgcgagga aggatggact ggccgggcct   6000
attggctaac gtcttctggt gtcgaacccg gcgtcattgg aaaaggattc gccttctgct   6060
tcaccgcgtg cggcgattcc ggatccccag taatcaccga ggccggcgag cttatcggcg   6120
ttcacacggt gtcaaataaa caaggaggag gcatcgtcac gcgcccctca ggccagtttt   6180
gtagtgtggc acccgtcaaa ttaagcgaac taagtgaatt ctttgcaggg cctaaggtcc   6240
cgctcggtga tgtgaaagtt ggcagccaca taattgaaga cgtaggcgag gtgccttcag   6300
atctttgcgc cttgcttgct gccaaacctg aactggaagg aggcctctcc accgttcaac   6360
ttctgtgtgt gttttttcctc ctgtgggagaa tgatgggaca tgcctggacg cccttggttg   6420
ccgtagggtt ttttatcttg aatgaggtcc tcccagctgt cctggtccgg agtgtttttct   6480 cctttggaat gtttgtgcta tcctggctca ccatggtc tgcgcaagtt ctgatgatca   6540
ggcttctaac agcagctctt aacaggaata gatggtcact tgccttttac agcctcggtg   6600
caatgactgg ttttgtcgca gatctcgcgg ctactcaggg gtatccgttg caggcagtga   6660
tgagtttgag cacttatgca ttcctgcctc ggataatggt tgtgacttca ccagtcccag   6720
```

```
tggttgcgtg tggtgttgtg cacctacttg ccatcatttt gtacttgttt aagtaccgct   6780
gcctgcacaa catccttgtt ggcgatggag tgttctctgc ggctttcttc ctgcgatatt   6840
ttgccgaggg aaagttgagg gaggggtgt cgcaatcctg cgggatgaat catgagtcac    6900
ttaccggtgc cctcgctatg agactcaatg acgaggactt ggatttcctc acgaaatgga   6960
ctgatttcaa gtgctttgtt tctgcgtcca acatgagaaa tgctgcgggc caattcatcg   7020
aggctgccta tgctaaagca cttagagtag aacttgccca gttggtgcag gttgataagg   7080
ttcggggtac tttggccaaa cttgaagctt ttgccgacac cgtggcaccc caactctcgc   7140
ccggtgacat tgttgtcgct cttggccata cgcctgttgg cagtatcttc gacctgaagg   7200
ttggtaacac caagcacact ctccaagcca tcgagaccag ggtccttgct gggtccaaaa   7260
tgaccgtggc gcgcgtcgtc gatccgaccc ccacgccccc acccgcaccc gtgcccatcc   7320
ccctcccacc gaaggttttg gagaacggtc caaacgcttg gggggatgaa gaccgtttga   7380
ataaaagag gaggcgcagg atggaagccc tcggcatcta tgttatgggc gggaaaaagt    7440
accagaaatt ttgggacaag aattccggtg acgtgtttta tgaggaggtc ataacaaca    7500
cagatgagtg ggagtgcctc agagttggcg accctgccga cttttgaccct gagaagggaa   7560
ctttgtgtgg gcatgtcacc attgaagata gggcttacca tgtttacacc tccccatctg   7620
gtaagaaatt cctagtcccc gtcaacccag agaacggaag agttcaatgg gaggctgcaa   7680
agctttccgt tgagcaggcc cttggtatga tgaacgtcga cggcgagctg actgccaagg   7740
aactggagaa actgaaaaga ataattgaca aactccaggg cctgactaag gagcagtgtt   7800
taaactgcta gccgccagcg acttgacccg ctgtggtcgc ggcggcttgg ttgttactga   7860
aacagcggta aaaatagtca aatttcacaa ccggaccttc accctgggac ctgtgaattt   7920
aaaagtggcc agtgaggttg agctaaaaga cgcggttgag cacaaccaac accggttgc    7980
gagaccgatc gatggtggag ttgtgctcct gcgttccgcg gttccttcgc ttatagacgt   8040
cttgatctcc ggtgctgatg catctcccaa gttacttgcc catcacgggc cgggaaacac   8100
tgggatcgat ggcacgctct gggattttga gtccgaagcc actaaagagg aagtcgcact   8160
cagtgcgcaa ataatacagg cttgtgacat taggcgcggc gacgctcctg aaattggtct   8220
cccttacaag ctgtaccctg ttaggggtaa ccctgagcgg gtgaaaggag ttctgcagaa   8280
tacaaggttt ggagacatac cttacaaaac ccccagtgac actggaagcc cagtgcacgc   8340
ggctgcctgc cttacgccca cgccactcc ggtgactgat gggcgctccg tcttggccac    8400
gaccatgccc cccgggtttg agttatatgt accgaccata ccagcgtctg tccttgatta   8460
ccttgactct aggcctgact gccctaaaca gctgacagag cacggctgcg aagatgccgc   8520
actgaaagac ctctctaaat atgacttgtc cacccaaggc tttgttttac ctggagttct   8580
tcgccttgtg cggaaatacc tgtttgccca tgtaggtaag tgcccacccg ttcatcggcc   8640
ttctacttac cctgctaaga attctatggc tggaataaat gggaacaggt tcccaaccaa   8700
ggacattcag agcgtccctg aaatcgacgt tctgtgcgca caggctgtgc gagaaaactg   8760
gcaaactgtc accccttgta ctcttaagaa acagtattgc gggaagaaga agactaggac   8820
catactcggc accaataact tcatcgcact agcccaccga gcagtgttga gtggtgttac   8880
ccagggcttc atgaaaaagg cgtttaactc gcccatcgcc ctcggaaaga acaagtttaa   8940
ggagctacag actccggtcc tgggcaggtg ccttgaagct gatctcgcat cctgcgatcg   9000
atccacgcct gcaattgtcc gctggtttgc cgccaacctt ctttatgaac ttgcctgtgc   9060
tgaagagcat ctaccgtcgt acgtgctgaa ctgctgccac gacttactgg tcacgcagtc   9120
```

```
cggcgcagtg actaagagag gtggcctgtc gtctggcgac ccgatcacct ctgtgtctaa    9180
caccatttat agtttggtga tctatgcaca gcatatggtg cttagttact tcaaaagtgg    9240
tcacccccat ggccttctgt tcttacaaga ccagctaaag tttgaggaca tgctcaaggt    9300
tcaacccctg atcgtctatt cggacgacct cgtgctgtat gccgagtctc ccaccatgcc    9360
aaactatcac tggtgggttg aacatctgaa tttgatgctg gggtttcaga cggacccaaa    9420
gaagacagca ttaacagact cgccatcatt tctaggctgt agaataataa atgggcgcca    9480
gctagtcccc aaccgtgaca ggatcctcgc ggccctcgcc tatcacatga aggcgagtaa    9540
tgtttctgaa tactatgcct cagcggctgc aatactcatg acagctgtg cttgtttgga    9600
gtatgatact gaatggtttg aagaacttgt agttggaata gcgcagtgcg cccgcaagga    9660
cggctacagc tttcccggca cgccgttctt catgtccatg tgggaaaaac tcaggtccaa    9720
ttatgagggg aagaagtcga gagtgtgcgg gtactgcggg gccccggccc cgtacgctac    9780
tgcctgtggc ctcgacgtct gcatttacca caccccacttc caccagcatt gtccagtcac    9840
aatctggtgt ggccatccag cggggttctgg ttcttgtagt gagtgcaaat cccctgtagg    9900
gaaaggcaca agccctttag acggagtgtt ggaacaagtc ccgtataagc ccccacggac    9960
cgttatcatg catgtggagc agggtctcac cccccttgat ccaggtagat accaaactcg   10020
ccgcggatta gtctctgtca ggcgtggaat taggggaaat gaagttgaac taccagacgg   10080
tgattatgct agcaccgcct tgctccctac ctgcaaagag atcaacatgg tcgctgtcgc   10140
ttccaacgta ttgcgcagca ggttcatcat cggcccaccc ggtgctggga aaacatactg   10200
gctccttcaa caggtccagg atggtgatgt tatttacaca ccaactcacc agaccatgct   10260
tgacatgatt agggctttgg ggacgtgccg gttcaacgtc ccggcaggca aacgctgca    10320
attccccgtc ccctcccgca ccggtccgtg ggttcgcatc ctagccggcg gttggtgtcc   10380
tggcaagaat tccttcctag atgaagcagc gtattgcaat caccttgatg ttttgaggct   10440
tcttagtaaa actaccctca cctgtctagg agacttcaag caactccacc cagtgggttt   10500
tgattctcat tgctatgttt ttgacatcat gcctcaaact caactgaaga ccatctggag   10560
gtttggacag aatatctgtg atgccattca gccagattac agggacaaac tcatgtccat   10620
ggtcaacaca cccgtgtga cctacgtgga aaaacctgtc aggtatgggc aggtcctcac    10680
cccctaccac agggaccgag aggacgacgc catcactatt gactccagtc aaggcgccac   10740
attcgatgtg gttacattgc atttgcccac taaagattca ctcaacaggc aaagagccct   10800
tgttgctatc accagggcaa gacacgctat cttttgtgtat gacccacaca ggcagctgca   10860
gggcttgttt gatcttcctg caaaaggcac acccgtcaac ctcgcagtgc accgcgacgg   10920
gcagctgatc gtgctggata gaaataacaa agaatgcacg gttgctcagg ctctaggcaa   10980
cggggataaa tttagggcca cagacaagcg tgttgtagat tctctccgcg ccatttgtgc   11040
tgatctagaa gggtcgagct ctccgctccc caaggtcgca cacaacttgg gatttattt    11100
ctcacctgat ttaacacagt ttgctaaact cccagtagaa cttgcacctc actggccgt    11160
ggtgacaacc cagaacaatg aaaagtggcc agatcggctg gttgccagcc ttcgccctat   11220
ccataaatac agccgcgcgt gcatcggtgc cggctatatg gtgggcccctt cggtgttcct  11280
aggcactcct ggggtcgtgt catactatct cacaaaattt gttaagggcg aggctcaagt   11340
gcttccggag acggttttca gcaccggccg aattgaggta gactgccggg aatatcttga   11400
tgatcgggag cgagaagttg ctgcgtccct cccacacgct ttcattggcg acgtcaaagg   11460
```

```
cactaccgtt ggaggatgtc atcatgtcac ctccagatac ctcccgcgcg tccttcccaa    11520
ggaatcagtt gcggtagtcg gggtttcaag ccccggaaaa gccgcgaaag cattgtgcac    11580
actgacagat gtgtacctcc cagatcttga agcctatctc cacccggaga cccagtccaa    11640
gtgctggaaa atgatgttgg acttcaaaga agttcgacta atggtctgga aagacaaaac    11700
agcctatttc caacttgaag gtcgctattt cacctggtat cagcttgcca gctatgcctc    11760
gtacatccgt gttcctgtca actctacggt gtacttggac ccctgcatgg gccccgccct    11820
ttgcaacagg agagtcgtcg ggtccaccca ctgggggct gacctcgcgg tcaccccta     11880 tgattacggc gctaaaatta tcctgtctag cgcgtaccat ggtgaaatgc cccccggata    11940
caaaattctg gcgtgcgcgg agttctcgtt ggatgaccca gttaagtaca aacatacctg    12000
ggggtttgaa tcgatacag cgtatctgta tgagttcacc ggaaacggtg aggactggga     12060
ggattacaat gatgcgtttc gtgcgcgcca ggaagggaaa atttataagg ccactgccac    12120
cagcwtgaag ttttatttc ccccgggccc tgtcattgaa ccaactttag gcctgaattg     12180
aaatgaaatg gggtccatgc aaagcctttt tgacaaaatt ggtcaacttt ttgtggatgc    12240
tttcacggaa ttcttggtgt ccattgttga tatcatcata tttttggcca ttttgtttgg    12300
cttcaccgtc gccggttggc tggtggtctt ttgcatcaga ttggtttgct ccgcgatact    12360
ccgtgcacgc cctgcctttc actctgagca gttacagaag atcctatgag gcctttcttt    12420
ccctgtgtca ggtggacatt cccacctggg gaatcaaaca tcctctgggg gtgctttggc    12480
accataaggt gtcaaccctg attgatgaaa tggtgtcgcg tcgaatgtac cgcatcatgg    12540
aaaaagcagg acaggctgcc tggaaacagg tggtgagcga ggccacgctg tctcgcatta    12600
gtagtttgga tgtggtggct cattttcaac atcttgccgc cgttgaagcc gagacctgta    12660
aatatttggc ctctcggcta cccatgctac acaacctgcg catgacgggg tcaaatgtaa    12720
ccatagtata taatggtact ttgaatcagg tgtttgccat tttcccgacc cctggttccc    12780
ggccaaagct tcatgatttt cagcaatggc tgatagctgt gcattcgtcc atattttcct    12840
ctgttgcagc ttcttgtact ctgtttgttg tactgtggtt gcgggtccca atgctacgta    12900 ctgttttttgg tttccgctgg ttaggggcaa ttttttcctttc gagctcttgg tgaattacac    12960
ggtgtgccca ccttgcctca cccggcaagc agccgcacag cgctacgaac ctggcaaggc    13020
tctttggtgc agaattgggt acgatcgatg tgaggaggac gatcacgacg agctagggtt    13080
cgtgataccg tctggcctct ccagcgaagg ccactagtct agtgtttacg cctggttggc    13140 gttttttgtcc ttcagttaca cggcccagtt tcatcctgag atattcggga tagggaatgt    13200
gagcaaagtc tatgttgaca tcaaacacca attcatctgc gctgttcatg atgggcagaa    13260
caccaccttg ccccgccatg acaactttc agccgtgttt cagacctatt accagcatca    13320
agtcgacggc ggcaattggt ttcacctaga atggctgcgt cccttctttt cctcttggtt    13380
ggttttaaat gtctcgtggt ttctcaggcg tttgcctgca agccatgttt cagttcgagt    13440
ctttcagaca ttaagaccaa caccaccgca gcagcgggct tgctgtcct ccaggacatc     13500 agctgcctta ggcatggcga tccgtcctct gcggcgattc gcaaaagctc tcagtgccgc    13560
acggcgatag ggacacccgt gtatatcacc attacagcca atgtgacaga tgagaattat    13620
ttacactcct ctgatctcct catgctttct tcttgccttt tctatgcttc tgagatgagt    13680
gaaaagggat ttaaggtggt atttggcaat gtgtcaggca tcgtggctgt gtgtgttaat    13740
tttaccagct acgtccaaca tgtcagggac ttcacccaac gctccttggt ggtcgatcat    13800
gtgcggctgc tccatttcat gacacctgag gccatgaggt gggcaactgt tttagcctgt    13860
```

```
cttttttgcca ttctgttggc agtttgaatg tttaagtatg ttggggaaat gcttgaccgc    13920 ggggttgctgc tcgcgattgc tttctttttg gtgtatcgtg ccgttctgtt ttgctgtgct    13980
cgtcaacgcc agctacagca gcagctctca tttacagttg atttataact tgacgctatg    14040
tgagctgaat ggtacagatt ggctggctaa taaatttgat tgggcagcgg agagttttgt    14100
catctttcct gtgttgaccc acatcgtttc ctatggtgca ctaaccacca gccacttcct    14160
tgacacagtt ggtctggtta ctgtgtctac cgccgggttt tatcatgggc ggtatgtcct    14220
gagtagcatc tacgcggtct gtgccctggg ctgcttaatt tgcttcgtca ttaggttggc    14280
caataactgt atgtcctggc gctactcatg cacaagatac accaacttttc ttctggacac    14340 taagggcaga ctctatcgtt ggcggtcgcc tgtcatcata gagaaagggg gtaaggtaga    14400
ggtcgaaggc catctgatcg acctcaaaag agttgtgctt gatggttccg cggcaacccc    14460
tttaaccaga gtttcagcgg aacaatgggg tcgtccctag acgacttttg tcatgacagc    14520
acggctccac agaaggtgct cttggcgttt tctattactt acacgccagt gatgatatat    14580
gccctaaagg taagtcgcgg ccgattgctg gggcttctgc accttctgat cttcctgaat    14640
tgtgctttca ccttcgggta tatgacattc gcgcactttc agagtacaaa tagggtcgcg    14700
ctcactatgg gagcagtagt tgcactcctt tggggggtgt actcagccat agaaacttgg    14760
aggttcatca cctctagatg ccgtttgtgc ttgttaggcc gcaggtacat tctgcccct    14820 gcccaccacg ttgaaagtgc cgcaggcttt catccgatta cggcaaatga taaccacgca    14880
tttgtcgtcc ggcgtcccgg ctccactacg gttaacggca cattggtgcc cgggttgaag    14940
agcctcgtgt tgggtggcag aaaagctgta aaacggggag tggttaacct tgttaaatat    15000
gccaaataac aacggcaaac agcagaagaa aaagaagggg gatggccagc cagtcaatca    15060
gctgtgccag atgctgggta agatcatcgc ccagcaaaac cagtccagag gtaagggacc    15120
gggaaagaaa aacaagaaga aaaacccgga gaagcccat tttcctctgg cgactgaata    15180
tgacgtcaga caccacttta cccctagtga gcggcaattg tgcctgtcgt caatacagac    15240
tgcctttaat caaggcgctg gtacttgcac cctgtccgat tcaggagga taagttacac    15300 tgtggagttt agtttgccca cgcatcatac tgtgcgcctg attcgcgtca cagcatcacc    15360
ctcagcatga tgggctggca ttcttgaggc atctcagtgt ttgaattgga agaatgtgtg    15420
gtgaatggca ctgattgata ttgtgcctct aagtcaccta ttcaattagg gcgaccgtgt    15480
gggggtaaga tttaattggc gaaaccatg cggccgaaat taaaaaaaaa aaaaaaaaa    15540 aaa                                                                   15543

<210> SEQ ID NO 2
<211> LENGTH: 15564
<212> TYPE: DNA
<213> ORGANISM: Porcine reproductive and respiratory syndrome virus
      clone ptkPRRS-1

<400> SEQUENCE: 2
tatgacgtat aggtgttggc tctatgcctt gacatttgta ttgtcaggag ctgtgatcat      60
tgacacagcc caaagcttgc tgcacagaaa caccctttctg tgacagcctc cttcagggga    120
gtttaggggt ctgtccctag caccttgctt ccggagttgc actgctttac ggtctctcca    180
cccctttaac catgtctggg atacttgatc ggtgcacgtg taccccaat gccagggtgt      240 tcatggcgga gggccaagtc tactgcacac gatgcctcag tgcacggtct ctccttcctc    300
tgaatctcca agttcctgaa ctcggggtgc tgggcctatt ctataggccc gaagagccac    360
```

```
tccggtggac gttgccacgt gcattcccca ctgttgagtg ctcccccgcc ggagcctgct    420
ggctttctgc catcttttcca attgcacgaa tgaccagtgg aaatctgaac tttcaacaaa    480
gaatggtgcg gtcgcagct gagctttaca gagccggcca gctcacccct gcagtcttga     540
agactctaca agtttatgaa cggggttgcc actggtaccc cattgttgga cctgttcctg    600
gagtggccgt ttatgccaac tccctacatg tgagtgataa acctttcccg ggagcaactc    660
acgtgttaac caacctgccg ctcccgcaga gacccaagcc tgatgatttt tgccccttg    720
agtgtgctat ggctactgtc tatgacattg gtcatgacgc cgtcatgtat gtggccgaag   780
agaaagtctc ctgggcccct cgtggcgggg atgaagtgaa attcgaacct gtccccgggg   840
agttgaagtt gattgcgaac cgactccgca cctccttccc gccccaccac gcagtggaca    900
tgtctaagtt caccttcaca gcccctgggc gtggtgtttc tatgcgggtc gaacgccaac   960
acggctgcct ccccgctgac acagttcctg aaggcaactg ctggtggagc ttgttcaact   1020
tgctcccact ggaagttcag aacaaagaaa ttcgtcatgc cggccaattt ggctaccaga   1080
ctaagcatgg tgtctctggc aagtacctac agcggaggct gcaagttaat ggtcttcgag    1140
cagtaactga cctaaatgga cctatcgtcg tacagtgctt ctccgttaag gagagttgga    1200
tccgccactt gaaactggcg gaagaaccca gctaccctgg gtttgaggac ctcctcagaa    1260
taagggttga gcccaacacg tcgccattgg ctgacaagga tgaaaaaatt ttccggtttg    1320
gcaatcacaa gtggtatggc gctggaaaga gagcaaggaa agcacgctct agtgcgactg    1380
ctacagtcgc tggccgcgct ttgcccgttc gtgaaacccg gcaggtcgag gagcacgagg    1440
ttgccggcgc caacaaggct gagcacctca acactactc cccgcctgcc gaagggaatt    1500
gtggttggca ctgcatttcc gccatcggca accggatgtt gaattccaaa tttgaaacca    1560
cccttcccga aagagtgaga cctccagatg actgggctac tgatgaggat cttgtgaatg    1620
ccatccaaat cctcagactc cctgcggcct tggacaggaa cggtgcttgt gctagcgcca    1680
agtacgtact taagctggaa ggtgagcatt ggactgtcac tgtgaccct gggatgtccc     1740
cttctttgct ccctcttgaa tgtgttcagg ctgttgcga gcataagggc ggtcttggtt     1800
ccccagatgc agtcgaggtt ttcggatttg accctgcctg ccttgactgg ctggctgagg    1860
tgatgcactt gcctagcaat gccatcccag ccgctctggc cgaaatgtcc ggcgattcca    1920
atcgtccggc ttccccggtc accaccgtgt ggactgtttc gcagttctta gcccgccaca    1980
acggagggaa tcaccctgac caaatacgct tagggaaaat tatcagcctt tgtcaggtga    2040
ttgaggactg ctgctgttcc cagaacaaaa ccaaccgggt cacccggag gaggtcgcag     2100
caaagattga cctgtacctc cgtggtgcaa caaatcttga agaatgcttg gccaggcttg    2160
agaaagcgcg cccgccacgc gtaatggaca cctcctttga ttgggatgtt gtgctccctg    2220
gggttgaggc ggcaactcaa cgaccgaac tgccccaagt caaccagtgt cgcgctctgg     2280
tccctgttgt gactcaaaag tccttggaca caactcggt ccctctgacc gccttttcac     2340
tggctaacta ctactaccgc gcgcaaggtg acgaagttcg tcaccgtgaa agactaacca    2400
ccgtgctctc taagttggaa ggggttgttc gagaagaata cgggctcatg ccaaccgggc    2460
ctggtccacg gccacactg ccacgcgggc tcgacgaact caaggaccag atggaggtgg     2520
acttgctgaa actggctaac gcccagatga cttcggacat gatggcctgg gcagtcgagc    2580
aggttgacct aaagacttgg gtcaagaact atcgcggtg gacaccacca cctcctccgc     2640
caatagttca gcctcgaaaa acgaagcttg tcaagagctt accagagagc aagcctgttc    2700
```

```
ctgcaccgcg taggaaggtc aggtccgatt gtgactgccc caccctatcg ggcaacaatc    2760
ttcctgacag ttgggaagat ttggctgttg gttgcccctc tgatctccct acctcacctg    2820
agccggtaac acctttgagt gagccggcat ctgtgtccgc accgcgacgc tcttttaggc    2880
cggtgaagcc tttgagtgaa ccagttccag tccctgcacc gcgcaagact gtgtcccgac    2940
cggcaacacc tctgagtgag ccgatccctg tgcccgcacc gcgacgcaag tttcagcagg    3000
tagaaaaagt gaatccggcg gcggcaaccc tggcgtgcca agacgagttt ccagatttgt    3060
ctgcatcctc gcatactgaa tatgaggcgt ctccccttgt actaccgcag aacggggacg    3120
ttcttgaagt ggaggagcgg gaagctgagg aaatcctgag tggaatctca gacatactgg    3180
atgccatcaa accggcatct gcatcatcaa gcagctccct gtcaagtgtg gcgatcacac    3240
gcccgaaata ctcagctcaa gccatcattg actcgggtgg gccctacagc gggcatctcc    3300
aagaggtgaa ggaaacatgc ctaagcatca tgagtgaggc atgtgatgtg accaagcttg    3360
atgaccctgc cacgcaggaa tggctttctc gcatgtggga tagggtggac atgctgactt    3420
ggcgcaatac gtctgttcac caggcgtctc gcaccttgga cgacagattt aagtttctcc    3480
cgaagatgat acttgaaaca ccgccgcccc accgtgtgg gttcgtgatg atgcctcgca    3540
cacctgcacc ctccgtgggt gcggagagcg acctcactat tggctcagtc gctactgagg    3600
acgttccacg catcttcggg aaagtaaatg atgtctgcaa gatgatcgac cagagaccct    3660
tggtactctt tgaaaatgag ctggcagatg accaacctgc cagagatcct cggacatcat    3720
cgcagaggtt tgacgggagc acaccagctc cgcccgcagg cacggatggc accggtttgg    3780
cttcgggccc tggagtgaga gaagtggatt catgtgaggc gagctcaacc gagaaaaatg    3840
aacagcccct cgtgttgaac ggcggcgcca gcacacaggc gtcaacgttt accaatttgc    3900
cgcctccagg cggtatagat gcgggcggga gtgggccgtt acaaacggtg cgaaagaagg    3960
ctgaacggtt ctttgaccta ctaagccgtc aggtttttaa tctcgtctcc catctccctg    4020
ttttcttctc acgcctttc aaacctggcg gtgactattc tccgggtgat tggggttttg    4080
cagcttttac tttattgtgc ctcttttgt gttacagtta cccggccttt ggtgctgttc    4140
ccctcttggg tgtattttct gggtcttctc ggcgtgttcg aatgggggtt tttggctgct    4200
ggttggcttt tgctgttagt ctgttcaaac ctgtgtccga cccagtcggc gctgcttgtg    4260
aatttgattc gccagagtgt agaaacatcc ttcattcttt tgagcttctc aaaccttggg    4320
accctgttcg cggccttgtt gtgggccccg tcggtctcag tcttgccatt tttggcaggt    4380
tattgggcgg ggcacgccac atctggcact ttttgcttag gtttggcatt gttgcagatt    4440
gtatcttggc tggagcttat gtgctttctc aaggcaggtg taaaaagtgc tggggatctt    4500
gtataagaac tgctcctaat gaggtcgcct ttaacgtgtt tccttttaca cgtgcgacca    4560
ggtcgtcact tatcgacctg tgcaatcggt tttgcgcgcc aaaaggtatg daccccattt    4620
tcctcgccac tgggtggcgc gggtgctgga ccggccgaag ccccattgag caaccctctg    4680
aaaaacccat cgcgtttgcc cagttggatg aaaaaaagat tacggctagg actgtggtcg    4740
cccagcccta tgaccccaac caagctgtaa agtgcttgcg ggtattgcag gcgggcgggg    4800
tgatggtggc tgaggcagtc ccaaaagtgg tcaaagtttc tgctgttcca ttccgagccc    4860
ccttctttcc caccggagtg aaagttgatc ctgaatgcag gattgtggtt gaccccgaca    4920
ctttcactgc agccctccga tctggctact ccaccacaaa cctcgtcctt ggtgtggggg    4980
actttgccca gctgaatgga ttaaaaaatca ggcaaatttc caagccttca ggggaggtc     5040 cacacctcat ggctgccctg catgttgctt gctctatggc tctgcacatg cttgttggga    5100
```

```
tttatgtgac tgctgtgggt tcttgcggca ccggcactaa cgatccgtgg tgcgccaacc    5160
cgtttgccgt ccctggctac ggacctggct ctctctgcac gtccagattg tgcatctccc    5220
aacatggcct tacccctaccc ttgacagcac ttgtggcggg attcggcttt caggaaattg   5280
ccttggttat tttgattttt gtttctatcg gaggcatggc tcatagattg agttgcaagg    5340
ctgatatgct gtgtattttg tttgcaatcg ccagctatgt ttgggtacct cttacctggt    5400
tgctttgtgt gtttccttgc tggttgcgct gtttttcgtt gcacccctc accatcctat     5460
ggttggtgtt tttcctgatt tctgtaaata tgccttcagg aatcttggcc ttggtgttgt    5520
tgatttctct ctggcttctt ggtcgttata ccaacgttgc cggtcttgtc actccctatg    5580
acattcatca ttacaccagt ggccccgcg tgttgccgc cttggctacc gcaccagatg     5640
ggacctactt ggccgctgtc cgccgcgccg cgttgactgg tcgcaccatg ctgtttaccc    5700
cgtctcagct cgggtccctt cttgagggcg ctttcagaac tcgaaagccc tcactgaaca    5760
ccgttaatgt ggtcgggtcc tccatgggct ctggcggggt gttcaccatc gacgggaaaa    5820
ttaagtgcgt aactgctgca catgtcctta cgggtaattc agctagggtt tccgggggttg   5880
gcttcaatca aatgcttgac ttcgatgtga aggagactt cgccatagcc gattgcccag    5940
actggcaagg ggctgctccc aagacccaat tctgcgagga aggatggact ggccgggcct    6000
attggctaac gtcttctggt gtcgaacccg gcgtcattgg aaaaggattc gccttctgct    6060
tcaccgcgtg cggcgattcc ggatcccag taatcaccga ggccggcgag cttatcggcg    6120
ttcacacggg gtcaaataaa caaggaggag gcatcgtcac gcgcccctca ggccagtttt    6180
gtagtgtggc acccgtcaaa ttaagcgaac taagtgaatt ctttgcaggg cctaaggtcc    6240
cgctcggtga tgtgaaagtt ggcagccaca taattgaaga cgtaggcgag gtgccttcag    6300
atctttgcgc cttgcttgct gccaaacctg aactggaagg aggcctctcc accgttcaac    6360
ttctgtgtgt gttttttcctc ctgtggagaa tgatgggaca tgcctggacg cccttggttg    6420
ccgtagggtt ttttatcttg aatgaggtcc tcccagctgt cctggtccgg agtgttttct    6480
cctttggaat gtttgtgcta tcctggctca caccatggtc tgcgcaagtt ctgatgatca    6540
ggcttctaac agcagctctt aacaggaata gatggtcact tgcctttac agcctcggtg    6600
caatgactgg ttttgtcgca gatctcgcgg ctactcaggg gtatccgttg caggcagtga    6660
tgagtttgag cacttatgca ttcctgcctc ggataatggt tgtgacttca ccagtcccag    6720
tggttgcgtg tggtgttgtg cacctacttg ccatcatttt gtacttgttt aagtaccgct    6780
gcctgcacaa catccttgtt ggcgatggag tgttctctgc ggctttcttc ctgcgatatt    6840
ttgccgaggg aaagttgagg gaggggggtgt cgcaatcctg cgggatgaat catgagtcac    6900
ttaccggtgc cctcgctatg agactcaatg acgaggactt ggatttcctc acgaaatgga    6960
ctgatttcaa gtgctttgtt tctgcgtcca acatgagaaa tgctgcgggc caattcatcg    7020
aggctgccta tgctaaagca cttagagtag aacttgccca gttggtgcag gttgataagg    7080
ttcggggtac tttggccaaa cttgaagctt ttgccgacac cgtggcaccc caactctcgc    7140
ccggtgacat tgttgtcgct cttggccata cgcctgttgg cagtatcttc gacctgaagg    7200
ttggtaacac caagcacact ctccaagcca tcgagaccag ggtccttgct gggtccaaaa    7260
tgaccgtggc gcgcgtcgtc gatccgaccc ccacgccccc acccgcaccc gtgcccatcc    7320
ccctcccacc gaaggttttg gagaacggtc caaacgcttg gggggatgaa gaccgtttga    7380
ataaaaagag gaggcgcagg atggaagccc tcggcatcta tgttatgggc gggaaaaagt    7440
```

```
accagaaatt tgggacaag aattccggtg acgtgtttta tgaggaggtc cataacaaca    7500
cagatgagtg ggagtgcctc agagttggcg accctgccga ctttgaccct gagaagggaa    7560
ctttgtgtgg gcatgtcacc attgaagata gggcttacca tgtttacacc tccccatctg    7620
gtaagaaatt cctagtcccc gtcaacccag agaacggaag agttcaatgg gaggctgcaa    7680
agctttccgt tgagcaggcc cttggtatga tgaacgtcga cggcgagctg actgccaagg    7740
aactggagaa actgaaaaga ataattgaca aactccaggg cctgactaag gagcagtgtt    7800
taaactgcta gccgccagcg acttgacccg ctgtggtcgc ggcggcttgg ttgttactga    7860
aacagcggta aaaatagtca aatttcacaa ccggaccttc accctgggac ctgtgaattt    7920
aaaagtggcc agtgaggttg agctaaaaga cgcggttgag cacaaccaac acccggttgc    7980
gagaccgatc gatggtggag ttgtgctcct gcgttccgcg gttccttcgc ttatagacgt    8040
cttgatctcc ggtgctgatg catctcccaa gttacttgcc catcacgggc cgggaaacac    8100
tgggatcgat ggcacgctct gggattttga gtccgaagcc actaaagagg aagtcgcact    8160
cagtgcgcaa ataatacagg cttgtgacat taggcgcggc gacgctcctg aaattggtct    8220
cccttacaag ctgtaccctg ttaggggtaa ccctgagcgg gtgaaaggag ttctgcagaa    8280
tacaaggttt ggagacatac cttacaaaac ccccagtgac actggaagcc cagtgcacgc    8340
ggctgcctgc cttacgccca acgccactcc ggtgactgat gggcgctccg tcttggccac    8400
gaccatgccc cccgggtttg agttatatgt accgaccata ccagcgtctg tccttgatta    8460
ccttgactct aggcctgact gccctaaaca gctgacagag cacggctgcg aagatgccgc    8520
actgaaagac ctctctaaat atgacttgtc cacccaaggc tttgttttac ctggagttct    8580
tcgccttgtg cggaaatacc tgtttgccca tgtaggtaag tgcccacccg ttcatcggcc    8640
ttctacttac cctgctaaga attctatggc tggaataaat gggaacaggt tcccaaccaa    8700
ggacattcag agcgtccctg aaatcgacgt tctgtgcgca caggctgtgc gagaaaactg    8760
gcaaactgtc acccccttgta ctcttaagaa acagtattgc gggaagaaga agactaggac    8820
catactcggc accaataact tcatcgcact agcccaccga gcagtgttga gtggtgttac    8880
ccagggcttc atgaaaaagg cgtttaactc gcccatcgcc ctcggaaaga acaagtttaa    8940
ggagctacag actccggtcc tgggcaggtg ccttgaagct gatctcgcat cctgcgatcg    9000
atccacgcct gcaattgtcc gctggtttgc cgccaacctt ctttatgaac ttgcctgtgc    9060
tgaagagcat ctaccgtcgt acgtgctgaa ctgctgccac gacttactgg tcacgcagtc    9120
cggcgcagtg actaagagag gtggcctgtc gtctggcgac ccgatcacct ctgtgtctaa    9180
caccatttat agtttggtga tctatgcaca gcatatggtg cttagttact tcaaaagtgg    9240
tcacccccat ggccttctgt tcttacaaga ccagctaaag tttgaggaca tgctcaaggt    9300
tcaacccctg atcgtctatt cggacgacct cgtgctgtat gccgagtctc ccaccatgcc    9360
aaactatcac tggtgggttg aacatctgaa tttgatgctg gggtttcaga cggacccaaa    9420
gaagacagca ttaacagact cgccatcatt tctaggctgt agaataataa atgggcgcca    9480
gctagtcccc aaccgtgaca ggatcctcgc ggccctcgcc tatcacatga aggcgagtaa    9540
tgtttctgaa tactatgcct cagcggctgc aatactcatg gacagctgtg cttgtttgga    9600
gtatgatact gaatggtttg aagaacttgt agttggaata gcgcagtgcg cccgcaagga    9660
cggctacagc tttcccggca cgccgttctt catgtccatg tgggaaaaac tcaggtccaa    9720
ttatgagggg aagaagtcga gagtgtgcgg gtactgcggg gccccggccc cgtacgctac    9780
tgcctgtggc ctcgacgtct gcatttacca cacccacttc caccagcatt gtccagtcac    9840
```

```
aatctggtgt ggccatccag cgggttctgg ttcttgtagt gagtgcaaat ccctgtagg    9900
gaaaggcaca agcccttag acggagtgtt ggaacaagtc ccgtataagc ccccacggac    9960
cgttatcatg catgtggagc agggtctcac cccccttgat ccaggtagat accaaactcg  10020
ccgcggatta gtctctgtca ggcgtggaat taggggaaat gaagttgaac taccagacgg  10080
tgattatgct agcaccgcct tgctccctac ctgcaaagag atcaacatgg tcgctgtcgc  10140
ttccaacgta ttgcgcagca ggttcatcat cggcccaccc ggtgctggga aaacatactg  10200
gctccttcaa caggtccagg atggtgatgt tatttacaca ccaactcacc agaccatgct  10260
tgacatgatt agggctttgg ggacgtgccg gttcaacgtc ccggcaggca caacgctgca  10320
attcccgtc ccctcccgca ccggtccgtg ggttcgcatc ctagccggcg gttggtgtcc   10380
tggcaagaat tccttcctag atgaagcagc gtattgcaat caccttgatg ttttgaggct  10440
tcttagtaaa actaccctca cctgtctagg agacttcaag caactccacc cagtgggttt  10500
tgattctcat tgctatgttt ttgacatcat gcctcaaact caactgaaga ccatctggag  10560
gtttggacag aatatctgtg atgccattca gccagattac agggacaaac tcatgtccat  10620
ggtcaacaca acccgtgtga cctacgtgga aaaacctgtc aggtatgggc aggtcctcac  10680
cccctaccac agggaccgag aggacgacgc catcactatt gactccagtc aaggcgccac  10740
attcgatgtg gttacattgc atttgcccac taaagattca ctcaacaggc aaagagccct  10800
tgttgctatc accagggcaa gacacgctat ctttgtgtat gacccacaca ggcagctgca  10860
gggcttgttt gatcttcctg caaaaggcac acccgtcaac ctcgcagtgc accgcgacgg  10920
gcagctgatc gtgctggata gaaataacaa agaatgcacg gttgctcagg ctctaggcaa  10980
cggggataaa tttagggcca cagacaagcg tgttgtagat tctctccgcg ccatttgtgc  11040
tgatctagaa gggtcgagct ctccgctccc caaggtcgca cacaacttgg gattttattt  11100
ctcacctgat ttaacacagt ttgctaaact cccagtagaa cttgcacctc actgccgcgt  11160
ggtgacaacc cagaacaatg aaaagtggcc agatcggctg gttgccagcc ttcgccctat  11220
ccataaatac agccgcgcgt gcatcggtgc cggctatatg gtgggccctt cggtgtttct  11280
aggcactcct ggggtcgtgt catactatct cacaaaattt gttaagggcg aggctcaagt  11340
gcttccggag acgttttca gcaccggccg aattgaggta gactgccggg aatatcttga   11400
tgatcgggag cgagaagttg ctgcgtccct cccacacgct ttcattggcg acgtcaaagg  11460
cactaccgtt ggaggatgtc atcatgtcac ctccagatac ctcccgcgcg tccttcccaa  11520
ggaatcagtt gcggtagtcg gggtttcaag ccccggaaaa gccgcgaaag cattgtgcac  11580
actgacagat gtgtacctcc cagatcttga agcctatctc cacccggaga cccagtccaa  11640
gtgctggaaa atgatgttgg acttcaaaga agttcgacta atggtctgga agacaaaac   11700
agcctatttc caacttgaag gtcgctattt cacctggtat cagcttgcca gctatgcctc  11760
gtacatccgt gttcctgtca actctacggt gtacttggac ccctgcatgg gccccgccct  11820
ttgcaacagg agagtcgtcg gtccacccca ctgggggggct gacctcgcgg tcacccctta  11880
tgattacggc gctaaaatta tcctgtctag cgcgtaccat ggtgaaatgc cccccggata  11940
caaaattctg gcgtgcgcgg agttctcgtt ggatgaccca gttaagtaca acatacctg   12000
ggggtttgaa tcggatacag cgtatctgta tgagttcacc ggaaacggtg aggactggga  12060
ggattacaat gatgcgtttc gtgcgcgcca ggaagggaaa atttataagg ccactgccac  12120
cagcwtgaag ttttattttc ccccgggccc tgtcattgaa ccaactttag gcctgaattg  12180
```

-continued

```
attaattaat ttaaatggcg ccaatgaaat ggggtccatg caaagccttt ttgacaaaat    12240
tggtcaactt tttgtggatg ctttcacgga attcttggtg tccattgttg atatcatcat    12300 attttttggcc attttgtttg gcttcaccgt cgccggttgg ctggtggtct tttgcatcag   12360
attggtttgc tccgcgatac tccgtgcacg ccctgccttt cactctgagc agttacagaa   12420
gatcctatga ggcctttctt tccctgtgtc aggtggacat tcccacctgg ggaatcaaac   12480
atcctctggg ggtgctttgg caccataagg tgtcaaccct gattgatgaa atggtgtcgc   12540
gtcgaatgta ccgcatcatg gaaaaagcag gacaggctgc ctggaaacag gtggtgagcg   12600
aggccacgct gtctcgcatt agtagtttgg atgtggtggc tcattttcaa catcttgccg   12660
ccgttgaagc cgagacctgt aaatatttgg cctctcggct acccatgcta cacaacctgc   12720
gcatgacggg gtcaaatgta accatagtat ataatggtac tttgaatcag gtgtttgcca   12780
ttttcccgac ccctggttcc cggccaaagc ttcatgattt tcagcaatgg ctgatagctg   12840
tgcattcgtc catattttcc tctgttgcag cttcttgtac tctgtttgtt gtactgtggt   12900
tgcgggtccc aatgctacgt actgtttttg gtttccgctg gttaggggca attttttcctt  12960 cgagctcttg gtgaattaca cggtgtgccc accttgcctc acccggcaag cagccgcaca   13020
gcgctacgaa cctggcaagg ctctttggtg cagaattggg tacgatcgat gtgaggagga   13080
cgatcacgac gagctagggt tcgtgatacc gtctggcctc tccagcgaag gccactagtc   13140
tagtgtttac gcctggttgg cgttttttgtc cttcagttac acggcccagt ttcatcctga   13200
gatattcggg ataggaatg tgagcaaagt ctatgttgac atcaaacacc aattcatctg    13260
cgctgttcat gatgggcaga acaccacctt gccccgccat gacaactttt cagccgtgtt   13320
tcagacctat taccagcatc aagtcgacgg cggcaattgg tttcacctag aatggctgcg   13380
tcccttcttt tcctcttggt tggttttaaa tgtctcgtgg tttctcaggc gtttgcctgc   13440
aagccatgtt tcagttcgag tctttcagac attaagacca acaccaccgc agcagcgggc   13500
tttgctgtcc tccaggacat cagctgcctt aggcatggcg atccgtcctc tgcggcgatt   13560
cgcaaaagct ctcagtgccg cacggcgata gggacacccg tgtatatcac cattacagcc   13620
aatgtgacag atgagaatta tttacactcc tctgatctcc tcatgctttc ttcttgcctt   13680
ttctatgctt ctgagatgag tgaaaaggga tttaaggtgg tatttggcaa tgtgtcaggc   13740
atcgtggctg tgtgtgttaa ttttaccagc tacgtccaac atgtcaggga cttcacccaa   13800
cgctccttgg tggtcgatca tgtgcggctg ctccatttca tgacacctga ggccatgagg   13860
tgggcaactg ttttagcctg tcttttttgcc attctgttgg cagtttgaat gtttaagtat   13920
gttggggaaa tgcttgaccg cgggttgctg ctcgcgattg cttctttttt ggtgtatcgt   13980
gccgttctgt tttgctgtgc tcgtcaacgc cagctacagc agcagctctc atttacagtt   14040
gatttataac ttgacgctat gtgagctgaa tggtacagat tggctggcta ataaatttga   14100
ttgggcagcg gagagttttg tcatctttcc tgtgttgacc cacatcgttt cctatggtgc   14160
actaaccacc agccacttcc ttgacacagt tggtctggtt actgtgtcta ccgccgggtt   14220
ttatcatggg cggtatgtcc tgagtagcat ctacgcggtc tgtgccctgg gctgcttaat   14280
ttgcttcgtc attaggttgg ccaataactg tatgtcctgg cgctactcat gcacaagata   14340
caccaacttt cttctggaca ctaagggcag actctatcgt tggcggtcgc ctgtcatcat   14400
agagaaaggg ggtaaggtag aggtcgaagg ccatctgatc gacctcaaaa gagttgtgct   14460
tgatggttcc gcggcaaccc cttaaccag agtttcagcg gaacaatggg gtcgtcccta   14520
gacgactttt gtcatgacag cacggctcca cagaaggtgc tcttggcgtt ttctattact   14580
```

```
tacacgccag tgatgatata tgccctaaag gtaagtcgcg gccgattgct ggggcttctg    14640
caccttctga tcttcctgaa ttgtgctttc accttcgggt atatgacatt cgcgcacttt    14700
cagagtacaa atagggtcgc gctcactatg ggagcagtag ttgcactcct ttgggggtg     14760 tactcagcca tagaaacttg gaggttcatc acctctagat gccgtttgtg cttgttaggc    14820
cgcaggtaca ttctggcccc tgcccaccac gttgaaagtg ccgcaggctt tcatccgatt    14880
acggcaaatg ataaccacgc atttgtcgtc cggcgtcccg gctccactac ggttaacggc    14940
acattggtgc ccgggttgaa gagcctcgtg ttgggtggca gaaaagctgt aaaacgggga    15000
gtggttaacc ttgttaaata tgccaaataa caacggcaaa cagcagaaga aaagaaggg     15060 ggatggccag ccagtcaatc agctgtgcca gatgctgggt aagatcatcg cccagcaaaa    15120
ccagtccaga ggtaagggac cgggaaagaa aaacaagaag aaaaacccgg agaagcccca    15180
ttttcctctg cgactgaat atgacgtcag acaccacttt accctagtg agcggcaatt      15240 gtgcctgtcg tcaatacaga ctgcctttaa tcaaggcgct ggtacttgca ccctgtccga    15300
ttcagggagg ataagttaca ctgtggagtt tagtttgccc acgcatcata ctgtgcgcct    15360
gattcgcgtc acagcatcac cctcagcatg atgggctggc attcttgagg catctcagtg    15420
tttgaattgg aagaatgtgt ggtgaatggc actgattgat attgtgcctc taagtcacct    15480
attcaattag ggcgaccgtg tgggggtaag atttaattgg cgaaaaccat gcggccgaaa    15540
ttaaaaaaaa aaaaaaaaaa aaaa                                          15564

<210> SEQ ID NO 3
<211> LENGTH: 23
<212> TYPE: DNA
<213> ORGANISM: Artificial
<220> FEATURE:
<223> OTHER INFORMATION: PSA linker

<400> SEQUENCE: 3
ttaattaatt taaatggcgc gcc                                              23

<210> SEQ ID NO 4
<211> LENGTH: 28
<212> TYPE: DNA
<213> ORGANISM: artificial sequence
<220> FEATURE:
<223> OTHER INFORMATION: SF7682 primer

<400> SEQUENCE: 4
ctttccgttg agcaggccct tggtatga                                         28

<210> SEQ ID NO 5
<211> LENGTH: 44
<212> TYPE: DNA
<213> ORGANISM: artificial sequence
<220> FEATURE:
<223> OTHER INFORMATION: PSA1R primer

<400> SEQUENCE: 5
ggcgcgccat ttaaattaat taatcaattc aggcctaaag ttgg                       44

<210> SEQ ID NO 6
<211> LENGTH: 42
<212> TYPE: DNA
<213> ORGANISM: artificial sequence
<220> FEATURE:
<223> OTHER INFORMATION: PSA2F primer
```

```
<400> SEQUENCE: 6
ttaattaatt taaatggcgc gccaatgaaa tggggtccat gc                         42

<210> SEQ ID NO 7
<211> LENGTH: 40
<212> TYPE: DNA
<213> ORGANISM: artificial sequence
<220> FEATURE:
<223> OTHER INFORMATION: Sp2R primer

<400> SEQUENCE: 7
gagtgacgag gactcgagcg cattaattt tttttttttt                             40

<210> SEQ ID NO 8
<211> LENGTH: 23
<212> TYPE: DNA
<213> ORGANISM: artificial sequence
<220> FEATURE:
<223> OTHER INFORMATION: PSA polylinker primer

<400> SEQUENCE: 8
ttaattaatt taaatggcgc gcc                                              23

<210> SEQ ID NO 9
<211> LENGTH: 24
<212> TYPE: DNA
<213> ORGANISM: artificial sequence
<220> FEATURE:
<223> OTHER INFORMATION: SR12709 primer

<400> SEQUENCE: 9
ccccgtcatg cgcaggttgt gtag                                             24

<210> SEQ ID NO 10
<211> LENGTH: 13117
<212> TYPE: DNA
<213> ORGANISM: partial sequence Porcine Reproductive and Respiratory
      Syndrome Virus clone

<400> SEQUENCE: 10
tatgacgtat aggtgttggc tctatgcctt gacatttgta ttgtcaggag ctgtgatcat      60
tgacacagcc caaagcttgc tgcacagaaa caccccttctg tgacagcctc cttcagggga   120 gtttagggt ctgtccctag caccttgctt ccggagttgc actgctttac ggtctctcca    180
cccctttaac catgtctggg atacttgatc ggtgcacgtg tacccccaat gccagggtgt    240
tcatggcgga gggccaagtc tactgcacac gatgcctcag tgcacggtct ctccttcctc    300
tgaatctcca gttcctgaa ctcggggtgc tgggcctatt ctataggccc gaagagccac     360
tccggtggac gttgccacgt gcattcccca ctgttgagtg ctccccgcc ggagcctgct     420 ggctttctgc catctttcca attgcacgaa tgaccagtgg aaatctgaac tttcaacaaa    480
gaatggtgcg ggtcgcagct gagctttaca gagccggcca gctcacccct gcagtcttga    540
agactctaca gtttatgaa cggggttgcc actggtaccc cattgttgga cctgttcctg     600
gagtggccgt ttatgccaac tccctacatg tgagtgataa acctttcccg ggagcaactc    660
acgtgttaac caacctgccg ctcccgcaga gacccaagcc tgatgatttt tgccccttg     720 agtgtgctat ggctactgtc tatgacattg gtcatgacgc cgtcatgtat gtggccgaag    780
agaaagtctc ctgggcccct cgtggcgggg atgaagtgaa attcgaacct gtccccgggg    840
agttgaagtt gattgcgaac cgactccgca cctccttccc gccccaccac gcagtggaca    900
```

```
tgtctaagtt caccttcaca gccctgggc gtggtgtttc tatgcgggtc gaacgccaac    960
acggctgcct ccccgctgac acagttcctg aaggcaactg ctggtggagc ttgttcaact   1020
tgctcccact ggaagttcag aacaaagaaa ttcgtcatgc cggccaattt ggctaccaga   1080
ctaagcatgg tgtctctggc aagtacctac agcggaggct gcaagttaat ggtcttcgag   1140
cagtaactga cctaaatgga cctatcgtcg tacagtgctt ctccgttaag gagagttgga   1200
tccgccactt gaaactggcg gaagaaccca gctaccctgg gtttgaggac ctcctcagaa   1260
taagggttga gcccaacacg tcgccattgg ctgacaagga tgaaaaaatt ttccggtttg   1320
gcaatcacaa gtggtatggc gctggaaaga gagcaaggaa agcacgctct agtgcgactg   1380
ctacagtcgc tggccgcgct ttgcccgttc gtgaaacccg gcaggtcgag gagcacgagg   1440
ttgccggcgc caacaaggct gagcacctca aacactactc cccgcctgcc gaagggaatt   1500
gtggttggca ctgcatttcc gccatcggca accggatgtt gaattccaaa tttgaaacca   1560
cccttcccga aagagtgaga cctccagatg actgggctac tgatgaggat cttgtgaatg   1620
ccatccaaat cctcagactc cctgcggcct ggacaggaa cggtgcttgt gctagcgcca    1680
agtacgtact taagctggaa ggtgagcatt ggactgtcac tgtgacccct gggatgtccc   1740
cttctttgct ccctcttgaa tgtgttcagg gctgttgcga gcataagggc ggtcttggtt   1800
ccccagatgc agtcgaggtt ttcggatttg accctgcctg ccttgactgg ctggctgagg   1860
tgatgcactt gcctagcaat gccatcccag ccgctctggc cgaaatgtcc ggcgattcca   1920
atcgtccggc ttccccggtc accacgtgt ggactgtttc gcagttctta gcccgccaca    1980
acggagggaa tcaccctgac caaatacgct tagggaaaat tatcagcctt tgtcaggtga   2040
ttgaggactg ctgctgttcc cagaacaaaa ccaaccgggt caccccggag gaggtcgcag   2100
caaagattga cctgtacctc cgtggtgcaa caaatcttga agaatgcttg gccaggcttg   2160
agaaagcgcg cccgccacgc gtaatggaca cctcctttga ttgggatgtt gtgctccctg   2220
gggttgaggc ggcaactcaa acgaccgaac tgccccaagt caaccagtgt cgcgctctgg   2280
tccctgttgt gactcaaaag tccttggaca caactcggt ccctctgacc gccttttcac    2340
tggctaacta ctactaccgc gcgcaaggtg acgaagttcg tcaccgtgaa agactaacca   2400
ccgtgctctc taagttggaa ggggttgttc gagaagaata cgggctcatg ccaaccgggc   2460
ctggtccacg gcccacactg ccacgcgggc tcgacgaact caaggaccag atggaggtgg   2520
acttgctgaa actggctaac gcccagatga cttcggacat gatggcctgg gcagtcgagc   2580
aggttgacct aaagacttgg gtcaagaact atccgcggtg gacaccacca cctcctccgc   2640
caatagttca gcctcgaaaa acgaagcttg tcaagagctt accagagagc aagcctgttc   2700
ctgcaccgcg taggaaggtc aggtccgatt gtgactgccc cacccctatcg ggcaacaatc   2760
ttcctgacag ttgggaagat ttggctgttg gttgcccctc tgatctccct acctcacctg   2820
agccggtaac acctttgagt gagccggcat ctgtgtccgc accgcgacgc tcttttaggc   2880
cggtgaagcc tttgagtgaa ccagttccag tccctgcacc gcgcaagact gtgtcccgac   2940
cggcaacacc tctgagtgag ccgatccctg tgccgcacc gcgacgcaag tttcagcagg    3000
tagaaaaagt gaatccggcg gcggcaaccc tggcgtgcca agacgagttt ccagatttgt   3060
ctgcatcctc gcatactgaa tatgaggcgt ctccccttgt actaccgcag aacgggacg    3120
ttcttgaagt ggaggagcgg gaagctgagg aaatcctgag tggaatctca gacatactgg   3180
atgccatcaa accggcatct gcatcatcaa gcagctccct gtcaagtgtg gcgatcacac   3240
gcccgaaata ctcagctcaa gccatcattg actcgggtgg gccctacagc gggcatctcc   3300
```

```
aagaggtgaa ggaaacatgc ctaagcatca tgagtgaggc atgtgatgtg accaagcttg   3360
atgaccctgc cacgcaggaa tggctttctc gcatgtggga tagggtggac atgctgactt   3420
ggcgcaatac gtctgttcac caggcgtctc gcaccttgga cgacagattt aagtttctcc   3480
cgaagatgat acttgaaaca ccgccgccct acccgtgtgg gttcgtgatg atgcctcgca   3540
cacctgcacc ctccgtgggt gcggagagcg acctcactat tggctcagtc gctactgagg   3600
acgttccacg catcttcggg aaagtaaatg atgtctgcaa gatgatcgac cagagaccct   3660
tggtactctt tgaaaatgag ctggcagatg accaacctgc cagagatcct cggacatcat   3720
cgcagaggtt tgacgggagc acaccagctc cgcccgcagg cacggatggc accggtttgg   3780
cttcgggccc tggagtgaga gaagtggatt catgtgaggc gagctcaacc gagaaaaatg   3840
aacagccctt cgtgttgaac ggcggcgcca gcacacaggc gtcaacgttt accaatttgc   3900
cgcctccagg cggtatagat gcgggcggga gtgggccgtt acaaacggtg cgaaagaagg   3960
ctgaacggtt ctttgaccta ctaagccgtc aggttttaa tctcgtctcc catctccctg    4020
ttttcttctc acgccttttc aaacctggcg gtgactattc tccgggtgat tggggttttg   4080
cagcttttac tttattgtgc ctcttttttgt gttacagtta cccggccttt ggtgctgttc   4140
ccctcttggg tgtattttct gggtcttctc ggcgtgttcg aatggggggtt tttggctgct   4200 ggttggcttt tgctgttagt ctgttcaaac ctgtgtccga cccagtcggc gctgcttgtg   4260
aatttgattc gccagagtgt agaaacatcc ttcattcttt tgagcttctc aaaccttggg   4320
accctgttcg cggccttgtt gtgggccccg tcggtctcag tcttgccatt tttggcaggt   4380
tattgggcgg ggcacgccac atctggcact ttttgcttag gtttggcatt gttgcagatt   4440
gtatcttggc tggagcttat gtgctttctc aaggcaggtg taaaaagtgc tggggatctt   4500
gtataagaac tgctcctaat gaggtcgcct ttaacgtgtt ccttttaca cgtgcgacca    4560 ggtcgtcact tatcgacctg tgcaatcggt tttgcgcgcc aaaaggtatg acccccattt   4620
tcctcgccac tgggtggcgc gggtgctgga ccggccgaag ccccattgag caaccctctg   4680
aaaaacccat cgcgtttgcc cagttggatg aaaaaaagat tacggctagg actgtggtcg   4740
cccagcccta tgaccccaac caagctgtaa agtgcttgcg ggtattgcag gcgggcgggg   4800
tgatggtggc tgaggcagtc ccaaaagtgg tcaaagtttc tgctgttcca ttccgagccc   4860
ccttctttcc caccggagtg aaagttgatc ctgaatgcag gattgtggtt gaccccgaca   4920
ctttcactgc agccctccga tctggctact ccaccacaaa cctcgtcctt ggtgtggggg   4980
actttgccca gctgaatgga ttaaaaatca ggcaaatttc caagccttca ggggagtc    5040 cacacctcat ggctgccctg catgttgctt gctctatggc tctgcacatg cttgttggga   5100
tttatgtgac tgctgtgggt tcttgcggca ccggcactaa cgatccgtgg tgcgccaacc   5160
cgtttgccgt ccctggctac ggacctggct ctctctgcac gtccagattg tgcatctccc   5220
aacatggcct taccctaccc ttgacagcac ttgtggcggg attcggcttt caggaaattg   5280
ccttggttat tttgattttt gtttctatcg gaggcatggc tcatagattg agttgcaagg   5340
ctgatatgct gtgtatttg tttgcaatcg ccagctatgt ttgggtacct cttacctggt   5400
tgctttgtgt gtttccttgc tggttgcgct gttttttcgtt gcaccccctc accatcctat   5460
ggttggtgtt tttcctgatt tctgtaaata tgccttcagg aatcttggcc ttggtgttgt   5520
tgatttctct ctggcttctt ggtcgttata ccaacgttgc cggtcttgtc actccctatg   5580
acattcatca ttacaccagt ggccccccgcg gtgttgccgc cttggctacc gcaccagatg   5640
```

-continued

```
ggacctactt ggccgctgtc cgccgcgccg cgttgactgg tcgcaccatg ctgtttaccc    5700
cgtctcagct cgggtccctt cttgagggcg cttttcagaac tcgaaagccc tcactgaaca   5760
ccgttaatgt ggtcgggtcc tccatgggct ctggcgggt gttcaccatc gacgggaaaa    5820
ttaagtgcgt aactgctgca catgtcctta cgggtaattc agctagggtt tccggggttg    5880
gcttcaatca aatgcttgac ttcgatgtga aggagactt cgccatagcc gattgcccag     5940
actggcaagg ggctgctccc aagacccaat tctgcgagga aggatggact ggccgggcct    6000
attggctaac gtcttctggt gtcgaacccg gcgtcattgg aaaaggattc gccttctgct    6060
tcaccgcgtg cggcgattcc ggatccccag taatcaccga ggccggcgag cttatcggcg    6120
ttcacacggg gtcaaataaa caaggaggag gcatcgtcac gcgcccctca ggccagtttt    6180
gtagtgtggc acccgtcaaa ttaagcgaac taagtgaatt cttttgcaggg cctaaggtcc   6240 cgctcggtga tgtgaaagtt ggcagccaca taattgaaga cgtaggcgag gtgccttcag    6300
atctttgcgc cttgcttgct gccaaacctg aactggaagg aggcctctcc accgttcaac    6360
ttctgtgtgt gttttcctc ctgtggagaa tgatgggaca tgcctggacg cccttggttg     6420
ccgtagggtt tttatcttg aatgaggtcc tcccagctgt cctggtccgg agtgttttct      6480
cctttggaat gtttgtgcta tcctggctca caccatggtc tgcgcaagtt ctgatgatca    6540
ggcttctaac agcagctctt aacaggaata gatggtcact tgccttttac agcctcggtg    6600
caatgactgg ttttgtcgca gatctcgcgg ctactcaggg gtatccgttg caggcagtga    6660
tgagtttgag cacttatgca ttcctgcctc ggataatggt tgtgacttca ccagtcccag    6720
tggttgcgtg tggtgttgtg cacctacttg ccatcatttt gtacttgttt aagtaccgct    6780
gcctgcacaa catccttgtt ggcgatggag tgttctctgc ggctttcttc ctgcgatatt    6840
ttgccgaggg aaagttgagg gagggggtgt cgcaatcctg cgggatgaat catgagtcac    6900
ttaccggtgc cctcgctatg agactcaatg acgaggactt ggatttcctc acgaaatgga    6960
ctgatttcaa gtgctttgtt tctgcgtcca acatgagaaa tgctgcgggc caattcatcg    7020
aggctgccta tgctaaagca cttagagtag aacttgccca gttggtgcag gttgataagg    7080
ttcggggtac tttggccaaa cttgaagctt ttgccgacac cgtggcaccc caactctcgc    7140
ccggtgacat tgttgtcgct cttggccata cgcctgttgg cagtatcttc gacctgaagg    7200
ttggtaacac caagcacact ctccaagcca tcgagaccag ggtccttgct gggtccaaaa    7260
tgaccgtggc gcgcgtcgtc gatccgaccc ccacgccccc acccgcaccc gtgcccatcc    7320
ccctcccacc gaaggttttg gagaacggtc caaacgcttg gggggatgaa gaccgtttga    7380
ataaaaagag gaggcgcagg atggaagccc tcggcatcta tgttatgggc gggaaaaagt    7440
accagaaatt ttgggacaag aattccggtg acgtgtttta tgaggaggtc cataacaaca    7500
cagatgagtg ggagtgcctc agagttggcg accctgccga ctttgaccct gagaagggaa    7560 cttttgtgtgg gcatgtcacc attgaagata gggcttacca tgtttacacc tccccatctg    7620
gtaagaaatt cctagtcccc gtcaacccag agaacggaag agttcaatgg gaggctgcaa    7680
agctttccgt tgagcaggcc cttggtatga tgaacgtcga cggcgagctg actgccaagg    7740
aactggagaa actgaaaaga ataattgaca aactccaggg cctgactaag gagcagtgtt    7800
taaactgcta gccgccagcg acttgacccg ctgtggtcgc ggcggcttgg ttgttactga    7860
aacagcggta aaaatagtca aatttcacaa ccggaccttc accctgggac ctgtgaattt    7920
aaaagtggcc agtgaggttg agctaaaaga cgcggttgag cacaaccaac acccggttgc    7980
gagaccgatc gatggtggag ttgtgctcct gcgttccgcg gttccttcgc ttatagacgt    8040
```

```
cttgatctcc ggtgctgatg catctcccaa gttacttgcc catcacgggc cgggaaacac    8100
tgggatcgat ggcacgctct gggattttga gtccgaagcc actaaagagg aagtcgcact    8160
cagtgcgcaa ataatacagg cttgtgacat taggcgcggc gacgctcctg aaattggtct    8220
cccttacaag ctgtaccctg ttaggggtaa ccctgagcgg gtgaaaggag ttctgcagaa    8280
tacaaggttt ggagacatac cttacaaaac ccccagtgac actggaagcc cagtgcacgc    8340
ggctgcctgc cttacgccca cgccactcc ggtgactgat gggcgctccg tcttggccac    8400
gaccatgccc cccgggtttg agttatatgt accgaccata ccagcgtctg tccttgatta    8460
ccttgactct aggcctgact gccctaaaca gctgacagag cacggctgcg aagatgccgc    8520
actgaaagac ctctctaaat atgacttgtc cacccaaggc tttgttttac ctggagttct    8580
tcgccttgtg cggaaatacc tgtttgccca tgtaggtaag tgcccacccg ttcatcggcc    8640
ttctacttac cctgctaaga attctatggc tggaataaat gggaacaggt tcccaaccaa    8700
ggacattcag agcgtccctg aaatcgacgt tctgtgcgca caggctgtgc gagaaaactg    8760
gcaaactgtc acccctttgta ctcttaagaa acagtattgc gggaagaaga agactaggac    8820
catactcggc accaataact tcatcgcact agcccaccga gcagtgttga gtggtgttac    8880
ccagggcttc atgaaaaagg cgtttaactc gcccatcgcc ctcggaaaga acaagtttaa    8940
ggagctacag actccggtcc tgggcaggtg ccttgaagct gatctcgcat cctgcgatcg    9000
atccacgcct gcaattgtcc gctggttgc cgccaacctt ctttatgaac ttgcctgtgc    9060
tgaagagcat ctaccgtcgt acgtgctgaa ctgctgccac gacttactgg tcacgcagtc    9120
cggcgcagtg actaagagag gtggcctgtc gtctggcgac ccgatcaccct ctgtgtctaa    9180 caccattat agtttggtga tctatgcaca gcatatggtg cttagttact tcaaaagtgg    9240 tcaccccccat ggccttctgt tcttacaaga ccagctaaag tttgaggaca tgctcaaggt    9300 tcaaccccctg atcgtctatt cggacgacct cgtgctgtat gccgagtctc ccaccatgcc    9360
aaactatcac tggtgggttg aacatctgaa tttgatgctg gggtttcaga cggacccaaa    9420
gaagacagca ttaacagact cgccatcatt tctaggctgt agaataataa atgggcgcca    9480
gctagtcccc aaccgtgaca ggatcctcgc ggccctcgcc tatcacatga aggcgagtaa    9540
tgtttctgaa tactatgcct cagcggctgc aatactcatg acagctgtg cttgtttgga    9600 gtatgatact gaatggtttg aagaacttgt agttggaata gcgcagtgcg cccgcaagga    9660
cggctacagc tttcccggca cgccgttctt catgtccatg tgggaaaaac tcaggtccaa    9720
ttatgagggg aagaagtcga gagtgtgcgg gtactgcggg gccccggccc cgtacgctac    9780
tgcctgtggc ctcgacgtct gcatttacca caccccacttc caccagcatt gtccagtcac    9840
aatctggtgt ggccatccag cgggttctgg ttcttgtagt gagtgcaaat ccctgtagg    9900 gaaaggcaca agcccttag acggagtgtt ggaacaagtc ccgtataagc ccccacggac    9960
cgttatcatg catgtggagc agggtctcac cccccttgat ccaggtagat accaaactcg   10020
ccgcggatta gtctctgtca ggcgtggaat taggggaaat gaagttgaac taccagacgg   10080
tgattatgct agcaccgcct tgctccctac ctgcaaagag atcaacatgg tcgctgtcgc   10140
ttccaacgta ttgcgcagca ggttcatcat cggcccaccc ggtgctggga aaacatactg   10200
gctccttcaa caggtccagg atggtgatgt tatttacaca ccaactcacc agaccatgct   10260
tgacatgatt agggctttgg ggacgtgccg gttcaacgtc ccggcaggca caacgctgca   10320
attccccgtc cctcccgca ccggtccgtg ggttcgcatc ctagccggcg gttggtgtcc   10380
```

```
tggcaagaat tccttcctag atgaagcagc gtattgcaat caccttgatg ttttgaggct   10440
tcttagtaaa actaccctca cctgtctagg agacttcaag caactccacc cagtgggttt   10500
tgattctcat tgctatgttt ttgacatcat gcctcaaact caactgaaga ccatctggag   10560
gtttggacag aatatctgtg atgccattca gccagattac agggacaaac tcatgtccat   10620
ggtcaacaca acccgtgtga cctacgtgga aaaacctgtc aggtatgggc aggtcctcac   10680
cccctaccac agggaccgag aggacgacgc catcactatt gactccagtc aaggcgccac   10740
attcgatgtg gttacattgc atttgcccac taaagattca ctcaacaggc aaagagccct   10800
tgttgctatc accagggcaa gacacgctat ctttgtgtat gacccacaca ggcagctgca   10860
gggcttgttt gatcttcctg caaaaggcac acccgtcaac ctcgcagtgc accgcgacgg   10920
gcagctgatc gtgctggata gaaataacaa agaatgcacg gttgctcagg ctctaggcaa   10980
cggggataaa tttagggcca cagacaagcg tgttgtagat tctctccgcg ccatttgtgc   11040
tgatctagaa gggtcgagct ctccgctccc caaggtcgca cacaacttgg gattttattt   11100
ctcacctgat ttaacacagt ttgctaaact cccagtagaa cttgcacctc actggcccgt   11160
ggtgacaacc cagaacaatg aaaagtggcc agatcggctg gttgccagcc ttcgccctat   11220
ccataaatac agccgcgcgt gcatcggtgc cggctatatg gtgggccctt cggtgtttct   11280
aggcactcct ggggtcgtgt catactatct cacaaaattt gttaagggcg aggctcaagt   11340
gcttccggag acggttttca gcaccggccg aattgaggta gactgccggg aatatcttga   11400
tgatcgggag cgagaagttg ctgcgtccct cccacacgct ttcattggcg acgtcaaagg   11460
cactaccgtt ggaggatgtc atcatgtcac ctccagatac ctcccgcgcg tccttcccaa   11520
ggaatcagtt gcggtagtcg gggtttcaag ccccggaaaa gccgcgaaag cattgtgcac   11580
actgacagat gtgtacctcc cagatcttga agcctatctc caccggagaa cccagtccaa   11640
gtgctggaaa atgatgttgg acttcaaaga agttcgacta atggtctgga agacaaaaac   11700
agcctatttc caacttgaag gtcgctattt cacctggtat cagcttgcca gctatgcctc   11760
gtacatccgt gttcctgtca actctacggt gtacttggac ccctgcatgg gccccgccct   11820
ttgcaacagg agagtcgtcg ggtccaccca ctgggggggct gacctcgcgg tcaccccctta   11880 tgattacggc gctaaaatta tcctgtctag cgcgtaccat ggtgaaatgc cccccggata   11940
caaaattctg gcgtgcgcgg agttctcgtt ggatgaccca gttaagtaca acatacctg   12000 ggggtttgaa tcggatacag cgtatctgta tgagttcacc ggaaacggtg aggactggga   12060
ggattacaat gatgcgtttc gtgcgcgcca ggaagggaaa atttataagg ccactgccac   12120
cagcwtgaag ttttatttc ccccgggccc tgtcattgaa ccaactttag gcctgaattg   12180
attaattaat ttaaatggcg ccaatgaaat ggggtccatg caaagccttt ttgacaaaat   12240
tggtcaactt tttgtggatg ctttcacgga attcttggtg tccattgttg atatcatcat   12300 attttggcc atttttgttg gcttcaccgt cgccggttgg ctggtggtct tttgcatcag   12360
attggtttgc tccgcgatac tccgtgcacg ccctgccttt cactctgagc agttacagaa   12420
gatcctatga ggcctttctt tcctgtgtc aggtggacat tcccacctgg ggaatcaaac   12480
atcctctggg ggtgctttgg caccataagg tgtcaaccct gattgatgaa atggtgtcgc   12540
gtcgaatgta ccgcatcatg gaaaaagcag gacaggctgc ctggaaacag gtggtgagcg   12600
aggccacgct gtctcgcatt agtagtttgg atgtggtggc tcattttcaa catcttgccg   12660
ccgttgaagc cgagacctgt aaatatttgg cctctcggct acccatgcta cacaacctgc   12720
gcatgacggg gtcaaatgta accatagtat ataatggtac tttgaatcag gtgtttgcca   12780
```

-continued

```
ttttcccgac ccctggttcc cggccaaagc ttcatgattt tcagcaatgg ctgatagctg  12840
tgcattcgtc catattttcc tctgttgcag cttcttgtac tctgtttgtt gtactgtggt  12900
tgcgggtccc aatgctacgt actgtttttg gtttccgctg gttaggggca atttttcctt  12960
cgagctcttg gtgaattaca cggtgtgccc accttgcctc acccggcaag cagccgcaca  13020
gcgctacgaa cctggcaagg ctctttggtg cagaattggg tacgatcgat gtgaggagga  13080
cgatcacgac gagctagggt tcgtgatacc gtctggc                           13117
```

```

<210> SEQ ID NO 11
<211> LENGTH: 25
<212> TYPE: DNA
<213> ORGANISM: artificial sequence
<220> FEATURE:
<223> OTHER INFORMATION: SpeF primer

<400> SEQUENCE: 11
gaaggccact tgactagtgt ttacg                                           25
```

```

<210> SEQ ID NO 12
<211> LENGTH: 2483
<212> TYPE: DNA
<213> ORGANISM: partial sequence Porcine Reproductive and Respiratory
      Syndrome Virus MN-184

<400> SEQUENCE: 12
gcctctccag cgaaggccac tagtccagtg tttacgcctg gttggcgttc ttgtccttca     60
gttacacggc ccagtttcac cccaagatat tcggaatagg gaatgtgagt aaagtttatg    120
ttgacatcaa gcatcaattt atttgtgctg ttcatgacgg gcaaatcacc accttgcctc    180
gccatgacaa cgtctcagcc gtgttccaga cttattacca gcatcaggtc gacggcggca    240
attggtttca cctggaatgg ctgcgcccct tcttctcctc ctggttggtt ttgaacgtct    300
cttggtttct caggcgttcg cctgtaagcc gtgtttcagt tcgagtcttt cagacattaa    360
gtccaacacc accgcagctg caggctttgc tgtcctccaa gacatcagct gtcttaggca    420
tggccactcg tcctctgagg cgactcgcaa aagccgccaa tgccgcacgg cgataggaac    480
gcccgtatac attactgtca cagccaatgt aacagatgag aattatttgc attcctctga    540
ccttctcatg ctttcctctt gccttttcta cgcttccgag atgagtgaaa agggatttga    600
ggtgatattt ggcaatgtgt caggcatagt ggctgtgtgt gtcaacttta ccagctatgt    660
ccaacatgtc aaggagttca cccagcgctc cttggtggtt gaccatgtgc ggttacttca    720
ttttatgaca cctgagacta tgaggtgggc gaccgtttta gcctgtcttt ttgccattct    780
gttggccatt tgaatgttca gatatgttgg ggaaatgctt gaccgcgggc tattgctcgc    840
aattgccttt tttgtggtgt atcgtgccgt tctgtcttgc tgcgctcgtc aacgccaaca    900
gcaacagcag ctcccattta cagttgattt ataacttaac gatatgtgag ctgaatggca    960
cagactggct gaacaatcat tttagttggg cagtggagac tttcgttatc tttcctgtgt   1020
tgactcatat tgtttcctac ggcgccctca ctaccagcca cttccttgac acggtcggcc   1080
tgatcactgt gtccaccgcc ggatactacc atgagcggta tgtcttgagt agcatctatg   1140
ctgcctgcgc cctggctgcg ctgatttgct tcgtcatcag gttgacgaaa aattgtatgt   1200
cctggcgcta ctcatgtacc agatatacca actttcttct ggacaccaag ggcagactct   1260
atcgctggcg gtcacccgtc atcatagaga aaggggtaa aattgaggtt ggaggtgacc    1320
tgatcgacct caagagagtt gtgcttgatg gttccgcggc aacccctgta accaaagttt   1380
```

-continued

```
cagcggaaca atggggtcgt ccttagacga cttctgcaat gacagcacgg ctccacaaaa    1440
ggtgatcttg gcattttcta tcacctacac accagtgatg atatatgccc taaaggtgag    1500
tcgtggccgg ctgctagggc ttttacacct tttgattttt ctaaactgtg cttttacctt    1560
cgggtatatg acatttgtgc actttcagag cacaaacaga gttgcactca ctatgggagc    1620
agtagtcgcg ctcctttggg gggtgtactc agctatagaa acctggaaat tcatcacttc    1680
cagatgccgt ttgtgcttgc taggccgcaa gtacattctg gcccctgccc accacgttga    1740
gagtgccgca ggctttcatc cgattgcggc aagtgataac cacgcatttg tcgtccggcg    1800
tcccggttcc actacggtta acggcacatt ggtgcccggg ttgaaaagcc tcgtgttggg    1860
tggcagaaga gctgtcaaac ggggagtggt aaacctcgtt aaatatgcca ataacaacg    1920 gcaggcagca gaagaaaaag aaaggggacg gccagccagt caatcagctg tgccaaatgt    1980
tgggcaggat catcgcccag caaaaccagt ccagaggtaa gggaccgggg aagaaaagta    2040
agaagaaaag cccggagaag ccccattttc ctctcgcgac tgaagatgac gttagacatc    2100
acttcacccc tagtgagcgg caattgtgtc tgtcgtcaat ccagactgcc tttaaccaag    2160
gcgctggaac ttgtaccctg tcggattcag ggagaataag ttacgctgtg gagtttagtt    2220
tgcctacgca tcatactgtg cgcctaattc gcgtcacagc atcaccccca gcatgatgag    2280
ctggcattct tgagacatcc cagtgtttga attggaagga tgtgtggtga atggcactga    2340
ttgatattgt gcctctaagt cacctattca attagggcga ccgtatgggg gtaatattta    2400
attggcgtga accatgcggc cgaaattaaa aaaaaaaaa aaaaaaaaaa aaaaaaaaaa    2460
aaaaaaaaaa aaaaaaaaaa aaa                                           2483
```

<210> SEQ ID NO 13
<211> LENGTH: 15600
<212> TYPE: DNA
<213> ORGANISM: Porcine Reproductive and Respiratory Syndrome Virus
      clone (PTKPRRS-3)

<400> SEQUENCE: 13

```
tatgacgtat aggtgttggc tctatgcctt gacatttgta ttgtcaggag ctgtgatcat      60
tgacacagcc caaagcttgc tgcacagaaa caccccttctg tgacagcctc cttcagggga   120
gtttaggggt ctgtccctag caccttgctt ccggagttgc actgctttac ggtctctcca   180
cccctttaac catgtctggg atacttgatc ggtgcacgtg tacccccaat gccagggtgt   240
tcatggcgga gggccaagtc tactgcacac gatgcctcag tgcacggtct ctccttcctc   300
tgaatctcca agttcctgaa ctcggggtgc tgggcctatt ctataggccc gaagagccac   360
tccggtggac gttgccacgt gcattcccca ctgttgagtg ctccccgcc ggagcctgct   420 ggctttctgc catctttcca attgcacgaa tgaccagtgg aaatctgaac tttcaacaaa   480
gaatggtgcg ggtcgcagct gagctttaca gagccggcca gctcacccct gcagtcttga   540
agactctaca agtttatgaa cggggttgcc actggtaccc cattgttgga cctgttcctg   600
gagtggccgt ttatgccaac tccctacatg tgagtgataa accttttcccg ggagcaactc   660 acgtgttaac caacctgccg ctccgcagaa gacccaagcc tgatgatttt gccccctttg   720
agtgtgctat ggctactgtc tatgacattg gtcatgacgc cgtcatgtat gtggccgaag   780
agaaagtctc ctgggccct cgtggcgggg atgaagtgaa attcgaacct gtccccgggg   840
agttgaagtt gattgcgaac cgactccgca cctccttccc gccccaccac gcagtggaca   900
tgtctaagtt caccttcaca gcccctgggc gtggtgtttc tatgcgggtc gaacgccaac   960
```

-continued

| | |
|---|---|
| acggctgcct cccgctgac acagttcctg aaggcaactg ctggtggagc ttgttcaact | 1020 |
| tgctcccact ggaagttcag aacaaagaaa ttcgtcatgc cggccaattt ggctaccaga | 1080 |
| ctaagcatgg tgtctctggc aagtacctac agcggaggct gcaagttaat ggtcttcgag | 1140 |
| cagtaactga cctaaatgga cctatcgtcg tacagtgctt ctccgttaag gagagttgga | 1200 |
| tccgccactt gaaactggcg gaagaaccca gctaccctgg gtttgaggac ctcctcagaa | 1260 |
| taagggttga gcccaacacg tcgccattgg ctgacaagga tgaaaaaatt ttccggtttg | 1320 |
| gcaatcacaa gtggtatggc gctggaaaga gagcaaggaa agcacgctct agtgcgactg | 1380 |
| ctacagtcgc tggccgcgct tgcccgttc gtgaaacccg gcaggtcgag gagcacgagg | 1440 |
| ttgccggcgc caacaaggct gagcacctca aacactactc cccgcctgcc gaagggaatt | 1500 |
| gtggttggca ctgcatttcc gccatcggca accggatgtt gaattccaaa tttgaaacca | 1560 |
| cccttcccga aagagtgaga cctccagatg actgggctac tgatgaggat cttgtgaatg | 1620 |
| ccatccaaat cctcagactc cctgcggcct tggacaggaa cggtgcttgt gctagcgcca | 1680 |
| agtacgtact taagctggaa ggtgagcatt ggactgtcac tgtgaccctt gggatgtccc | 1740 |
| cttctttgct ccctcttgaa tgtgttcagg gctgttgcga gcataagggc ggtcttggtt | 1800 |
| ccccagatgc agtcgaggtt ttcggatttg accctgcctg ccttgactgg ctggctgagg | 1860 |
| tgatgcactt gcctagcaat gccatcccag ccgctctggc cgaaatgtcc ggcgattcca | 1920 |
| atcgtccggc ttccccggtc accacgtgt ggactgtttc gcagttctta gcccgccaca | 1980 |
| acggagggaa tcaccctgac caaatacgct tagggaaaat tatcagcctt tgtcaggtga | 2040 |
| ttgaggactg ctgctgttcc cagaacaaaa ccaaccgggt caccccggag gaggtcgcag | 2100 |
| caaagattga cctgtacctc cgtggtgcaa caaatcttga agaatgcttg gccaggcttg | 2160 |
| agaaagcgcg cccgccacgc gtaatggaca cctcctttga ttgggatgtt gtgctccctg | 2220 |
| gggttgaggc ggcaactcaa acgaccgaac tgccccaagt caaccagtgt cgcgctctgg | 2280 |
| tccctgttgt gactcaaaag tccttggaca caactcggt ccctctgacc gccttttcac | 2340 |
| tggctaacta ctactaccgc gcgcaaggtg acgaagttcg tcaccgtgaa agactaacca | 2400 |
| ccgtgctctc taagttggaa ggggttgttc gagaagaata cgggctcatg ccaaccgggc | 2460 |
| ctggtccacg gccacactg ccacgcgggc tcgacgaact caaggaccag atggaggtgg | 2520 |
| acttgctgaa actggctaac gcccagatga cttcggacat gatggcctgg cagtcgagc | 2580 |
| aggttgacct aaagacttgg gtcaagaact atcgcggtg acaccacca cctcctccgc | 2640 |
| caatagttca gcctcgaaaa acgaagcttg tcaagagctt accagagagc aagcctgttc | 2700 |
| ctgcaccgcg taggaaggtc aggtccgatt gtgactgccc cacccctatcg ggcaacaatc | 2760 |
| ttcctgacag ttgggaagat ttggctgttg gttgcccctc tgatctccct acctcacctg | 2820 |
| agccggtaac acctttgagt gagccggcat ctgtgtccgc accgcgacgc tcttttaggc | 2880 |
| cggtgaagcc tttgagtgaa ccagttccag tccctgcacc gcgcaagact gtgtcccgac | 2940 |
| cggcaacacc tctgagtgag ccgatccctg tgcccgcacc gcgacgcaag tttcagcagg | 3000 |
| tagaaaaagt gaatccggcg gcggcaaccc tggcgtgcca agacgagttt ccagatttgt | 3060 |
| ctgcatcctc gcatactgaa tatgaggcgt ctccccttgt actaccgcag aacggggacg | 3120 |
| ttcttgaagt ggaggagcgg gaagctgagg aaatcctgag tggaatctca gacatactgg | 3180 |
| atgccatcaa accggcatct gcatcatcaa gcagctccct gtcaagtgtg gcgatcacac | 3240 |
| gcccgaaata ctcagctcaa gccatcattg actcgggtgg gccctacagc gggcatctcc | 3300 |

```
aagaggtgaa ggaaacatgc ctaagcatca tgagtgaggc atgtgatgtg accaagcttg   3360
atgaccctgc cacgcaggaa tggctttctc gcatgtggga tagggtggac atgctgactt   3420
ggcgcaatac gtctgttcac caggcgtctc gcaccttgga cgacagattt aagtttctcc   3480
cgaagatgat acttgaaaca ccgccgccct acccgtgtgg gttcgtgatg atgcctcgca   3540
cacctgcacc ctccgtgggt gcggagagcg acctcactat tggctcagtc gctactgagg   3600
acgttccacg catcttcggg aaagtaaatg atgtctgcaa gatgatcgac cagagaccct   3660
tggtactctt tgaaaatgag ctggcagatg accaacctgc cagagatcct cggacatcat   3720
cgcagaggtt tgacgggagc acaccagctc cgcccgcagg cacggatggc accggtttgg   3780
cttcgggccc tggagtgaga gaagtggatt catgtgaggc gagctcaacc gagaaaaatg   3840
aacagccctt cgtgttgaac ggcggcgcca gcacacaggc gtcaacgttt accaatttgc   3900
cgcctccagg cggtatagat gcgggcggga gtgggccgtt acaaacggtg cgaaagaagg   3960
ctgaacggtt ctttgaccta ctaagccgtc aggtttttaa tctcgtctcc catctccctg   4020
ttttcttctc acgccttttc aaacctggcg gtgactattc tccgggtgat tggggttttg   4080
cagcttttac tttattgtgc ctcttttttgt gttacagtta cccggccttt ggtgctgttc   4140
ccctcttggg tgtattttct gggtcttctc ggcgtgttcg aatgggggtt tttggctgct   4200
ggttggcttt tgctgttagt ctgttcaaac ctgtgtccga cccagtcggc gctgcttgtg   4260
aatttgattc gccagagtgt agaaacatcc ttcattcttt tgagcttctc aaaccttggg   4320
accctgttcg cggccttgtt gtgggccccg tcggtctcag tcttgccatt tttggcaggt   4380
tattgggcgg ggcacgccac atctggcact ttttgcttag gtttggcatt gttgcagatt   4440
gtatcttggc tggagcttat gtgctttctc aaggcaggtg taaaaagtgc tggggatctt   4500
gtataagaac tgctcctaat gaggtcgcct ttaacgtgtt tccttttaca cgtgcgacca   4560
ggtcgtcact tatcgacctg tgcaatcggt tttgcgcgcc aaaaggtatg acccccattt   4620
tcctcgccac tgggtggcgc gggtgctgga ccggccgaag ccccattgag caaccctctg   4680
aaaaacccat cgcgtttgcc cagttggatg aaaaaaagat tacggctagg actgtggtcg   4740
cccagcccta tgaccccaac caagctgtaa agtgcttgcg ggtattgcag gcgggcgggg   4800
tgatggtggc tgaggcagtc ccaaaagtgg tcaaagtttc tgctgttcca ttccgagccc   4860
ccttctttcc caccggagtg aaagttgatc ctgaatgcag gattgtggtt gaccccgaca   4920
ctttcactgc agccctccga tctggctact ccaccacaaa cctcgtcctt ggtgtggggg   4980
actttgccca gctgaatgga ttaaaaatca ggcaaatttc caagccttca gggggaggtc   5040
cacacctcat ggctgccctg catgttgctt gctctatggc tctgcacatg cttgttggga   5100
tttatgtgac tgctgtgggt tcttgcggca ccggcactaa cgatccgtgg tgcgccaacc   5160
cgtttgccgt ccctggctac ggacctggct ctctctgcac gtccagattg tgcatctccc   5220
aacatggcct taccctaccc ttgacagcac ttgtggcggg attcggcttt caggaaattg   5280
ccttggttat tttgattttt gtttctatcg gaggcatggc tcatagattg agttgcaagg   5340
ctgatatgct gtgtatttg tttgcaatcg ccagctatgt tgggtacct cttacctggt   5400 tgctttgtgt gtttccttgc tggttgcgct gttttttcgtt gcacccctc accatcctat   5460 ggttggtgtt tttcctgatt tctgtaaata tgccttcagg aatctggcc ttggtgttgt   5520 tgatttctct ctggcttctt ggtcgttata ccaacgttgc cggtcttgtc actccctatg   5580
acattcatca ttacaccagt ggccccgcg gtgttgccgc cttggctacc gcaccagatg   5640
ggacctactt ggccgctgtc cgccgcgccg cgttgactgg tcgcaccatg ctgtttaccc   5700
```

-continued

```
cgtctcagct cgggtccctt cttgagggcg ctttcagaac tcgaaagccc tcactgaaca    5760
ccgttaatgt ggtcgggtcc tccatgggct ctggcggggt gttcaccatc gacgggaaaa    5820
ttaagtgcgt aactgctgca catgtcctta cgggtaattc agctagggtt tccggggttg    5880
gcttcaatca aatgcttgac ttcgatgtga aaggagactt cgccatagcc gattgcccag    5940
actggcaagg ggctgctccc aagacccaat tctgcgagga aggatggact ggccgggcct    6000
attggctaac gtcttctggt gtcgaacccg gcgtcattgg aaaaggattc gccttctgct    6060
tcaccgcgtg cggcgattcc ggatccccag taatcaccga ggccggcgag cttatcggcg    6120
ttcacacggg gtcaaataaa caaggaggag gcatcgtcac gcgccctca ggccagtttt     6180 gtagtgtggc acccgtcaaa ttaagcgaac taagtgaatt ctttgcaggg cctaaggtcc    6240
cgctcggtga tgtgaaagtt ggcagccaca taattgaaga cgtaggcgag gtgccttcag    6300
atctttgcgc cttgcttgct gccaaacctg aactggaagg aggcctctcc accgttcaac    6360
ttctgtgtgt gttttcctc ctgtggagaa tgatgggaca tgcctggacg cccttggttg     6420 ccgtaggggtt tttatcttg aatgaggtcc tcccagctgt cctggtccgg agtgttttct    6480
cctttggaat gtttgtgcta tcctggctca caccatggtc tgcgcaagtt ctgatgatca    6540
ggcttctaac agcagctctt aacaggaata gatggtcact tgccttttac agcctcggtg    6600
caatgactgg ttttgtcgca gatctcgcgg ctactcaggg gtatccgttg caggcagtga    6660
tgagtttgag cacttatgca ttcctgcctc ggataatggt tgtgacttca ccagtcccag    6720
tggttgcgtg tggtgttgtg cacctacttg ccatcatttt gtacttgttt aagtaccgct    6780
gcctgcacaa catccttgtt ggcgatggag tgttctctgc ggctttcttc ctgcgatatt    6840
ttgccgaggg aaagttgagg gaggggtgt cgcaatcctg cgggatgaat catgagtcac     6900
ttaccggtgc cctcgctatg agactcaatg acgaggactt ggatttcctc acgaaatgga    6960
ctgatttcaa gtgctttgtt tctgcgtcca acatgagaaa tgctgcgggc caattcatcg    7020
aggctgccta tgctaaagca cttagagtag aacttgccca gttggtgcag gttgataagg    7080
ttcggggtac tttggccaaa cttgaagctt ttgccgacac cgtggcaccc caactctcgc    7140
ccggtgacat tgttgtcgct cttggccata cgcctgttgg cagtatcttc gacctgaagg    7200
ttggtaacac caagcacact ctccaagcca tcgagaccag ggtccttgct gggtccaaaa    7260
tgaccgtggc gcgcgtcgtc gatccgaccc ccacgccccc acccgcaccc gtgcccatcc    7320
ccctcccacc gaaggttttg gagaacggtc caaacgcttg gggggatgaa gaccgtttga    7380
ataaaaagag gaggcgcagg atggaagccc tcggcatcta tgttatgggc gggaaaaagt    7440
accagaaatt tgggacaag aattccggtg acgtgtttta tgaggagtc cataacaaca     7500 cagatgagtg ggagtgcctc agagttggcg accctgccga ctttgaccct gagaagggaa    7560
ctttgtgtgg gcatgtcacc attgaagata gggcttacca tgtttacacc tccccatctg    7620
gtaagaaatt cctagtcccc gtcaacccag agaacggaag agttcaatgg gaggctgcaa    7680
agctttccgt tgagcaggcc cttggtatga tgaacgtcga cggcgagctg actgccaagg    7740
aactggagaa actgaaaaga ataattgaca aactccaggg cctgactaag gagcagtgtt    7800
taaactgcta gccgccagcg acttgacccg ctgtggtcgc ggcggcttgg ttgttactga    7860
aacagcggta aaaatagtca aatttcacaa ccggaccttc accctgggac ctgtgaattt    7920
aaaagtggcc agtgaggttg agctaaaaga cgcggttgag cacaaccaac acccggttgc    7980
gagaccgatc gatggtggag ttgtgctcct gcgttccgcg gttccttcgc ttatagacgt    8040
```

```
cttgatctcc ggtgctgatg catctcccaa gttacttgcc catcacgggc cgggaaacac      8100
tgggatcgat ggcacgctct gggattttga gtccgaagcc actaaagagg aagtcgcact      8160
cagtgcgcaa ataatacagg cttgtgacat taggcgcggc gacgctcctg aaattggtct      8220
cccttacaag ctgtaccctg ttaggggtaa ccctgagcgg gtgaaaggag ttctgcagaa      8280
tacaaggttt ggagacatac cttacaaaac ccccagtgac actggaagcc cagtgcacgc      8340
ggctgcctgc cttacgccca cgccactcc ggtgactgat gggcgctccg tcttggccac       8400
gaccatgccc cccgggtttg agttatatgt accgaccata ccagcgtctg tccttgatta      8460
ccttgactct aggcctgact gccctaaaca gctgacagag cacggctgcg aagatgccgc      8520
actgaaagac ctctctaaat atgacttgtc cacccaaggc tttgttttac ctggagttct      8580
tcgccttgtg cggaaatacc tgtttgccca tgtaggtaag tgcccacccg ttcatcggcc      8640
ttctacttac cctgctaaga attctatggc tggaataaat gggaacaggt tcccaaccaa      8700
ggacattcag agcgtccctg aaatcgacgt tctgtgcgca caggctgtgc gagaaaactg      8760
gcaaactgtc accccttgta ctcttaagaa acagtattgc gggaagaaga agactaggac      8820
catactcggc accaataact tcatcgcact agcccaccga gcagtgttga gtggtgttac      8880
ccagggcttc atgaaaaagg cgtttaactc gcccatcgcc ctcggaaaga acaagtttaa      8940
ggagctacag actccggtcc tgggcaggtg ccttgaagct gatctcgcat cctgcgatcg      9000
atccacgcct gcaattgtcc gctggtttgc cgccaacctt ctttatgaac ttgcctgtgc      9060
tgaagagcat ctaccgtcgt acgtgctgaa ctgctgccac gacttactgg tcacgcagtc      9120
cggcgcagtg actaagagag gtggcctgtc gtctggcgac ccgatcacct ctgtgtctaa      9180
caccatttat agtttggtga tctatgcaca gcatatggtg cttagttact tcaaaagtgg      9240 tcaccccat ggccttctgt tcttacaaga ccagctaaag tttgaggaca tgctcaaggt        9300 tcaaccctg atcgtctatt cggacgacct cgtgctgtat gccgagtctc ccaccatgcc       9360
aaactatcac tggtgggttg aacatctgaa tttgatgctg gggtttcaga cggacccaaa      9420
gaagacagca ttaacagact cgccatcatt tctaggctgt agaataataa atgggcgcca      9480
gctagtcccc aaccgtgaca ggatcctcgc ggccctcgcc tatcacatga aggcgagtaa      9540
tgtttctgaa tactatgcct cagcggctgc aatactcatg gacagctgtg cttgtttgga      9600
gtatgatact gaatggtttg aagaacttgt agttggaata gcgcagtgcg cccgcaagga      9660
cggctacagc tttcccggca cgccgttctt catgtccatg tgggaaaaac tcaggtccaa      9720
ttatgagggg aagaagtcga gagtgtgcgg gtactgcggg gccccggccc cgtacgctac      9780
tgcctgtggc ctcgacgtct gcatttacca cacccacttc caccagcatt gtccagtcac      9840
aatctggtgt ggccatccag cggggttctgg ttcttgtagt gagtgcaaat ccctgtagg     9900 gaaaggcaca agcccttag acggagtgtt ggaacaagtc ccgtataagc ccccacggac       9960
cgttatcatg catgtggagc agggtctcac ccccccttgat ccaggtagat accaaactcg    10020
ccgcggatta gtctctgtca ggcgtggaat taggggaaat gaagttgaac taccagacgg     10080
tgattatgct agcaccgcct tgctccctac ctgcaaagat atcaacatgg tcgctgtcgc     10140
ttccaacgta ttgcgcagca ggttcatcat cggcccaccc ggtgctggga aacatactg     10200 gctccttcaa caggtccagg atggtgatgt tatttacaca ccaactcacc agaccatgct     10260
tgacatgatt agggctttgg ggacgtgccg gttcaacgtc ccggcaggca caacgctgca    10320 attcccgtc ccctccgca ccggtccgtg ggttcgcatc ctagcggcg gttggtgtcc         10380 tggcaagaat tccttcctag atgaagcagc gtattgcaat caccttgatg ttttgaggct    10440
```

```
tcttagtaaa actaccctca cctgtctagg agacttcaag caactccacc cagtgggttt   10500
tgattctcat tgctatgttt ttgacatcat gcctcaaact caactgaaga ccatctggag   10560
gtttggacag aatatctgtg atgccattca gccagattac agggacaaac tcatgtccat   10620
ggtcaacaca acccgtgtga cctacgtgga aaaacctgtc aggtatgggc aggtcctcac   10680
cccctaccac agggaccgag aggacgacgc catcactatt gactccagtc aaggcgccac   10740
attcgatgtg gttacattgc atttgcccac taaagattca ctcaacaggc aaagagccct   10800
tgttgctatc accagggcaa gacacgctat ctttgtgtat gacccacaca ggcagctgca   10860
gggcttgttt gatcttcctg caaaaggcac acccgtcaac ctcgcagtgc accgcgacgg   10920
gcagctgatc gtgctggata gaaataacaa agaatgcacg gttgctcagg ctctaggcaa   10980
cggggataaa tttagggcca cagacaagcg tgttgtagat tctctccgcg ccatttgtgc   11040
tgatctagaa gggtcgagct ctccgctccc caaggtcgca cacaacttgg gattttattt   11100
ctcacctgat ttaacacagt ttgctaaact cccagtagaa cttgcacctc actggcccgt   11160
ggtgacaacc cagaacaatg aaaagtggcc agatcggctg gttgccagcc ttcgccctat   11220
ccataaatac agccgcgcgt gcatcggtgc cggctatatg gtgggccctt cggtgttcct   11280
aggcactcct ggggtcgtgt catactatct cacaaaattt gttaagggcg aggctcaagt   11340
gcttccggag acggttttca gcaccggccg aattgaggta gactgccggg aatatcttga   11400
tgatcgggag cgagaagttg ctgcgtccct cccacacgct ttcattggcg acgtcaaagg   11460
cactaccgtt ggaggatgtc atcatgtcac ctccagatac ctcccgcgcg tccttcccaa   11520
ggaatcagtt gcggtagtcg gggtttcaag ccccggaaaa gccgcgaaag cattgtgcac   11580
actgacagat gtgtacctcc cagatcttga agcctatctc cacccggaga cccagtccaa   11640
gtgctggaaa atgatgttgg acttcaaaga agttcgacta atggtctgga aagacaaaac   11700
agcctatttc caacttgaag gtcgctattt cacctggtat cagcttgcca gctatgcctc   11760
gtacatccgt gttcctgtca actctacggt gtacttggac ccctgcatgg gccccgccct   11820
ttgcaacagg agagtcgtcg ggtccaccca ctgggggggct gacctcgcgg tcaccccta   11880
tgattacggc gctaaaatta tcctgtctag cgcgtaccat ggtgaaatgc cccccggata   11940
caaaattctg gcgtgcgcgg agttctcgtt ggatgaccca gttaagtaca acatacctg    12000
ggggtttgaa tcggatacag cgtatctgta tgagttcacc ggaaacggtg aggactggga   12060
ggattacaat gatgcgtttc gtgcgcgcca ggaagggaaa atttataagg ccactgccac   12120
cagcwtgaag ttttattttc ccccgggccc tgtcattgaa ccaactttag gcctgaattg   12180
attaattaat ttaaatggcg cgccaatgaa atggggtcca tgcaaagcct ttttgacaaa   12240
attggtcaac tttttgtgga tgctttcacg gaattcttgg tgtccattgt tgatatcatc   12300
atatttttgg ccatttttgtt tggcttcacc gtcgccggtt ggctggtggt cttttgcatc   12360
agattggttt gctccgcgat actccgtgca cgccctgcct ttcactctga gcagttacag   12420
aagatcctat gaggcctttc tttccctgtg tcaggtggac attccacct ggggaatcaa    12480
acatcctctg ggggtgcttt ggcaccataa ggtgtcaacc ctgattgatg aaatggtgtc   12540
gcgtcgaatg taccgcatca tggaaaaagc aggacaggct gcctggaaac aggtggtgag   12600
cgaggccacg ctgtctcgca ttagtagttt ggatgtggtg gctcattttc aacatcttgc   12660
cgccgttgaa gccgagacct gtaaatattt ggcctctcgg ctaccatgc tacacaacct    12720
gcgcatgacg gggtcaaatg taaccatagt atataatggt actttgaatc aggtgtttgc   12780
```

```
cattttcccg accoctggtt cccggccaaa gcttcatgat tttcagcaat ggctgatagc    12840
tgtgcattcg tccatatttt cctctgttgc agcttcttgt actctgtttg ttgtactgtg    12900
gttgcgggtc ccaatgctac gtactgtttt tggtttccgc tggttagggg caatttttcc    12960
ttcgagctct tggtgaatta cacggtgtgc ccaccttgcc tcacccggca agcagccgca    13020
cagcgctacg aacctggcaa ggctcttttgg tgcagaattg gtacgatcg atgtgaggag     13080
gacgatcacg acgagctagg gttcgtgata ccgtctggcc tctccagcga aggccactag    13140
tccagtgttt acgcctggtt ggcgttcttg tccttcagtt acacggccca gtttcacccc    13200
aagatattcg gaatagggaa tgtgagtaaa gtttatgttg acatcaagca tcaatttatt    13260
tgtgctgttc atgacgggca aatcaccacc ttgcctcgcc atgacaacgt ctcagccgtg    13320
ttccagactt attaccagca tcaggtcgac ggcggcaatt ggtttcacct ggaatggctg    13380
cgcccttct tctcctcctg gttggttttg aacgtctctt ggtttctcag gcgttcgcct     13440
gtaagccgtg tttcagttcg agtctttcag acattaagtc caacaccacc gcagctgcag    13500
gctttgctgt cctccaagac atcagctgtc ttaggcatgg ccactcgtcc tctgaggcga    13560
ctcgcaaaag ccgccaatgc cgcacggcga taggaacgcc cgtatacatt actgtcacag    13620
ccaatgtaac agatgagaat tatttgcatt cctctgacct tctcatgctt tcctcttgcc    13680
ttttctacgc ttccgagatg agtgaaaagg gatttgaggt gatatttggc aatgtgtcag    13740
gcatagtggc tgtgtgtgtc aactttacca gctatgtcca acatgtcaag gagttcaccc    13800
agcgctcctt ggtggttgac catgtgcggt tacttcattt tatgcaccct gagactatga    13860
ggtgggcgac cgttttagcc tgtctttttg ccattctgtt ggccatttga atgttcagat    13920
atgttgggga aatgcttgac cgcgggctat tgctcgcaat tgccttttt gtggtgtatc     13980
gtgccgttct gtcttgctgc gctcgtcaac gccaacagca acagcagctc ccatttacag    14040
ttgatttata acttaacgat atgtgagctg aatggcacag actggctgaa caatcatttt    14100
agttgggcag tggagacttt cgttatcttt cctgtgttga ctcatattgt ttcctacggc    14160
gccctcacta ccagccactt ccttgacacg gtcggcctga tcactgtgtc caccgccgga    14220
tactaccatg agcggtatgt cttgagtagc atctatgctg cctgcgccct ggctgcgctg    14280
atttgcttcg tcatcaggtt gacgaaaaat tgtatgtcct ggcgctactc atgtaccaga    14340
tataccaact ttcttctgga caccaagggc agactctatc gctggcggtc acccgtcatc    14400
atagagaaaa ggggtaaaat tgaggttgga ggtgacctga tcgacctcaa gagagttgtg    14460
cttgatggtt ccgcggcaac ccctgtaacc aaagtttcag cggaacaatg gggtcgtcct    14520
tagacgactt ctgcaatgac agcacggctc cacaaaaggt gatcttggca ttttctatca    14580
cctacacacc agtgatgata tatgccctaa aggtgagtcg tggccggctg ctagggcttt    14640
tacacctttt gattttctta aactgtgctt ttaccttcgg gtatatgaca tttgtgcact    14700
ttcagagcac aaacagagtt gcactcacta tgggagcagt agtcgcgctc ctttgggggg    14760
tgtactcagc tatagaaacc tggaaattca tcacttccag atgccgtttg tgcttgctag    14820
gccgcaagta cattctggcc cctgcccacc acgttgagag tgccgcaggc tttcatccga    14880
ttgcggcaag tgataaccac gcatttgtcg tccggcgtcc cggttccact acggttaacg    14940
gcacattggt gccgggttg aaaagcctcg tgttgggtgg cagaagagct gtcaaacggg     15000
gagtggtaaa cctcgttaaa tatgccaaat aacaacggca ggcagcagaa gaaaagaaa     15060
ggggacggcc agccagtcaa tcagctgtgc caaatgttgg gcaggatcat cgcccagcaa    15120
aaccagtcca gaggtaaggg accggggaag aaaagtaaga agaaaagccc ggagaagccc    15180
```

```
cattttcctc tcgcgactga agatgacgtt agacatcact tcacccctag tgagcggcaa  15240
ttgtgtctgt cgtcaatcca gactgccttt aaccaaggcg ctggaacttg taccctgtcg  15300
gattcaggga gaataagtta cgctgtggag tttagtttgc ctacgcatca tactgtgcgc  15360
ctaattcgcg tcacagcatc acccccagca tgatgagctg gcattcttga gacatcccag  15420
tgtttgaatt ggaaggatgt gtggtgaatg gcactgattg atattgtgcc tctaagtcac  15480
ctattcaatt agggcgaccg tatgggggta atatttaatt ggcgtgaacc atgcggccga  15540
aattaaaaaa aaaaaaaaaa aaaaaaaaaa aaaaaaaaaa aaaaaaaaaa aaaaaaaaaa  15600

<210> SEQ ID NO 14
<211> LENGTH: 15566
<212> TYPE: DNA
<213> ORGANISM: Porcine reproductive and respiratory syndrome virus
      clone (PTKPRRS-6)

<400> SEQUENCE: 14
tatgacgtat aggtgttggc tctatgcctt gacatttgta ttgtcaggag ctgtgatcat     60
tgacacagcc caaagcttgc tgcacagaaa caccttctg tgacagcctc cttcagggga    120
gtttaggggt ctgtccctag caccttgctt ccggagttgc actgctttac ggtctctcca    180
cccctttaac catgtctggg atacttgatc ggtgcacgtg tacccccaat gccagggtgt    240
tcatggcgga gggccaagtc tactgcacac gatgcctcag tgcacggtct ctccttcctc    300
tgaatctcca agttcctgaa ctcggggtgc tgggcctatt ctataggccc gaagagccac    360
tccggtggac gttgccacgt gcattcccca ctgttgagtg ctcccccgcc ggagcctgct    420
ggctttctgc catctttcca attgcacgaa tgaccagtgg aaatctgaac tttcaacaaa    480
gaatggtgcg ggtcgcagct gagctttaca gagccggcca gctcacccct gcagtcttga    540
agactctaca agtttatgaa cggggttgcc actggtaccc cattgttgga cctgttcctg    600
gagtggccgt ttatgccaac tccctacatg tgagtgataa acctttcccg ggagcaactc    660
acgtgttaac caacctgccg ctcccgcaga gacccaagcc tgatgatttt tgcccctttg    720
agtgtgctat ggctactgtc tatgacattg gtcatgacgc cgtcatgtat gtggccgaag    780
agaaagtctc ctgggcccct cgtggcgggg atgaagtgaa attcgaacct gtccccgggg    840
agttgaagtt gattgcgaac cgactccgca cctccttccc gccccaccac gcagtggaca    900
tgtctaagtt caccttcaca gcccctgggc gtggtgtttc tatgcgggtc gaacgccaac    960
acggctgcct ccccgctgac acagttcctg aaggcaactg ctggtggagc ttgttcaact   1020
tgctcccact ggaagttcag aacaaagaaa ttcgtcatgc cggccaattt ggctaccaga   1080
ctaagcatgg tgtctctggc aagtacctac agcggaggct gcaagttaat ggtcttcgag   1140
cagtaactga cctaaatgga cctatcgtcg tacagtgctt ctccgttaag gagagttgga   1200
tccgccactt gaaactggcg gaagaaccca gctaccctgg gtttgaggac ctcctcagaa   1260
taagggttga gcccaacacg tcgccattgg ctgacaagga tgaaaaaatt ttccggtttg   1320
gcaatcacaa gtggtatggc gctggaaaga gagcaaggaa agcacgctct agtgcgactg   1380
ctacagtcgc tggccgcgct ttgcccgttc gtgaaacccg gcaggtcgag gagcacgagg   1440
ttgccggcgc caacaaggct gagcacctca aacactactc cccgcctgcc gaagggaatt   1500
gtggttggca ctgcatttcc gccatcggca accggatgtt gaattccaaa tttgaaacca   1560
cccttcccga aagagtgaga cctccagatg actgggctac tgatgaggat cttgtgaatg   1620
ccatccaaat cctcagactc cctgcggcct tggacaggaa cggtgcttgt gctagcgcca   1680
```

```
agtacgtact taagctggaa ggtgagcatt ggactgtcac tgtgacccct gggatgtccc    1740
cttctttgct ccctcttgaa tgtgttcagg gctgttgcga gcataagggc ggtcttggtt    1800
ccccagatgc agtcgaggtt ttcggatttg accctgcctg ccttgactgg ctggctgagg    1860
tgatgcactt gcctagcaat gccatcccag ccgctctggc cgaaatgtcc ggcgattcca    1920
atcgtccggc ttccccggtc accaccgtgt ggactgtttc gcagttctta gcccgccaca    1980
acggagggaa tcaccctgac caaatacgct tagggaaaat tatcagcctt tgtcaggtga    2040
ttgaggactg ctgctgttcc cagaacaaaa ccaaccgggt caccccggag gaggtcgcag    2100
caaagattga cctgtacctc cgtggtgcaa caaatcttga agaatgcttg gccaggcttg    2160
agaaagcgcg cccgccacgc gtaatggaca cctcctttga ttgggatgtt gtgctccctg    2220
gggttgaggc ggcaactcaa acgaccgaac tgccccaagt caaccagtgt cgcgctctgg    2280
tccctgttgt gactcaaaag tccttggaca caactcggt ccctctgacc gccttttcac     2340
tggctaacta ctactaccgc gcgcaaggtg acgaagttcg tcaccgtgaa agactaacca    2400
ccgtgctctc taagttggaa ggggttgttc gagaagaata cgggctcatg ccaaccgggc    2460
ctggtccacg gcccacactg ccacgcgggc tcgacgaact caaggaccag atggaggtgg    2520
acttgctgaa actggctaac gcccagatga cttcggacat gatggcctgg gcagtcgagc    2580
aggttgacct aaagacttgg gtcaagaact atccgcggtg gacaccacca cctcctccgc    2640
caatagttca gcctcgaaaa acgaagcttg tcaagagctt accagagagc aagcctgttc    2700
ctgcaccgcg taggaaggtc aggtccgatt gtgactgccc caccctatcg ggcaacaatc    2760
ttcctgacag ttgggaagat ttggctgttg gttgcccctc tgatctccct acctcacctg    2820
agccggtaac acctttgagt gagccggcat ctgtgtccgc accgcgacgc tcttttaggc    2880
cggtgaagcc tttgagtgaa ccagttccag tccctgcacc gcgcaagact gtgtcccgac    2940
cggcaacacc tctgagtgag ccgatccctg tgcccgcacc gcgacgcaag tttcagcagg    3000
tagaaaaagt gaatccggcg gcggcaaccc tggcgtgcca agacgagttt ccagatttgt    3060
ctgcatcctc gcatactgaa tatgaggcgt ctccccttgt actaccgcag aacggggacg    3120
ttcttgaagt ggaggagcgg gaagctgagg aaatcctgag tggaatctca gacatactgg    3180
atgccatcaa accggcatct gcatcatcaa gcagctccct gtcaagtgtg gcgatcacac    3240
gcccgaaata ctcagctcaa gccatcattg actcgggtgg gccctacagc gggcatctcc    3300
aagaggtgaa ggaaacatgc ctaagcatca tgagtgaggc atgtgatgtg accaagcttg    3360
atgaccctgc cacgcaggaa tggctttctc gcatgtggga tagggtggac atgctgactt    3420
ggcgcaatac gtctgttcac caggcgtctc gcacccttgga cgacagattt aagtttctcc    3480
cgaagatgat acttgaaaca ccgccgccct accgtgtgg gttcgtgatg atgcctcgca    3540
cacctgcacc ctccgtgggt gcggagagcg acctcactat tggctcagtc gctactgagg    3600
acgttccacg catcttcggg aaagtaaatg atgtctgcaa gatgatcgac cagagaccct    3660
tggtactctt tgaaaatgag ctggcagatg accaacctgc cagagatcct cggacatcat    3720
cgcagaggtt tgacgggagc acaccagctc cgcccgcagg cacggatggc accggtttgg    3780
cttcgggccc tggagtgaga gaagtggatt catgtgaggc gagctcaacc gagaaaaatg    3840
aacagcccct cgtgttgaac ggcggcgcca gcacacaggc gtcaacgttt accaatttgc    3900
cgcctccagg cggtatagat gcgggcggga gtgggccgtt acaaacggtg cgaaagaagg    3960
ctgaacggtt cttttgaccta ctaagccgtc aggtttttaa tctcgtctcc catctccctg    4020
```

-continued

```
ttttcttctc acgccttttc aaacctggcg gtgactattc tccgggtgat tggggttttg    4080
cagcttttac tttattgtgc ctcttttgt gttacagtta cccggccttt ggtgctgttc     4140
ccctcttggg tgtattttct gggtcttctc ggcgtgttcg aatgggggtt tttggctgct    4200
ggttggcttt tgctgttagt ctgttcaaac ctgtgtccga cccagtcggc gctgcttgtg    4260
aatttgattc gccagagtgt agaaacatcc ttcattcttt tgagcttctc aaaccttggg    4320
accctgttcg cggccttgtt gtgggccccg tcggtctcag tcttgccatt tttggcaggt    4380
tattgggcgg ggcacgccac atctggcact ttttgcttag gtttggcatt gttgcagatt    4440
gtatcttggc tggagcttat gtgctttctc aaggcaggtg taaaaagtgc tggggatctt    4500
gtataagaac tgctcctaat gaggtcgcct ttaacgtgtt ccttttaca cgtgcgacca     4560 ggtcgtcact tatcgacctg tgcaatcggt tttgcgcgcc aaaaggtatg acccccattt    4620
tcctcgccac tgggtggcgc gggtgctgga ccggccgaag ccccattgag caaccctctg    4680
aaaaacccat cgcgtttgcc cagttggatg aaaaaaagat tacggctagg actgtggtcg    4740
cccagcccta tgaccccaac caagctgtaa agtgcttgcg ggtattgcag gcgggcgggg    4800
tgatggtggc tgaggcagtc ccaaaagtgg tcaaagtttc tgctgttcca ttccgagccc    4860
ccttctttcc caccggagtg aaagttgatc ctgaatgcag gattgtggtt gaccccgaca    4920
ctttcactgc agccctccga tctggctact ccaccacaaa cctcgtcctt ggtgtggggg    4980
actttgccca gctgaatgga ttaaaaatca ggcaaatttc caagccttca ggggaggtc     5040 cacacctcat ggctgccctg catgttgctt gctctatggc tctgcacatg cttgttggga    5100
tttatgtgac tgctgtgggt tcttgcggca ccggcactaa cgatccgtgg tgcgccaacc    5160
cgtttgccgt ccctggctac ggacctggct ctctctgcac gtccagattg tgcatctccc    5220
aacatggcct taccctaccc ttgacagcac ttgtggcggg attcggcttt caggaaattg    5280
ccttggttat tttgattttt gtttctatcg gaggcatggc tcatagattg agttgcaagg    5340
ctgatatgct gtgtatttg tttgcaatcg ccagctatgt ttgggtacct cttacctggt     5400
tgctttgtgt gtttccttgc tggttgcgct gttttttcgtt gcaccccctc accatcctat    5460
ggttggtgtt tttcctgatt tctgtaaata tgccttcagg aatcttggcc ttggtgttgt    5520
tgatttctct ctggcttctt ggtcgttata ccaacgttgc cggtcttgtc actcccatg     5580 acattcatca ttacaccagt ggcccccgcg gtgttgccgc cttggctacc gcaccagatg    5640
ggacctactt ggccgctgtc cgccgcgccg cgttgactgg tcgcaccatg ctgtttaccc    5700
cgtctcagct cgggtccctt cttgagggcg cttttcagaac tcgaaagccc tcactgaaca    5760
ccgttaatgt ggtcgggtcc tccatgggct ctggcgggt gttcaccatc gacgggaaaa     5820
ttaagtgcgt aactgctgca catgtcctta cgggtaattc agctagggtt tccggggttg    5880
gcttcaatca aatgcttgac ttcgatgtga aggagactt cgccatagcc gattgcccag     5940 actgcaagg ggctgctccc aagacccaat tctgcgagga aggatggact ggccgggcct    6000
attggctaac gtcttctggt gtcgaacccg gcgtcattgg aaaaggattc gccttctgct    6060
tcaccgcgtg cggcgattcc ggatccccag taatcaccga ggccggcgag cttatcggcg    6120
ttcacacggg gtcaaataaa caaggaggag gcatcgtcac gcgcccctca ggccagttt     6180 gtagtgtggc acccgtcaaa ttaagcgaac taagtgaatt cttgcaggg cctaaggtcc     6240 cgctcggtga tgtgaaagtt ggcagccaca taattgaaga cgtaggcgag gtgccttcag    6300 atcttgcgc cttgcttgct gccaaacctg aactggaagg aggcctctcc accgttcaac    6360
ttctgtgtgt gttttcctc ctgtggagaa tgatgggaca tgcctggacg cccttggttg     6420
```

```
ccgtagggtt ttttatcttg aatgaggtcc tcccagctgt cctggtccgg agtgttttct    6480
cctttggaat gtttgtgcta tcctggctca caccatggtc tgcgcaagtt ctgatgatca    6540
ggcttctaac agcagctctt aacaggaata gatggtcact tgccttttac agcctcggtg    6600
caatgactgg ttttgtcgca gatctcgcgg ctactcaggg gtatccgttg caggcagtga    6660
tgagtttgag cacttatgca ttcctgcctc ggataatggt tgtgacttca ccagtcccag    6720
tggttgcgtg tggtgttgtg cacctacttg ccatcatttt gtacttgttt aagtaccgct    6780
gcctgcacaa catccttgtt ggcgatgag tgttctctgc ggctttcttc ctgcgatatt    6840
ttgccgaggg aaagttgagg gagggggtgt cgcaatcctg cgggatgaat catgagtcac    6900
ttaccggtgc cctcgctatg agactcaatg acgaggactt ggatttcctc acgaaatgga    6960
ctgatttcaa gtgctttgtt tctgcgtcca acatgagaaa tgctgcgggc caattcatcg    7020
aggctgccta tgctaaagca cttagagtag aacttgccca gttggtgcag gttgataagg    7080
ttcggggtac tttggccaaa cttgaagctt ttgccgacac cgtggcaccc caactctcgc    7140
ccggtgacat tgttgtcgct cttggccata cgcctgttgg cagtatcttc gacctgaagg    7200
ttggtaacac caagcacact ctccaagcca tcgagaccag ggtccttgct gggtccaaaa    7260
tgaccgtggc gcgcgtcgtc gatccgaccc ccacgccccc acccgcaccc gtgcccatcc    7320
ccctcccacc gaaggttttg gagaacggtc caaacgcttg gggggatgaa gaccgtttga    7380
ataaaaagag gaggcgcagg atggaagccc tcggcatcta tgttatgggc gggaaaaagt    7440
accagaaatt ttgggacaag aattccggtg acgtgtttta tgaggaggtc cataacaaca    7500
cagatgagtg ggagtgcctc agagttggcg accctgccga ctttgaccct gagaagggaa    7560
cttttgtgtgg gcatgtcacc attgaagata gggcttacca tgtttacacc tccccatctg    7620
gtaagaaatt cctagtcccc gtcaacccag agaacggaag agttcaatgg gaggctgcaa    7680
agctttccgt tgagcaggcc cttggtatga tgaacgtcga cggcgagctg actgccaagg    7740
aactggagaa actgaaaaga ataattgaca aactccaggg cctgactaag gagcagtgtt    7800
taaactgcta gccgccagcg acttgacccg ctgtggtcgc ggcggcttgg ttgttactga    7860
aacagcggta aaaatagtca aatttcacaa ccggaccttc accctgggac ctgtgaattt    7920
aaaagtggcc agtgaggttg agctaaaaga cgcggttgag cacaaccaac accgggttgc    7980
gagaccgatc gatggtggag ttgtgctcct gcgttccgcg gttccttcgc ttatagacgt    8040
cttgatctcc ggtgctgatg catctcccaa gttacttgcc catcacgggc cgggaaacac    8100
tgggatcgat ggcacgctct gggattttga gtccgaagcc actaaagagg aagtcgcact    8160
cagtgcgcaa ataatacagg cttgtgacat taggcgcggc gacgctcctg aaattggtct    8220
cccttacaag ctgtaccctg ttaggggtaa ccctgagcgg gtgaaaggag ttctgcagaa    8280
tacaaggttt ggagacatac cttacaaaac ccccagtgac actggaagcc cagtgcacgc    8340
ggctgcctgc cttacgccca cgccactcc ggtgactgat gggcgctccg tcttggccac    8400
gaccatgccc cccgggtttg agttatatgt accgaccata ccagcgtctg tccttgatta    8460
ccttgactct aggcctgact gccctaaaca gctgacagag cacggctgcg aagatgccgc    8520
actgaaagac ctctctaaat atgacttgtc cacccaaggc tttgttttac ctggagttct    8580
tcgccttgtg cggaaatacc tgtttgccca tgtaggtaag tgcccacccg ttcatcggcc    8640
ttctacttac cctgctaaga attctatggc tggaataaat gggaacaggt tcccaaccaa    8700
ggacattcag agcgtccctg aaatcgacgt tctgtgcgca caggctgtgc gagaaaactg    8760
```

-continued

```
gcaaactgtc accccttgta ctcttaagaa acagtattgc gggaagaaga agactaggac    8820
catactcggc accaataact tcatcgcact agcccaccga gcagtgttga gtggtgttac    8880
ccagggcttc atgaaaaagg cgtttaactc gcccatcgcc ctcggaaaga acaagtttaa    8940
ggagctacag actccggtcc tgggcaggtg ccttgaagct gatctcgcat cctgcgatcg    9000
atccacgcct gcaattgtcc gctggtttgc cgccaacctt ctttatgaac ttgcctgtgc    9060
tgaagagcat ctaccgtcgt acgtgctgaa ctgctgccac gacttactgg tcacgcagtc    9120
cggcgcagtg actaagagag gtggcctgtc gtctggcgac ccgatcaccT ctgtgtctaa    9180
caccatttat agtttggtga tctatgcaca gcatatggtg cttagttact tcaaaagtgg    9240
tcacccccat ggccttctgt tcttacaaga ccagctaaag tttgaggaca tgctcaaggt    9300
tcaaccctg atcgtctatt cggacgacct cgtgctgtat gccgagtctc ccaccatgcc    9360
aaactatcac tggtgggttg aacatctgaa tttgatgctg gggtttcaga cggacccaaa    9420
gaagacagca ttaacagact cgccatcatt tctaggctgt agaataataa atgggcgcca    9480
gctagtcccc aaccgtgaca ggatcctcgc ggccctcgcc tatcacatga aggcgagtaa    9540
tgtttctgaa tactatgcct cagcggctgc aatactcatg acagctgtg cttgtttgga    9600
gtatgatact gaatggtttg aagaacttgt agttggaata gcgcagtgcg cccgcaagga    9660
cggctacagc tttcccggca cgccgttctt catgtccatg tgggaaaaac tcaggtccaa    9720
ttatgagggg aagaagtcga gagtgtgcgg gtactgcggg gccccggccc cgtacgctac    9780
tgcctgtggc ctcgacgtct gcatttacca cacccacttc caccagcatt gtccagtcac    9840
aatctggtgt ggccatccag cgggttctgg ttcttgtagt gagtgcaaat ccctgtagg    9900
gaaaggcaca agccctttag acggagtgtt ggaacaagtc ccgtataagc ccccacggac    9960
cgttatcatg catgtggagc agggtctcac ccccttgat ccaggtagat accaaactcg   10020
ccgcggatta gtctctgtca ggcgtggaat taggggaaat gaagttgaac taccagacgg   10080
tgattatgct agcaccgcct tgctccctac ctgcaaagag atcaacatgg tcgctgtcgc   10140
ttccaacgta ttgcgcagca ggttcatcat cggcccaccc ggtgctggga aaacatactg   10200
gctccttcaa caggtccagg atggtgatgt tatttacaca ccaactcacc agaccatgct   10260
tgacatgatt agggctttgg ggacgtgccg gttcaacgtc ccggcaggca caacgctgca   10320
attccccgtc ccctcccgca ccggtccgtg ggttcgcatc ctagccggcg gttggtgtcc   10380
tggcaagaat tccttcctag atgaagcagc gtattgcaat caccttgatg ttttgaggct   10440
tcttagtaaa actaccctca cctgtctagg agacttcaag caactccacc cagtgggttt   10500
tgattctcat tgctatgttt ttgacatcat gcctcaaact caactgaaga ccatctggag   10560
gtttggacag aatatctgtg atgccattca gccagattac agggacaaac tcatgtccat   10620
ggtcaacaca acccgtgtga cctacgtgga aaaacctgtc aggtatgggc aggtcctcac   10680
cccctaccac agggaccgag aggacgacgc catcactatt gactccagtc aaggcgccac   10740
attcgatgtg gttacattgc atttgcccac taaagattca ctcaacaggc aaagagccct   10800
tgttgctatc accagggcaa gacacgctat ctttgtgtat gacccacaca ggcagctgca   10860
gggcttgttt gatcttcctg caaaaggcac acccgtcaac ctcgcagtgc accgcgacgg   10920
gcagctgatc gtgctggata gaaataacaa agaatgcacg gttgctcagg ctctaggcaa   10980
cggggataaa tttagggcca cagacaagcg tgttgtagat tctctccgcg ccatttgtgc   11040
tgatctagaa gggtcgagct ctccgctccc caaggtcgca cacaacttgg gattttattt   11100
ctcacctgat ttaacacagt ttgctaaact cccagtagaa cttgcacctc actggcccgt   11160
```

```
ggtgacaacc cagaacaatg aaaagtggcc agatcggctg gttgccagcc ttcgccctat    11220
ccataaatac agccgcgcgt gcatcggtgc cggctatatg gtgggccctt cggtgtttct    11280
aggcactcct ggggtcgtgt catactatct cacaaaattt gttaagggcg aggctcaagt    11340
gcttccggag acggttttca gcaccggccg aattgaggta gactgccggg aatatcttga    11400
tgatcgggag cgagaagttg ctgcgtccct cccacacgct ttcattggcg acgtcaaagg    11460
cactaccgtt ggaggatgtc atcatgtcac ctccagatac ctcccgcgcg tccttcccaa    11520
ggaatcagtt gcggtagtcg gggtttcaag ccccggaaaa gccgcgaaag cattgtgcac    11580
actgacagat gtgtacctcc cagatcttga agcctatctc cacccggaga cccagtccaa    11640
gtgctggaaa atgatgttgg acttcaaaga agttcgacta atggtctgga agacaaaaac    11700
agcctatttc caacttgaag gtcgctattt cacctggtat cagcttgcca gctatgcctc    11760
gtacatccgt gttcctgtca actctacggt gtacttggac ccctgcatgg gccccgccct    11820
ttgcaacagg agagtcgtcg ggtccaccca ctgggggggct gacctcgcgg tcacccctta    11880
tgattacggc gctaaaatta tcctgtctag cgcgtaccat ggtgaaatgc cccccggata    11940
caaaattctg gcgtgcgcgg agttctcgtt ggatgaccca gttaagtaca acatacctg    12000
ggggtttgaa tcggatacag cgtatctgta tgagttcacc ggaaacggtg aggactggga    12060
ggattacaat gatgcgtttc gtgcgcgcca ggaagggaaa atttataagg ccactgccac    12120
cagcwtgaag ttttatttc ccccgggccc tgtcattgaa ccaactttag gcctgaattg    12180
attaattaat ttaaatggcg cgccaatgaa atggggtcca tgcaaagcct ttttgacaaa    12240
attggtcaac tttttgtgga tgctttcacg gaattcttgg tgtccattgt tgatatcatc    12300
atatttttgg ccattttgtt tggcttcacc gtcgccggtt ggctggtggt cttttgcatc    12360
agattggttt gctccgcgat actccgtgca cgccctgcct ttcactctga gcagttacag    12420
aagatcctat gaggcctttc tttccctgtg tcaggtggac attcccacct ggggaatcaa    12480
acatcctctg ggggtgcttt ggcaccataa ggtgtcaacc ctgattgatg aaatggtgtc    12540
gcgtcgaatg taccgcatca tggaaaaagc aggacaggct gcctggaaac aggtggtgag    12600
cgaggccacg ctgtctcgca ttagtagttt ggatgtggtg gctcattttc aacatcttgc    12660
cgccgttgaa gccgagacct gtaaatattt ggcctctcgg ctaccatgc tacacaacct    12720
gcgcatgacg gggtcaaatg taaccatagt atataatggt actttgaatc aggtgttgc    12780
cattttcccg acccctggtt cccggccaaa gcttcatgat tttcagcaat ggctgatagc    12840
tgtgcattcg tccatatttt cctctgttgc agcttcttgt actctgtttg ttgtactgtg    12900
gttgcgggtc ccaatgctac gtactgtttt tggtttccgc tggttagggg caattttttcc    12960
ttcgagctct tggtgaatta cacggtgtgc ccaccttgcc tcacccggca agcagccgca    13020
cagcgctacg aacctggcaa ggctctttgg tgcagaattg ggtacgatcg atgtgaggag    13080
gacgatcacg acgagctagg gttcgtgata ccgtctggcc tctccagcga aggccactag    13140
tccagtgttt acgcctggtt ggcgttcctg tccttcagct acacggccca gttccatccc    13200
gagatatttg ggataggaa tgtgagtcta gtttatgttg acatcaagca ccaagtcatc    13260
tgtgccgttc acgacgggca gaacaccacc ttgcctcgcc atgacaatat ctcagccgta    13320
tttcagacct actaccaaca tcaggtcgac ggcggcaatt ggtttcacct agaatggctg    13380
cgtcctttct tttcctcttg gttggtttta aatgtttcgt ggtttctcag gcgttcgcct    13440
gcaagccatg tttcagttcg agtctttcag acatcaaaac caacactacc gcagcatcaa    13500
```

```
acttcgttgt cctccaggac atcagctgcc ttaggcatgg cgactcgtcc tctccggcga    13560
ttcgcaaaag ccctcagtgc cgcacggcga tagggacgcc cgtgtacatc actatcacag    13620
ccaatgtcac agatgagaat tatttacatt cctctgatct cctcatgctt tcttcttgcc    13680
ttttctatgc ttctgagatg agcgaaaagg gattcaaggt ggtatttggc aatgtgtcag    13740
gcatcgtggc tgtgtgtgtc aactttacca gctacgtcca acatgtcaag gagtttaccc    13800
aacgctcctt ggtggtcgat catgtgcggc tgcttcattt catgacacct gagaccatga    13860
ggtgggcaac cgttttagcc tgtcttttg ccatcctgct ggcaatttga atgttcaagt    13920
atgttgggga aatgcttgac cgcgggctgt tgctcgcgat tgccttttt gtggtgtatc    13980 gtgccgttct gttttgctgt gatcgtcaac gccaacagca gcagcagctc tcattttcag    14040
tcgatttata acttgacgct atgtgagctg aacggcacag attggctggc taaaagatt    14100 gactgggcag tggagacttt tgttatcttt cccgtgttga ctcacattgt ttcctatggt    14160
gcacttacca ccagccattt ccttgacaca gttggtctgg ttactgtgtc caccgccggg    14220
ttttatcacg ggcggtatgt cttgagtagc atctacgcgg tctgtgccct ggctgcgttg    14280
atttgcttcg tcattagatt tgcgaagaac tgcatgtcct ggcgctactc ttgtaccaga    14340
tataccaact tccttctgga cactaagggc agactctatc gttggcggtc gcccgttatc    14400
atagagaaag ggggtaaggt tgaggtcgaa ggtcacctga tcgacctcaa aagagttgtg    14460
cttgatggtt ccgtggcaac ccctttaacc agagtttcag cggaacaatg gggtcgtctc    14520
tagacgactt ttgccatgat agcacggctc cacaaaaggt gcttttggcg ttttctatta    14580
cctacacgcc agtgatgata tatgctctaa aggtaagtcg cggccgactg ttagggcttc    14640 tgcaccttt gatctttctg aattgtgctt ttaccttcgg gtacatgaca ttcgtgcact    14700
ttcagagtac aaatagggtc gcgctcacta tgggagcagt agttgcactt ctttgggggg    14760
tgtactcagc catagaaacc tggaaattca tcacctccag atgccgtttg tgcttgctag    14820
gccgcaggta cattctggcc cctgcccacc acgtcgaaag tgccgcgggc tttcatccga    14880
ttgcggcaag tgataaccac gcatttgtcg tccggcgtcc cggctccact acggttaacg    14940
gcacattggt gcccgggttg aaaagcctcg tgttgggtgg cagaaaagct gttaaacagg    15000
gagtggtaaa ccttgtcaaa tatgccaaat aacaacggca agcagcaaaa gaaaagaag    15060 gggaatggcc agccagtcaa tcagctgtgc cagatgctgg gtaagatcat cgcccagcaa    15120
aaccagtcca gaggcaaggg accggggaag aaaaataaga agaaaaccc ggagaagccc    15180 cattttcctc tagcgaccga agatgacgtc aggcatcact tcaccctag tgagcggcaa    15240 ttgtgtctgt cgtcgatcca gactgccttc aaccagggcg ctggaacttg taccctgtca    15300
gattcaggga ggataagtta cactgtggag tttagtttgc cgacgcatca tactgtgcgc    15360
ctgattcgtg ccacggcatc accctcagca tgatgggctg gcattcttga agcacctcag    15420
tgttagaatt ggaagaatgt gtggtgaatg gcactgattg acactgtgcc tctaagtcac    15480
ctattcaatt agggcgaccg tgtgggggta agtttaatt ggcgagaacc atgcggccgt    15540
aattaaaaaa aaaaaaaaaa aaaaaa                                         15566
```

<210> SEQ ID NO 15
<211> LENGTH: 25
<212> TYPE: DNA
<213> ORGANISM: artificial sequence
<220> FEATURE:
<223> OTHER INFORMATION: PSAF primer

<400> SEQUENCE: 15
ccttaattaa tttaaatggc gcgcc                                              25

<210> SEQ ID NO 16
<211> LENGTH: 24
<212> TYPE: DNA
<213> ORGANISM: artificial sequence
<220> FEATURE:
<223> OTHER INFORMATION: SR12709 primer

<400> SEQUENCE: 16
ccccgtcatg cgcaggttgt gtag                                               24

<210> SEQ ID NO 17
<211> LENGTH: 2449
<212> TYPE: DNA
<213> ORGANISM: partial sequence Porcine Reproductive and Respiratory
      Syndrome Virus field isolate

<400> SEQUENCE: 17
gcctctccag cgaaggccac tagtccagtg tttacgcctg gttggcgttc ctgtccttca          60
gctacacggc ccagttccat cccgagatat tgggatagg gaatgtgagt ctagtttatg          120
ttgacatcaa gcaccaagtc atctgtgccg ttcacgacgg cagaacacc accttgcctc          180 gccatgacaa tatctcagcc gtatttcaga cctactacca acatcaggtc gacggcggca          240
attggtttca cctagaatgg ctgcgtcctt ctttttcctc ttggttggtt ttaaatgttt          300
cgtggtttct caggcgttcg cctgcaagcc atgtttcagt tcgagtcttt cagacatcaa          360
aaccaacact accgcagcat caaacttcgt tgtcctccag gacatcagct gccttaggca          420
tggcgactcg tcctctccgg cgattcgcaa aagccctcag tgccgcacgg cgatagggac          480
gcccgtgtac atcactatca cagccaatgt cacagatgag aattatttac attcctctga          540
tctcctcatg ctttcttctt gccttttcta tgcttctgag atgagcgaaa agggattcaa          600
ggtggtattt ggcaatgtgt caggcatcgt ggctgtgtgt gtcaactttta ccagctacgt          660 ccaacatgtc aaggagttta cccaacgctc cttggtggtc gatcatgtgc ggctgcttca          720
tttcatgaca cctgagacca tgaggtgggc aaccgtttta gcctgtcttt ttgccatcct          780
gctggcaatt tgaatgttca agtatgttgg ggaaatgctt gaccgcgggc tgttgctcgc          840
gattgccttt tttgtggtgt atcgtgccgt tctgttttgc tgtgatcgtc aacgccaaca          900
gcagcagcag ctctcatttt cagtcgattt ataacttgac gctatgtgag ctgaacggca          960
cagattggct ggctaaaaga tttgactggg cagtggagac ttttgttatc tttcccgtgt         1020
tgactcacat tgttcctat ggtgcactta ccaccagcca tttccttgac acagttggtc         1080
tggttactgt gtccaccgcc gggttttatc acgggcggta tgtcttgagt agcatctacg         1140
cggtctgtgc cctggctgcg ttgatttgct tcgtcattag atttgcgaag aactgcatgt         1200
cctggcgcta ctcttgtacc agatatacca acttccttct ggacactaag ggcagactct         1260
atcgttggcg gtcgcccgtt atcatagaga aagggggtaa ggttgaggtc gaaggtcacc         1320
tgatcgacct caaaagagtt gtgcttgatg gttccgtggc aacccctta accagagttt         1380 cagcggaaca atgggtcgt ctctagacga cttttgccat gatagcacgg ctccacaaaa         1440
ggtgcttttg cgttttcta ttacctacac gccagtgatg atatatgctc taaaggtaag         1500
tcgcggccga ctgttagggc ttctgcacct ttttgatcttt ctgaattgtg cttttacctt         1560
cgggtacatg acattcgtgc actttcagag tacaaatagg gtcgcgctca ctatgggagc         1620
agtagttgca cttctttggg gggtgtactc agccatagaa acctggaaat tcatcacctc         1680

-continued

```
cagatgccgt ttgtgcttgc taggccgcag gtacattctg gccctgccc accacgtcga    1740 aagtgccgcg ggctttcatc cgattgcggc aagtgataac cacgcatttg tcgtccggcg    1800
tcccggctcc actacggtta acggcacatt ggtgcccggg ttgaaaagcc tcgtgttggg    1860
tggcagaaaa gctgttaaac agggagtggt aaaccttgtc aaatatgcca aataacaacg    1920
gcaagcagca aaagaaaaag aaggggaatg gccagccagt caatcagctg tgccagatgc    1980
tgggtaagat catcgcccag caaaaccagt ccagaggcaa gggaccgggg aagaaaaata    2040
agaagaaaaa cccggagaag ccccattttc ctctagcgac cgaagatgac gtcaggcatc    2100
acttcacccc tagtgagcgg caattgtgtc tgtcgtcgat ccagactgcc ttcaaccagg    2160
gcgctggaac ttgtaccctg tcagattcag ggaggataag ttacactgtg gagtttagtt    2220
tgccgacgca tcatactgtg cgcctgattc gtgccacggc atcaccctca gcatgatggg    2280
ctggcattct tgaagcacct cagtgttaga attggaagaa tgtgtggtga atggcactga    2340
ttgacactgt gcctctaagt cacctattca attagggcga ccgtgtgggg gtaaagttta    2400
attggcgaga accatgcggc cgtaattaaa aaaaaaaaaa aaaaaaaa                 2449
```